US009309291B2

(12) United States Patent
Ault-Riche et al.

(10) Patent No.: US 9,309,291 B2
(45) Date of Patent: Apr. 12, 2016

(54) BROAD SPECTRUM INFLUENZA A NEUTRALIZING VACCINES AND D-PEPTIDIC COMPOUNDS, AND METHODS FOR MAKING AND USING THE SAME

(71) Applicants: Reflexion Pharmaceuticals, San Francisco, CA (US); The Governing Council of the University of Toronto, Toronto (CA)

(72) Inventors: Dana Ault-Riche, San Francisco, CA (US); Maruti Uppalapati, Toronto (CA)

(73) Assignees: Reflexion Pharmaceuticals, Inc., San Francisco, CA (US); The Governing Council of the University of Toronto, Toronto (CA)

( * ) Notice: Subject to any disclaimer, the term of this patent is extended or adjusted under 35 U.S.C. 154(b) by 290 days.

(21) Appl. No.: 13/691,549

(22) Filed: Nov. 30, 2012

(65) Prior Publication Data

US 2013/0171186 A1 Jul. 4, 2013

Related U.S. Application Data

(60) Provisional application No. 61/566,332, filed on Dec. 2, 2011.

(51) Int. Cl.
```
C07K 14/11      (2006.01)
G01N 33/68      (2006.01)
G01N 33/569     (2006.01)
C07K 14/005     (2006.01)
A61K 38/00      (2006.01)
```
(52) U.S. Cl.
CPC .............. *C07K 14/11* (2013.01); *C07K 14/005* (2013.01); *G01N 33/56983* (2013.01); *G01N 33/68* (2013.01); *G01N 33/6845* (2013.01); *A61K 38/00* (2013.01); *C12N 2760/16122* (2013.01); *G01N 2333/11* (2013.01)

(58) Field of Classification Search
None
See application file for complete search history.

(56) References Cited

U.S. PATENT DOCUMENTS

| | | | |
|---|---|---|---|
| 5,780,221 A | 7/1998 | Schumacher et al. | |
| 6,040,133 A | 3/2000 | Kent et al. | |
| 6,548,279 B1 | 4/2003 | Kent et al. | |
| 7,118,856 B2 | 10/2006 | Kent et al. | |
| 7,408,026 B1 | 8/2008 | Kent et al. | |
| 2010/0093624 A1 | 4/2010 | Low et al. | |
| 2012/0014972 A1* | 1/2012 | Hodges et al. | 424/159.1 |

FOREIGN PATENT DOCUMENTS

| | | |
|---|---|---|
| WO | WO2011/094363 A2 | 8/2011 |
| WO | WO2012/078313 A2 | 6/2012 |

OTHER PUBLICATIONS

Schumacher et al. Science 1996, vol. 271, pp. 1854-1857.*
Schumacher et al. J of Medical Chem 2010, vol. 53, pp. 4441-4449.*
Eckert, D.M., et al., "Inhibiting HIV-1 Entry: Discovery of D-Peptide Inhibitors that Target the gp41 Coiled-Coil Pocket", Cell, vol. 99, pp. 103-115 (1999).
Matsubara, T., et al., "Sialic Acid-Mimic Peptides As Hemmag-glutinin Inhibitors for Anti-Influenza Therapy", Journal of Medicinal Chemistry, vol. 53, pp. 4441-4449 (2010).
Schumacher, T.N.M., et al., "Identification of D-Peptide Ligands Through Mirror-Image Phage Display", Science, vol. 271, pp. 1854-1857 (1996).
Alexander et al., "A minimal sequence code for switching protein structure and function", PNAS, vol. 106, No. 50, pp. 21149-21154 (2009).
Baker et al., "Computer-based redesign of a protein folding pathway", Nature Structural Biology, vol. 8, No. 7, pp. 602-605 (2001).
Baker et al., "Crystal structures and increased stabilization of the protein G variants with switched folding pathways NuG1 and NuG2", Protein Science, vol. 11, pp. 2924-2931 (2002).
Binz et al. "Engineering novel binding proteins from nonim-munoglobulin domains", Nature Biotechnology, vol. 23, No. 10, pp. 1257-1268 (2005).
Bommakanti et al., "Design of an HA2-based *E. coli* expressed influenza immunogen that protects mice from pathogenic challenge", PNAS, vol. 107, pp. 13701-13706 (2010).
Byeon et al., "A Protein Contortionist: Core Mutations of GB1 that Induce Dimerization and Domain Swapping", J. Mol. Biol., vol. 333, pp. 141-152 (2003).
Cochran et al., "Phage-display as a tool for quantifying protein stability determinants", Eur. J. Biochem., vol. 271, pp. 1623-1629 (2004).
Corti et al. "A neutralizing antibody selected from plasma cells that binds to group 1 and group 2 influenza A hemagglutinins", Science Express, 1205669, pp. 1-8 (2011).
DeGrado et al., "Thermodynamic Genetics of the Folding of the B1 Immunoglobulin-Binding Domain From Streptococcal Protein G", Proteins: Structure, Function, and Genetics, vol. 21, pp. 11-21 (1995).

(Continued)

*Primary Examiner* — Shanon A Foley
*Assistant Examiner* — Myron Hill
(74) *Attorney, Agent, or Firm* — Bret E. Field; Glenn J. Foulds; Bozicevic, Field & Francis LLP

(57) ABSTRACT

GB1 peptidic compounds that specifically bind to a hemag-glutinin target protein, and libraries that include the same, as well as methods of making and using the same, are provided. Also provided are methods and compositions for making and using the compounds. Also provided are hemagglutinin mimics and fragments and methods of using the same, including methods of screening for GB1 peptidic compounds and methods of using conjugates the mimics as influenza A vaccines. Aspects of the invention include methods of screening libraries of L-peptidic compounds for specific binding to a D-peptidic hemagglutinin target protein. Once a L-peptidic compound has been identified that specifically binds to the D-peptidic hemagglutinin target protein, the D-enantiomer of the selected L-peptidic compound may be produced. In some embodiments, the D-enantiomer of the selected L-peptidic compound binds to, and in some instances, neutralizes influenza virus particles.

19 Claims, 12 Drawing Sheets

(56) References Cited

OTHER PUBLICATIONS

Dintzis et al., "A Comparison of the Immunogenicity of a Pair of Enantiomeric Proteins", Proteins: Structure, Function, and Genetics, vol. 16, pp. 306-308 (1993).

Ekiert et al. "A highly conserved neutralizing epitope on group 2 influenza A viruses", Science Express, 1204839, pp. 1-9 (2011).

Fleishman, et al., "Computational Design of Proteins Targeting the Conserved Stem Region of Influenza Hemagglutinin", Science, vol. 332, pp. 816-821 (2011).

Funke et al., "Mirror image phage display—a method to generate D-peptide ligands for use in diagnostic or therapeutical applications", Mol. BioSyst., vol. 5, No. 8, pp. 783-786 (2009).

Ghosh et al., "A Minimalist Approach toward Protein Recognition by Epitope Transfer from Functionally Evolved β-Sheet Surfaces", J. Am. Chem. Soc., vol. 128, No. 44, pp. 14356-14363 (2006).

Ghosh et al., "Inhibition of β-Amyloid Fibrillization by Directed Evolution of a β-Sheet Presenting Miniature Protein", J. Am. Chem. Soc., vol. 128, No. 45, pp. 14456-14457 (2006).

Gronenborn et al., "A Novel, Highly Stable Fold of the Immunoglobulin Binding Domain of Streptococcal Protein G", Science, vol. 253, pp. 657-661 (1991).

Gronenborn et al., "Core mutants of the immunoglobulin binding domain of streptococcal protein G: stability and structural integrity", FEBS Letters, vol. 398, pp. 312-316 (1996).

Kim et al., "Measurement of the β-sheet-forming propensities of amino acids", Nature, vol. 367, pp. 660-663 (1994).

Kim et al., "Identification of D-peptide ligands through mirror-image phage display", Science, vol. 271, pp. 1854-1857 (1996).

Mayo et al., "Design, structure and stability of a hyperthermophilic protein variant", Nature Structural Biology, vol. 5, No. 6, pp. 470-475 (1998).

Mayo et al., "Probing the role of packing specificity in protein design", Proc. Natl. Acad. Sci. USA, vol. 94, pp. 10172-10177 (1997).

Rajashekhar et al., "Anti-proliferative Properties of novel D-Peptide-VEGF-Antagonists: Plausible Role in Anti-angiogenic and Anti-tumor Formation", FASEB J., Apr. 2009, 23 (Meeting Abstract Supplement) 634.5.

Regan et al., "A Thermodynamic Scale for the Beta-Sheet Forming Tendencies of the Amino Acids", Biochemistry, vol. 33, pp. 5510-5517 (1994).

Regan et al., "Guidelines for Protein Design: The Energetics of Beta-Sheet Side Chain Interactions", Science, vol. 270, pp. 980-982 (1995).

Regan et al., "Novel metal-binding proteins by design", Structural Biology, vol. 2, No. 5, pp. 368-373 (1995).

Willbold et al., "Mirror-image phage display: aiming at the mirror", ChemBioChem, vol. 4, pp. 811-815 (2003).

Wunderlich et al., "In Vitro Evolution of a Hyperstable Gβ1 Variant", J. Mol. Biol., vol. 363, pp. 545-557 (2006).

* cited by examiner

Figure 1

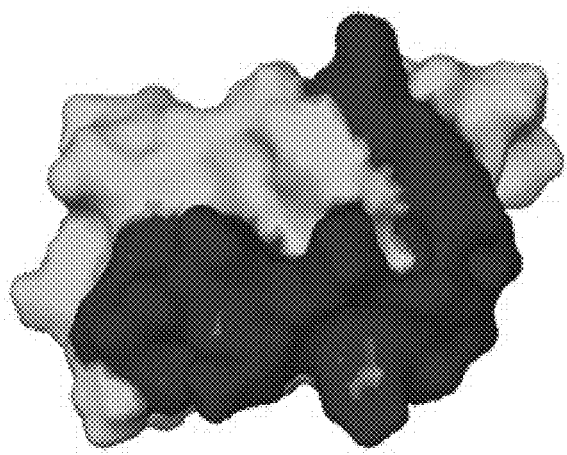
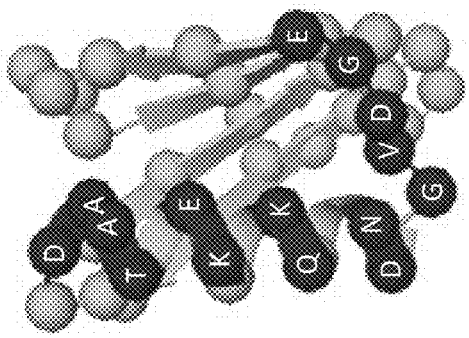

Figure 2

Library 1

GATGATAAGGGCTAGCACGTACAAACTGATTCTGAACGGCAAACCCTGAAAGGTGAAACCACCGAAGCAGTGGATGCAGCAGAAAAAGTT
 D D K G G S T Y K L I L N G K T L K G E T T E A V D A A T A E K V
TTCAAACAGTACGCCAACGATAATGGCGTGGATGGCGAATGGACCTACGATGATGCCACCAAAACCTTCACGGTTACCGAAGGCGGTTCTGACAAAACT
 F K Q Y A N D N G V D G E W T Y D D A T K T F T V T E G G S D K T
(SEQ ID NO:45)
(SEQ ID NO:46)

ACGACCGAAGCAGTGGKHTKHTKHTKHTGCAKHTKHTKHTAATKHTKHTKHTAATKHTKHTKHTKHTKHTTGGACCTACGATGAT
(SEQ ID NO:12)
ACGACCGAAGCAGTGKHTKHTKHTKHTKHTGCAKHTKHTKHTGTTTTCKHTKHTKHTTACGCCKHTKHTKHTAATKHTKHTKHTTGGACCTACGATGAT
(SEQ ID NO:13)
ACGACCGAAGCAGTGKHTKHTKETKHTKHTGCAKHTKHTKHTGTTTTCKHTKHTKHTTACGCCKHTKHTKHTAATKHTKHTKHTTGGACCTACGATGAT
(SEQ ID NO:14)

Figure 3

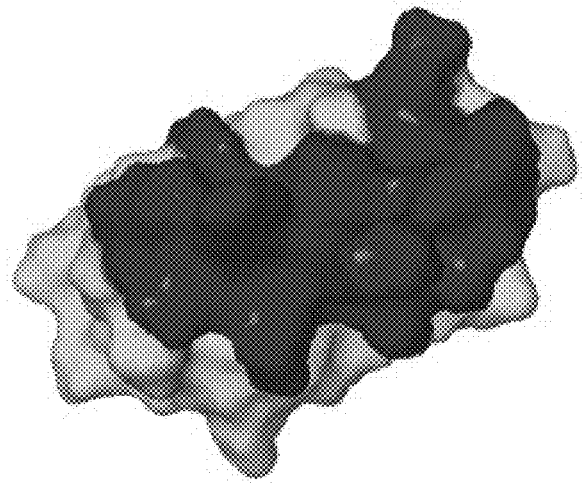

Library 2

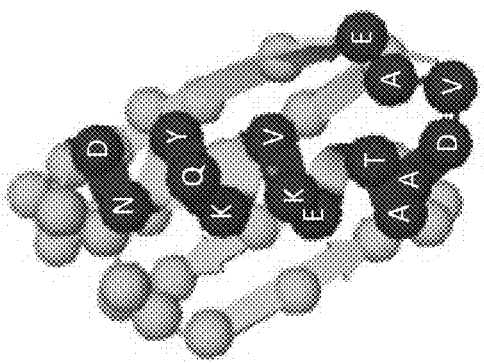

```
GATGATAAGGCGGTAGCACGTACAAACTGATTCTGAACGGCAAGACCCTGAAAGGTGAAACCACGACCGAAGCAGTGGATGCAGCAACGGCAGAAAAAGTT
 D  D  K  G  G  S  T  Y  K  L  I  L  N  G  K  T  L  K  G  E  T  T  T  E  A  V  D  A  A  T  A  E  K  V
TTCAAACAGTACGCCAACGATAATGGCGTGGATGGTGAATGGACCTACGATGATGCCACCAAAACCTTCACGGTTACCGAAGGCGGTTCTGACAAAACT
 F  K  Q  Y  A  N  D  N  G  V  D  G  E  W  T  Y  D  D  A  T  K  T  F  T  V  T  E  G  G  S  D  K  T
(SEQ ID NO:45)
(SEQ ID NO:46)

GGTGAAACCACCACGACCKHTKHTKHTKHTKHTKHTGCCAKHTKHTKHTTCCKHTKHTKHTAATGGCGTGGATGGT
(SEQ ID NO:15)
GGTGAAACCACCACGACCKHTKHTKHTKHTKHTKHTGCAKHTKHTKHTCCKHTKHTKHTAATGGCGTGGATGGT
(SEQ ID NO:16)
GGTGAAACCACCACGACCKHTKHTKHTKHTKHTKHTKHTGCAKHTKHTKHTCCAKHTKHTKHTTCCKHTKHTKHTGCCKHTKHTKHTAATGGCGTGGATGGT
(SEQ ID NO:17)
```

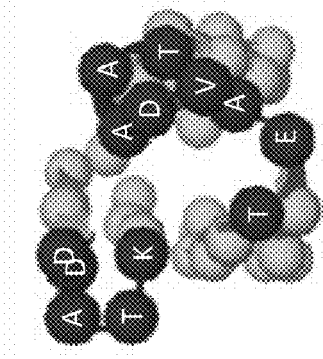

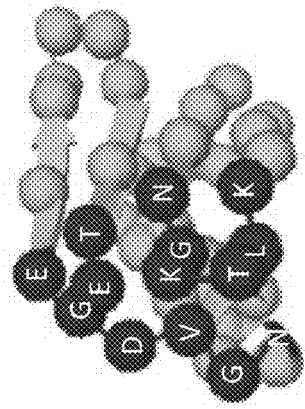

Figure 5

```
GATGATAAGGCGGTAGCACGTACAAACTGATTCTGAATGGCAAAACCCTGAAAGGTGAAACCACGACCGAAGCAGTGGATGCAGCGACCGCAGAAAAAGTT
 D  D  K  G  G  S  T  Y  K  L  I  L  N  G  K  T  L  K  G  E  T  T  T  E  A  V  D  A  A  T  A  E  K  V
TTCAAACAGTACGCCAACGATAATGGCGTGGATGGCGAATGGACCTACGATGATGCGACCAAAACCTTCACGGTTACCGAAGGCGGTTCTGACAAAACT
 F  K  Q  Y  A  N  D  N  G  V  D  G  E  W  T  Y  D  D  A  T  K  T  F  T  V  T  E  G  G  S  D  K  T
(SEQ ID NO:45)
(SEQ ID NO:46)

ACGTACAAACTGATTCTG KHT KHT KHT KHT GGTGAAACCACGACCGAA (SEQ ID NO:25)
ACGTACAAACTGATTCTG KHT KHT KHT KHT GGTGAAACCACGACCGAA (SEQ ID NO:26)
ACGTACAAACTGATTCTG KHT KHT KHT KHT GGTGAAACCACGACCGAA (SEQ ID NO:27)

AAACAGTACGCCAACGAT KHT KHT KHT KHT TGGACCTACGATGATGCG (SEQ ID NO:28)
AAACAGTACGCCAACGAT KHT KHT KHT KHT TGGACCTACGATGATGCG (SEQ ID NO:29)
AAACAGTACGCCAACGAT KHT KHT KHT KHT TGGACCTACGATGATGCG (SEQ ID NO:30)

ACGAAAACCTTCACGGTT KHT KHT KHT KHT GGCGGGTTCTGACAAAACT (SEQ ID NO:31)
```

Library 4

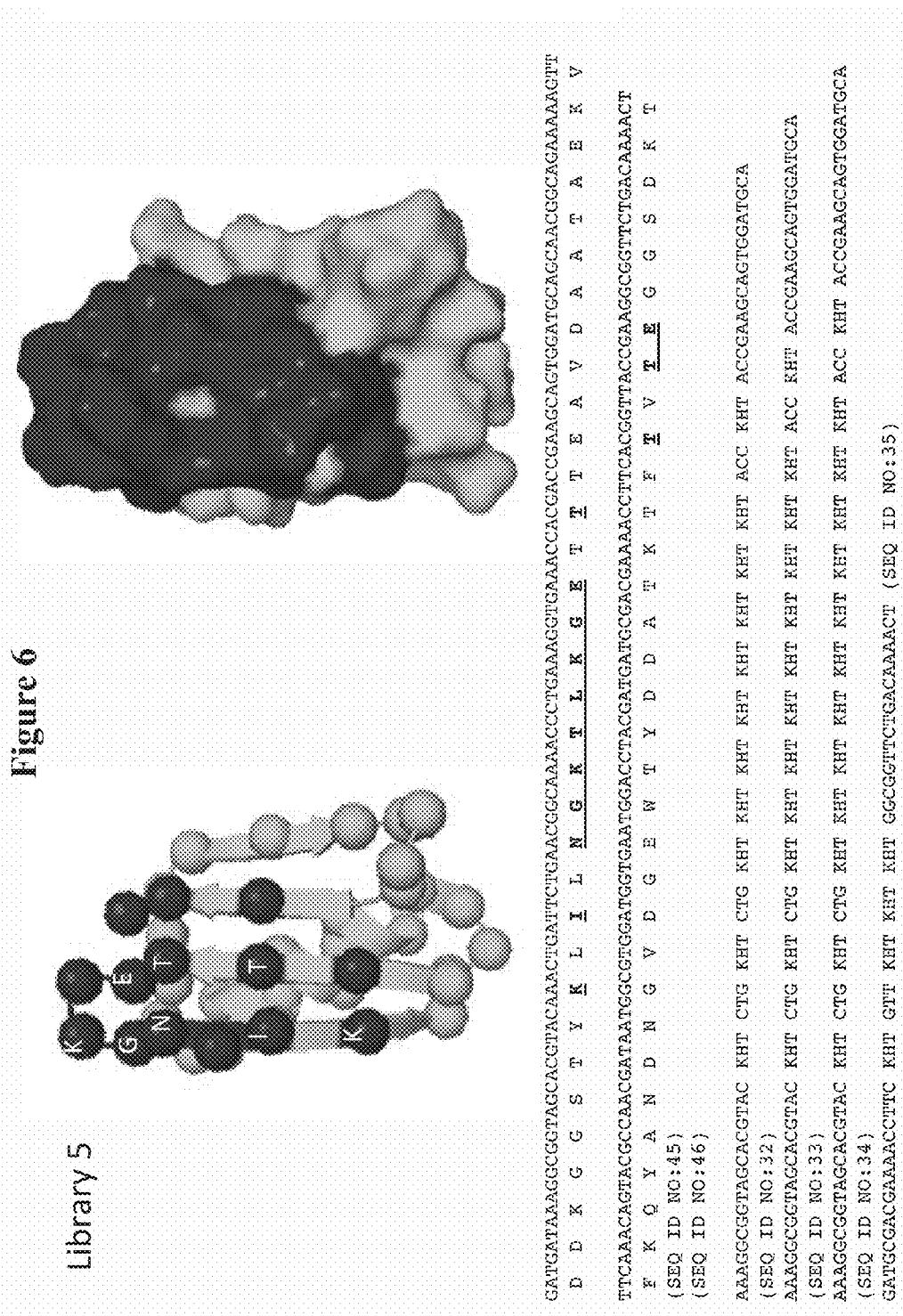

Figure 7 library 6

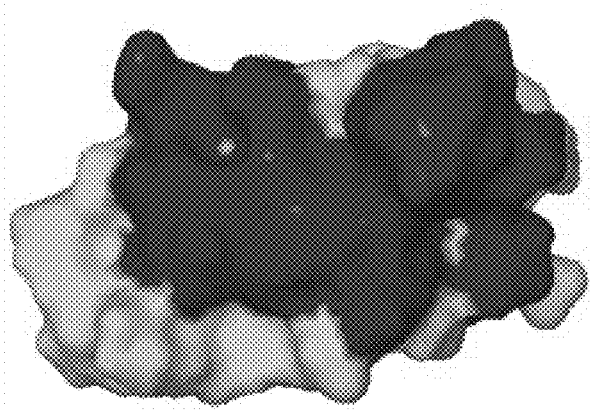
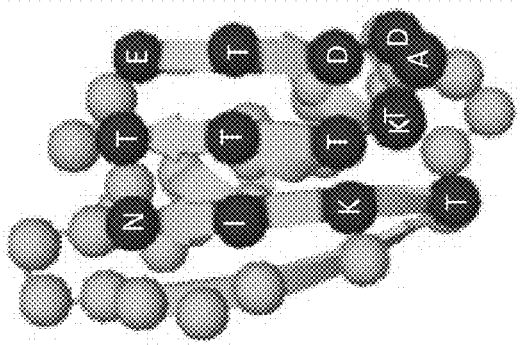

```
GATGATAAAGGCGTAGCCACGTACAAACTGAATCTGAACGGCAAAACCCTGAAAGGTGAAACCACGACCGAAGCAGTGGATGCAGCAACGGCAGAAAAAGTT
 D  D  K  G  G  S  T  Y  K  L  I  N  G  K  T  L  K  G  E  T  T  T  E  A  V  D  A  A  T  A  E  K  V
TTTCAAACAGTACGCCAACGATAATGGCCTGGATGGTGAATGGTTACGGACCGAAGAAACTTCACGGTTACCGAAGGCGGTTCTGACAAAACT
 F  K  Q  Y  A  N  D  N  G  V  D  D  G  E  W  T  Y  D  D  A  T  K  T  F  T  V  T  E  G  G  S  D  K  T
(SEQ ID NO:45)
(SEQ ID NO:46)

GATGATAAAGGCGTGGTAGC KHT KHT TAC KHT GGCAAAACCCTGAAAGGT (SEQ ID NO:36)
GATAATGGCGTGGATGGTGATGGTKHTTACKHTTACKHTTGGKHTTACKHTTACKHTTCKHTGTTKHTGAAGGCGGTTCTGACAAA(SEQ ID NO:37)
GATAATGGCGTGGATGGTKHTTGGKHTTACKHTTACKHTTACKHTTCKHTGTTKHTGAAGGCGGTTCTGACAAA (SEQ ID NO:38)
GATAATGGCGTGGATGGTKHTTGGKHTTACKHTTACKHTTACKHTTCKHTGTTKHTGAAGGCGGTTCTGACAAA(SEQ ID NO:39)
```

Figure 9

| | Epitope residue # | 1 | 2 | 3 | 4 | 5 | 6 | 7 | 8 | 9 | 10 | 11 | 12 | 13 | 14 | 15 | 16 | 17 | 18 | 19 | 20 | 21 | | SEQ ID NO: |
|---|---|---|---|---|---|---|---|---|---|---|---|---|---|---|---|---|---|---|---|---|---|---|---|---|
| | register 1 | e | f | g | a | b | c | d | e | f | g | a | b | c | d | e | f | g | a | b | c | d | | |
| a | H1 Epitope | Q | K | S | T | Q | N | A | – | – | – | – | T | S | K | V | N | S | V | – | E | – | | 115 |
| X X A A | H1 overlap | Q | K | S | a | Q | N | d | – | D | G | – | T | S | d | V | N | S | a | – | E | d | | 116 |
| a – A L | H1 overlap | Q | K | S | – | Q | L | – | – | D | G | – | T | S | L | V | N | S | – | – | E | L | | 117 |

| | Epitope residue # | 1 | 2 | 3 | 4 | 5 | 6 | 7 | 8 | 9 | 10 | 11 | 12 | 13 | 14 | 15 | 16 | 17 | 18 | 19 | 20 | SEQ ID NO: |
|---|---|---|---|---|---|---|---|---|---|---|---|---|---|---|---|---|---|---|---|---|---|---|
| | register 2 | d | e | f | g | a | b | c | d | e | f | g | a | b | c | d | e | f | g | a | b | |
| | register 3 | c | d | e | f | g | a | b | c | d | e | f | g | a | b | c | d | e | f | g | a | |
| | register 4 | b | c | d | e | f | g | a | b | c | d | e | f | g | a | b | c | d | e | f | g | |
| | register 5 (3M) | a | b | c | d | e | f | g | a | b | c | d | e | f | g | a | b | c | d | e | f | |
| | register 6 | g | a | b | c | d | e | f | g | a | b | c | d | e | f | g | a | b | c | d | e | |
| | register 7 | f | g | a | b | c | d | e | f | g | a | b | c | d | e | f | g | a | b | c | d | |
| | register 2 | Q | Q | S | – | – | N | A | L | D | G | – | – | S | K | K | N | S | V | – | E | 118 |
| | register 3 | Q | L | S | I | Q | – | – | – | L | G | – | T | – | K | L | L | S | V | – | – | 119 |
| | register 4 | Q | Q | – | T | Q | N | A | – | D | D | – | T | S | – | V | N | N | L | – | E | 120 |
| | register 5 (3M) | – | K | S | T | Q | N | A | – | D | G | – | T | S | K | V | N | S | V | – | E | 121 |
| | register 6 | Q | – | S | L | Q | N | A | – | – | – | L | L | S | K | V | S | S | L | – | E | 122 |
| | register 7 | Q | K | – | T | Q | L | A | – | D | – | – | T | L | K | – | N | S | V | L | L | 123 |

Figure 10

```
IAALQKSIQNLIDGITSLVNSIIELMNTCRR
                              |      H1
IAALQKSIQNLIDGITSLVNSIIELMNTCRR

IAALKESIQKLIDGITNLVNSIIELMNTCRR
                              |      H2
IAALKESIQKLIDGITNLVNSIIELMNTCRR

IAALLKSIQALIDQINGLLNRIIELTNECRR
                              |      H3
IAALLKSIQALIDQINGLLNRIIELTNECRR

IAALLKSIQALIDQINGLLNRIIELTNDCRR
                              |      H4
IAALLKSIQALIDQINGLLNRIIELTNDCRR

IAALKESIQKLIDGITNLVNSIIDLMNTCRR
                              |      H5
IAALKESIQKLIDGITNLVNSIIDLMNTCRR

IAALRESIQKLVDGITNLVNSIIDLMNTCRR
                              |      H6
IAALRESIQKLVDGITNLVNSIIDLMNTCRR
```

Figure 11

```
IAALYKSIQSLIDQITGLLNRIIELTNQCRR
                              |   H7
IAALYKSIQSLIDQITGLLNRIIELTNQCRR

IAALQKSIQELIDKITNLVNNIVDLMNRCRR
                              |   H8
IAALQKSIQELIDKITNLVNNIVDLMNRCRR

IAALKGSIQKLIDKITSLVNNIIDLMNKCRR
                              |   H9
IAALKGSIQKLIDKITSLVNNIIDLMNKCRR

IAALYKSIQALIDQITGLLNRIIELTNTCRR
                              |   H10
IAALYKSIQALIDQITGLLNRIIELTNTCRR

IAALKESIQKLIDQITSLVNNIVDLMNTCRR
                              |   H11
IAALKESIQKLIDQITSLVNNIVDLMNTCRR

IAALRDSIQRLIDNIQNLLNNIIDLMNKCRR
                              |   H12
IAALRDSIQRLIDNIQNLLNNIIDLMNKCRR
```

Figure 12

```
IAALKESIQKLIDQITTLINNIIDLMNGCRR
                              |  H13
 IAALKESIQKLIDQITTLINNIIDLMNGCRR

IAALLKSIQALIDQINGLLNRIIELTNECRR
                              |  H14
IAALLKSIQALIDQINGLLNRIIELTNECRR

IAALYKSIQALIDQITGLLNRIIELTNKCRR
                              |  H15
IAALYKSIQALIDQITGLLNRIIELTNKCRR

IAALKASIQKLIDEITTLINNIIELMNGCRR
                              |  H16
IAALKASIQKLIDEITTLINNIIELMNGCRR
```

BROAD SPECTRUM INFLUENZA A NEUTRALIZING VACCINES AND D-PEPTIDIC COMPOUNDS, AND METHODS FOR MAKING AND USING THE SAME

CROSS REFERENCE TO RELATED APPLICATIONS

Pursuant to 35 U.S.C. §119(e), this application claims priority to the filing date of U.S. provisional application Ser. No. 61/566,332, filed Dec. 2, 2011, the disclosure of which is herein incorporated by reference.

This application is related to copending U.S. application entitled "GB1 peptidic libraries and methods of screening the same" filed on Nov. 10, 2011 to Sidhu et al. and accorded Ser. No. 13/294,072, and U.S. provisional application Ser. No. 61/413,318 filed Nov. 12, 2010, which are entirely incorporated herein by reference. This application is related to copending U.S. application entitled "Methods And Compositions For Identifying D-Peptidic Compounds That Specifically Bind Target Proteins" filed on Nov. 10, 2011 to Sidhu et al. and accorded Ser. No. 13/294,078, and U.S. provisional application Ser. No. 61/413,318 filed Nov. 12, 2010, which are entirely incorporated herein by reference.

INTRODUCTION

Essentially all biological processes depend on molecular recognition mediated by proteins. The ability to manipulate the interactions of such proteins is of interest for both basic biological research and for the development of therapeutics.

Between 50 million and 100 million people worldwide are suspected to have died as a direct result of three influenza A pandemics (1918 H1N1 Spanish flu; 1957 H2N2 Asian flu; 1968 H3N2 Hong Kong flu). In 1997 a highly pathogenic avian influenza virus H5N1 emerged in South-East Asia resulting in 385 reported cases with a 63% overall mortality, and in 2009 a highly pathogenic H1N1 swine influenza outbreak occurred. The threat of a serious influenza pandemic remains a significant concern. Agents that can effectively neutralize influenza A and other viruses, both as a prophylactic and active treatment for infected individuals, are of interest.

SUMMARY

GB1 peptidic compounds that specifically bind to a hemagglutinin target protein, and libraries that include the same, as well as methods of making and using the same, are provided. Also provided are methods and compositions for making and using the compounds. Also provided are hemagglutinin mimics and fragments and methods of using the same, including methods of screening for GB1 peptidic compounds and methods of using the mimics as influenza A vaccines. Aspects of the invention include methods of screening libraries of L-peptidic compounds for specific binding to a D-peptidic hemagglutinin target protein. Once a L-peptidic compound has been identified that specifically binds to the D-peptidic hemagglutinin target protein, the D-enantiomer of the selected L-peptidic compound may be produced. In some embodiments, the D-enantiomer of the selected L-peptidic compound binds to, and in some instances, neutralizes influenza virus particles.

BRIEF DESCRIPTION OF THE DRAWINGS

FIG. 1 illustrates exemplary L-peptidic libraries for use in the subject methods. The underlying sequence is of a GB1 scaffold domain (SEQ ID NO:1) where the positions of the variant amino acids in Libraries 1 to 6 are shown as dark blocks in the sequence (SEQ ID NO:1). The asterisks indicate positions (e.g., 1, 9, 19, 38, 47 and 55) at which mutations may include insertion of amino acids.

FIGS. 2 to 7 illustrate exemplary phage display libraries 1 to 6 of FIG. 1. Ribbon (left) and space filling (right) structural representations depict the variant amino acid positions in dark blocks. Oligonucleotide and amino acid sequences show the GB1 peptidic scaffold in the context of the fusion protein with GGS linkers at the N- and C-termini of the scaffold. Also shown are the oligonucleotide sequences synthesized for use in preparation of the libraries by Kunkel mutagenesis that include KHT codons at variant amino acid positions to encode variable regions of GB1 peptidic compounds.

FIG. 9 illustrates the alignment of an HA epitope with the coiled coil template to produce a template epitope sequence for an HA mimic. Top: Register 1 alignment of positions 1-20 of an HA epitope with the heptad repeat $(abcdefg)_n$ of a coiled coil scaffold. Residues "a" and "d" in the H1 overlap general formula are hydrophobic residues (e.g., I or L). Bottom: illustration of the register 2-6 alignments of positions 1-20 of an HA epitope. M3 denotes the register utilized in sequences 3M1, 3M2 and 3 MP by Hodges et al. (US2012/0014972).

FIGS. 10-12 illustrate the sequences of HA coiled coil mimics for use as vaccines or as D-peptidic targets for screening. FIG. 10, H1-H6 mimics (SEQ ID NOs:124-129); FIG. 11, H7-H12 mimics (SEQ ID NOs:130-135); and FIG. 12, H13-H16 (SEQ ID NOs: 136-139).

DEFINITIONS

Figure 8:
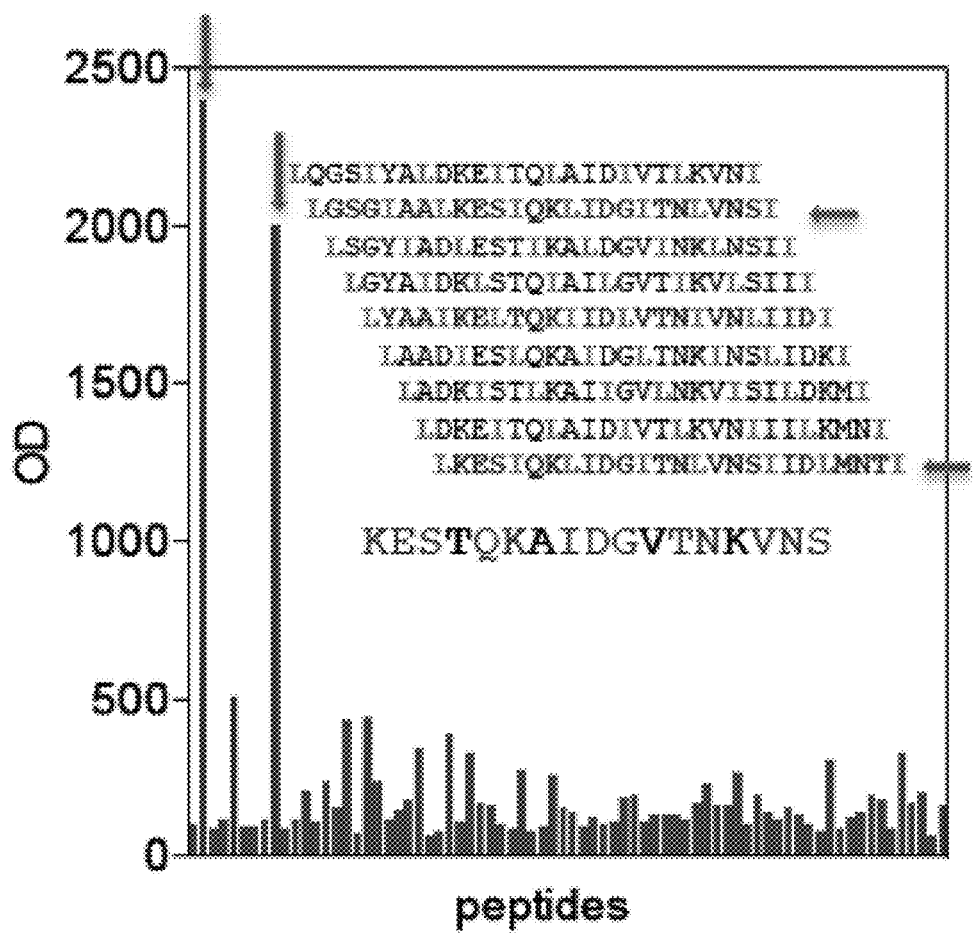
FIG. 8 illustrates the ability of a broadly neutralizing antibody to Group 1 and Group 2 influenza A viruses to bind to coiled coil peptide mimics (SEQ ID NOs:105-113) of a portion of the hemagglutinin protein KESTQKAIDGVT-NKVNS (SEQ ID NO:114). Overlapping peptides are shown in which at various positions in an underlying sequence are included either an Ile or Leu residue in order to promote a helical coiled coil structure. Absorbance (O.D.) indicates the amount of binding to the antibody. The arrows identify the sequences in which the placements of Ile and Leu residues did not disrupt binding to the antibody (see Fig. S8B of supporting online material, revised 12 Aug. 2011, Corti et al. Science Express, 28 Jul. 2011, 1205669).

As used herein, the term "peptidic" refers to a moiety that is composed of amino acid residues. The term "peptidic" includes compounds or libraries in which the conventional backbone has been replaced with non-naturally occurring or synthetic backbones, and peptides in which one or more naturally occurring amino acids, or enantiomers thereof, have been replaced with one or more non-naturally occurring or synthetic amino acids, or enantiomers thereof. Any of the depictions of sequences found herein (e.g., using one-letter or three-letter codes) may represent a L-amino acid or a D-amino acid version of the sequence. Unless noted otherwise, the capital and small letter codes for L- and D-amino acid residues, respectively, are not utilized.

As used herein, the terms "polypeptide" and "protein" are used interchangeably. The term "polypeptide" also includes post translational modified polypeptides or proteins. The term "polypeptide" includes polypeptides in which the conventional backbone has been replaced with non-naturally occurring or synthetic backbones, and peptides in which one or more of the conventional amino acids have been replaced with one or more non-naturally occurring or synthetic amino acids, or enantiomers thereof. In some instances, polypeptides may be of any length, e.g., 2 or more amino acids, 4 or more amino acids, 10 or more amino acids, 20 or more amino acids, 30 or more amino acids, 40 or more amino acids, 50 or more amino acids, 60 or more amino acids, 100 or more amino acids, 300 or more amino acids, 500 or more or 1000 or more amino acids.

As used herein, the terms "naturally occurring amino acid" and "non-naturally occurring amino acid" may be used to refer to both L- and D-versions of these amino acids. For example, a D-peptidic compound may be described as including naturally occurring amino acids, e.g., D-enantiomers of amino acids such as A, C, D, E, F, H, I, K, L, M, N, P, Q, R, S, T, V, W and Y.

As used herein, the term "scaffold" or "scaffold domain" refers to a peptidic framework from which a library of compounds arose, and against which the compounds are able to be compared. When a compound of a library arises from amino acid mutations at various positions within a scaffold, the amino acids at those positions are referred to as "variant amino acids." Such variant amino acids may confer on the resulting peptidic compounds different functions, such as specific binding to a target protein.

As used herein, the term "mutation" refers to a deletion, insertion, or substitution of an amino acid(s) residue or nucleotide(s) residue relative to a reference sequence, such as a scaffold sequence.

As used herein, the term "domain" refers to a continuous or discontinuous sequence of amino acid residues. As used herein, the term "region" refers to a continuous sequence of amino acid residues.

Figure 1:
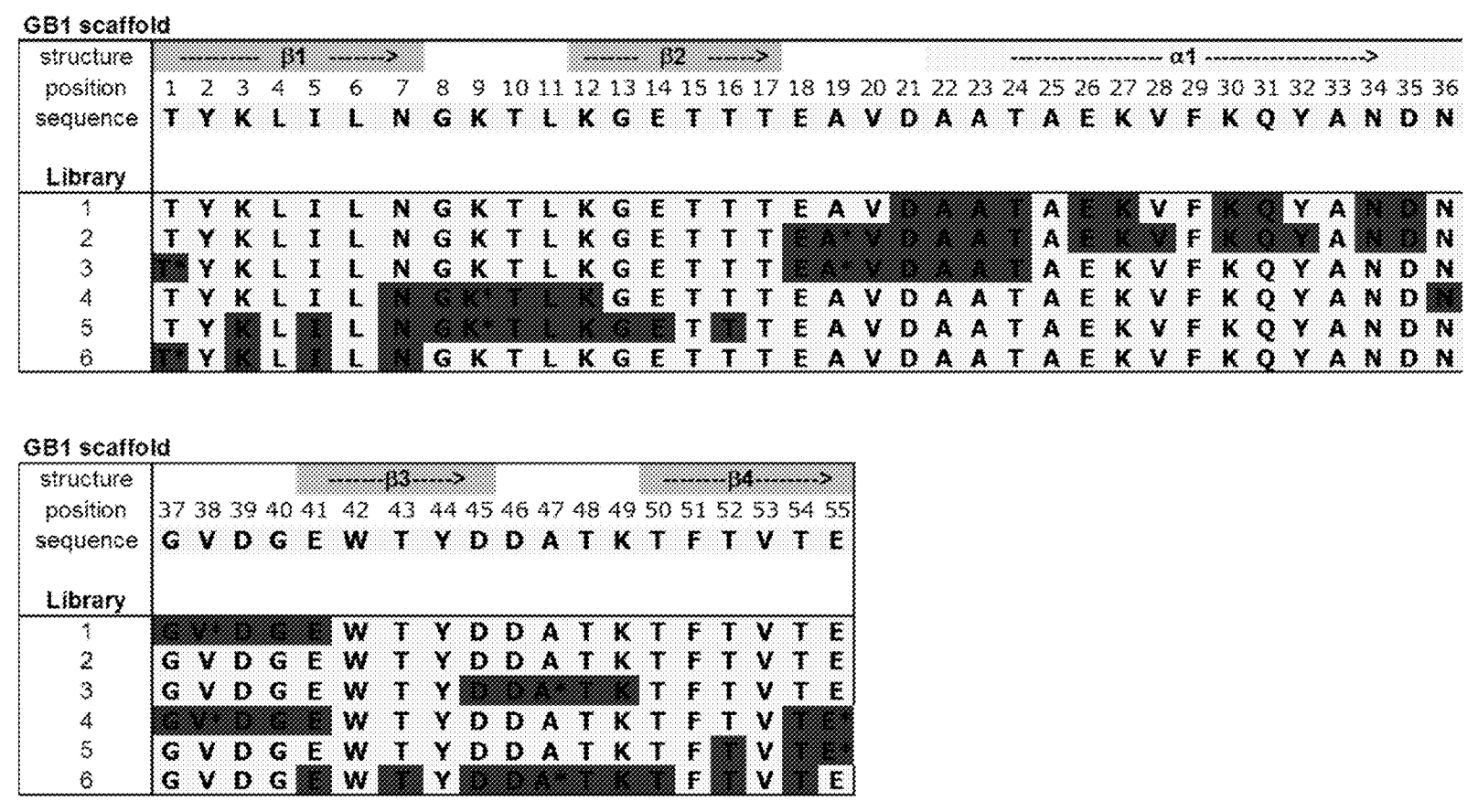

As used herein, the term "GB1 motif" and "4β-1α motif" are used interchangeably and refer to that part of the GB1 peptidic compounds corresponding to a GB1 scaffold domain of the same structural motif as the B1 domain of Protein G (GB1), where the structural motif of GB1 is characterized by a motif including a four stranded β-sheet packed against a helix (i.e., a 4β-1α motif). The arrangement of four β-strands and one α-helix may form a hairpin-helix-hairpin motif. An exemplary GB1 scaffold domain sequence is depicted in FIG. 1. GB1 scaffold domains include members of the family of IgG binding B domains, e,g, Protein L B1 domain. Amino acid sequences of exemplary B domains that may be employed herein as GB1 scaffold domains are found in the Wellcome Trust Sanger Institute Pfam database (The Pfam protein families database: Finn et al., Nucleic Acids Research (2010) Database Issue 38:D211-222), see, e.g., Family: IgG_binding_B (PF01378) (pfam.sanger.ac.uk/family/PF01378.10#tabview=tab0) or in NCBI's protein database. A GB1 scaffold domain may be a native sequence of a member of the B domain protein family, a B domain sequence with pre-existing amino acid sequence modifications (such as additions, deletions and/or substitutions), or a fragment or analogue thereof. A GB1 scaffold domain may be L-peptidic, D-peptidic or a combination thereof. In some cases, a "GB1 scaffold domain" may also be referred to as a "parent amino acid sequence."

In some embodiments, the GB1 scaffold domain is described by the following sequence: (T/S)Y(K/R)L(Z1)(Z1)(N/K)G(K/N/V/A)T(L/F)(K/S)GET(T/A/S)T(K/E)(A/T)(V/I)D(A/T/V)(A/E) (T/V)AE(K/Q)(A/E/T/V)F(K/R)(Q/D)YA(N/T)(A/D/E/K)N(G/N)(Z3)(D/T)G(E/V)W(A/T/S)YD(D/A/Y/T)ATKT(Z1)T(Z1)TE (SEQ ID NO:40), where each Z1 is independently a hydrophobic residue. In some embodiments, the GB1 scaffold domain is described by the following sequence: (T/S)Y(K/R)L(I/V)(L/I/V)(N/K)G(K/N/V/A)T(L/F)(K/S)GET(T/A/S)T(K/E)(A/T)(V/I)D(A/T/V) (A/E)(T/V)AE(K/Q)(A/E/T/V)F(K/R)(Q/D)YA(N/T)(A/D/E/K)N(G/N)(V/I)(D/T)G(E/V)W(A/T/S)YD(D/A/Y/T)ATKTFTVTE (SEQ ID NO:41). In certain embodiments, GB1 scaffold domain is described by the following sequence: TYKL(I/V)(L/I/V)(N/K)G(K/N)T(L/F)(K/S)GET(T/A)T(K/E)AVD(A/T/V)(A/E)TAE(K/Q)(A/E/T/V)F(K/R)QYA(N/T)(A/D/E/K)N(G/N)VDG(E/V)W(A/T/S)YD(D/A)ATKTFTVTE (SEQ ID NO:42). A mutation in a scaffold domain may include a deletion, insertion, or substitution of an amino acid residue at any convenient position to produce a sequence that is distinct from the reference scaffold domain sequence.

In some embodiments, the GB1 scaffold domain is described by the following sequence: T(Z2)K(Z1)(Z1)(Z1)(N/V)(G/L/I)(K/G)(Q/T/D)(L/A/R)(K/V)(G/E/V)(E/V)(A/T/R/I/P/V)(T/I)(R/W/L/K/V/T/I)E(A/L/I)VDA(A/G)(T/E)(A/V/F)EK(V/I/Y)(F/L/W/I/A)K(L/Q)(Z1)(Z3)N(A/D)(K/N)(T/G)(V/I)(E/D)G(V/E)(W/F)TY(D/K)D(E/A)(T/I)KT(Z1)T(Z1)TE (SEQ ID NO:43), where each Z1 is independently a hydrophobic residue, Z2 is an aromatic hydrophobic residue, and Z3 is a non-aromatic hydrophobic residue.

In some embodiments, the GB1 scaffold domain is described by the following sequence:

```
                                                          (SEQ ID NO: 44)
T(Y/F/W/A)K(L/V/I/M/F/Y/A)(L/V/I/F/M)(L/V/I/F/M/A/Y/S)(N/V)(G/L/I)(K/G)(Q/T/D)

(L/A/R)(K/V)(G/E/V)(E/V)(A/T/R/I/P/V)(T/I)(R/W/L/K/V/T/I)E(A/L/I)VDA(A/G)(T/E)

(A/V/F)EK(V/I/Y)(F/L/W/I/A)K(L/Q)(W/F/L/M/Y/I)(L/V/I/A)N(A/D)(K/N)(T/G)(V/I)

(E/D)G(V/E)(W/F)TY(D/K)D(E/A)(T/I)KT(L/V/I/F/M/W)T(L/V/I/F/M)TE.
```

As used herein, the term "GB1 peptidic compound" refers to a compound composed of peptidic residues that has a parent GB1 scaffold domain.

As used herein, the term "parent amino acid sequence" is a polypeptide comprising an amino acid sequence from which a variant peptidic compound arose and against which the variant peptidic compound is being compared. In some cases, the parent polypeptide lacks one or more of the mutations or modifications disclosed herein and differs in function compared to a variant peptidic compound as disclosed herein. The parent polypeptide may include a native scaffold domain sequence (e.g., a GB1 scaffold domain) with pre-existing amino acid sequence modifications (such as additions, deletions and/or substitutions).

As used herein, the term "variable region" refers to a continuous sequence of residues that includes one or more variant amino acids. A variable region may also include one or more conserved amino acids at fixed positions. As used herein, the term "fixed region" refers to a continuous sequence of residues that does not include any mutations or variant amino acids, and is conserved across a library of compounds.

As used herein, the term "variable domain" refers to a domain that includes all of the variant amino acids or mutations of a peptidic scaffold. The variable domain may include one or more variable regions, and may encompass a continuous or a discontinuous sequence of residues.

As used herein, the term "discontinuous sequence of residues" refers to a sequence of residues that is not continuous with respect to the primary sequence of a peptidic compound. A peptidic compound may fold to form a secondary or tertiary structure, e.g., a 4β-1α motif, where the amino acids of a discontinuous sequence of residues are adjacent to each other in space, i.e., contiguous. As used herein, the term "continuous sequence of residues" refers to a sequence of residues that is continuous in terms of the primary sequence of a peptidic compound.

As used herein, the term "non-core mutation" refers to an amino acid mutation of a peptidic scaffold that is located at a position in the structure that is not part of the hydrophobic core of the structure, i.e., is not located at a hydrophobic core residue position. Amino acid residues at hydrophobic core positions are not significantly solvent exposed but rather tend to form intramolecular hydrophobic contacts. Unless explicitly defined otherwise, the hydrophobic core residue positions of a GB1 scaffold, as described herein, are defined by the positions 2, 4, 6, 19, 25, 29, 33, 38, 42, 51 and 53 of the scaffold. One criteria used to specify hydrophobic core residues in a scaffold is described by Dahiyat et al., ("Probing the role of packing specificity in protein design," Proc. Natl. Acad. Sci. USA, 1997, 94, 10172-10177) where a PDB structure of the GB1 scaffold was used to calculate which side chains expose less than 10% of their surface area to solvent. Such methods and criteria can be modified for use with any convenient scaffold.

As used herein, the term "surface mutation" refers to an amino acid mutation in a peptidic scaffold that is located at a position in the structure that is solvent exposed. Such variant amino acid residues at surface positions are capable of interacting directly with a target protein, whether or not such an interaction occurs. Solvent exposed residues may be determined using a Protein Data Bank (PDB) structure (e.g., 3 GB1 for a GB1 scaffold) and by estimating the solvent accessible surface area (SASA) for each residue using the GETarea tool (Fraczkiewicz & Braun, "Exact and efficient analytical calculation of the accessible surface areas and their gradients for macromolecules," J. Comput. Chem. 1998, 19, 319-333). This tool calculates the ratio of SASA in structure compared to SASA in a random coil, where the solvent accessible residues were differentiated from buried residues using a ratio of 0.4. For example, the solvent exposed residues of an exemplary GB1 scaffold determined using this method are shown in bold below: TYKLILNGKTLKGETTTEAVDAA-TAEKVFKQYANDNGVDGEWTYDDATKTFTVTE (SEQ ID NO:1). These methods may be readily modified to identify solvent exposed residues in any convenient scaffold domain described herein.

As used herein, the term "boundary mutation" refers to an amino acid mutation of a peptidic scaffold that is located at a position in the structure that is at the boundary between the hydrophobic core and the solvent exposed surface. Such variant amino acid residues at boundary positions may be in part contacting hydrophobic core residues and/or in part solvent exposed and capable of some interaction with a target protein, whether or not such an interaction occurs.

Methods of classifying core, surface and boundary residues of a scaffold are described by Mayo et al. Nature Structural Biology, 5(6), 1998, 470-475 for the GB1 scaffold. Such methods may be modified for use with any convenient scaffold.

As used herein, the term "linking sequence" refers to a continuous sequence of amino acid residues, or analogs thereof, that connect two peptidic motifs. In certain embodiments, a linking sequence is the loop connecting two β-strands in a β-hairpin motif.

As used herein, the term "phage display" refers to a technique by which variant peptidic compounds are displayed as fusion proteins to a coat protein on the surface of phage, e.g. filamentous phage particles. The term "phagemid" refers to a plasmid vector having a bacterial origin of replication, e.g., ColE1, and a copy of an intergenic region of a bacteriophage. The phagemid may be based on any known bacteriophage, including filamentous bacteriophage. In some instances, the plasmid will also contain a selectable marker for antibiotic resistance. Segments of DNA cloned into these vectors can be propagated as plasmids. When cells harboring these vectors are provided with all genes necessary for the production of phage particles, the mode of replication of the plasmid changes to rolling circle replication to generate copies of one strand of the plasmid DNA and package phage particles. The phagemid may form infectious or non-infectious phage particles. This term includes phagemids which contain a phage coat protein gene or fragment thereof linked to a heterologous polypeptide gene as a gene fusion such that the heterologous polypeptide is displayed on the surface of the phage particle.

As used herein, the term "phage vector" refers to a double stranded replicative form of a bacteriophage that contains a heterologous gene and is capable of replication. The phage vector has a phage origin of replication allowing phage replication and phage particle formation. In some cases. the phage is a filamentous bacteriophage, such as an M13, f1, fd, Pf3 phage or a derivative thereof, a lambdoid phage, such as lambda, 21, phi80, phi81, 82, 424, 434, etc., or a derivative thereof, a Baculovirus or a derivative thereof, a T4 phage or a derivative thereof, a T7 phage virus or a derivative thereof.

As used herein, the term "a target protein" refers to all members of the target protein family, and fragments and protein mimics thereof, and enantiomers thereof. The target proteins of interest that are described herein are intended to include all members of the target family, and fragments and protein mimics thereof, and enantiomers thereof, unless explicitly described otherwise. The target protein may be any protein of interest, such as a therapeutic or diagnostic target. It is understood that when the biological activities and functions of a target protein in vivo are being described herein, that what is being referred to are the activities of the L-target proteins. The term "target protein" is intended to include L- and D-enantiomers. The term "target protein" is intended to include recombinant and synthetic molecules, which can be prepared using any convenient recombinant expression methods or using any convenient synthetic methods, or purchased commercially, as well as fusion proteins containing a target protein, as well as synthetic L- or D-proteins.

As used herein, the term "protein mimic" refers to a peptidic compound that functionally and/or structurally mimics a target protein or a portion or fragment thereof, or an enantiomer thereof. The protein mimic of a target protein may have a peptidic sequence (e.g., an epitope mimic) that is different from the target protein but may still substantially retain one or more biochemical properties of the target protein, such as a binding interaction to an antibody. It is understood that a protein mimic may be a mimic of a D-target protein or a L-target protein, and that although a D-peptidic protein mimic does not have the same biological functions or properties as the corresponding L-peptidic mimic, the mimics do have mirror image structures. In general terms, the target protein mimic includes an essential part of the original target protein structure (e.g., an epitope or arrangement of essential binding residues) that is necessary for forming a binding surface, such that the target protein mimic and the original target protein are each capable of binding specifically to a binding moiety of interest, e.g., an antibody or a D-peptidic compound. In some embodiments, the part(s) of the original target protein that is essential for binding is displayed on a scaffold such that the binding surface of the original target protein is mimicked. Any suitable scaffold for displaying the minimal essential part of the target protein may be used, including but not limited to antibody scaffolds, scFv, anticalins, non-antibody scaffolds, mimetics of protein secondary and tertiary structures, e.g a coiled coil. In some embodiments, a target protein mimic includes residues or fragments of the original target protein that are incorporated into a protein scaffold, where the scaffold mimics a structural motif of the target protein. For example, by incorporating residues of the target protein at desirable positions of a convenient scaffold, the protein mimic may present a potential binding surface that mimics that of the original target protein. In some embodiments, the native structure of the fragments of the original target protein are retained using methods of conformational constraint. Any convenient methods of conformationally constraining a peptidic compound may be used, such as but not limited to, bioconjugation, dimerization (e.g., via a linker), multimerization, or cyclization.

As used herein, the terms "linker", "linking group", "linkage" and "crosslink" are used interchangeably and refer to a linking moiety that connects two groups and has a backbone of 40 atoms or less (such as 30 atoms or less) in length. A linking moiety may be a covalent bond that connects two groups or a chain of between 1 and 40 atoms in length, for example of about 1, 2, 3, 4, 5, 6, 8, 10, 12, 14, 16, 18, 20 or 30 carbon atoms in length, where the linker may be linear, branched, cyclic or a single atom. In certain cases, one, two, three, four or five or more carbon atoms of a linker backbone may be optionally substituted with a sulfur, nitrogen or oxygen heteroatom. The bonds between backbone atoms may be saturated or unsaturated, usually not more than one, two, or three unsaturated bonds will be present in a linker backbone. The linker may include one or more substituent groups, for example an alkyl, aryl or alkenyl group. A linker may include, without limitations, oligo(ethylene glycol), ethers, thioethers, amides, tertiary amines, alkyls, which may be straight or branched, e.g., methyl, ethyl, n-propyl, 1-methylethyl (isopropyl), n-butyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone. A linker may include a single amino acid residue or a peptidic sequence of two or more residues, such as 2, 3, 4, 5, 6, 7, 8, 9 or 10 residues. A linker may be cleavable or non-cleavable.

As used herein, the term "affinity tag" refers to a member of a specific binding pair, i.e. two molecules where one of the molecules through chemical or physical means specifically binds to the other molecule. The complementary member of the affinity tag may be immobilized (e.g., to a chromatography support, a bead or a planar surface) to produce an affinity chromatography support that specifically binds the affinity tag. Tagging a compound of interest with an affinity tag allows the compound to be separated from a mixture of untagged compounds by affinity, e.g., using affinity chromatography. Examples of specific binding pairs include biotin and streptavidin (or avidin), and antigen and antibody, although binding pairs, e.g., nucleic acid hybrids, polyhistidine and nickel, and azido and alkynyl (e.g., cyclooctynyl) or phosphino groups are also envisioned. The specific binding pairs may include analogs, derivatives, fragments and mimics of the original specific binding members.

As used herein, the term "biotin moiety" refers to an affinity tag that includes biotin or a biotin analogue such as desthiobiotin, oxybiotin, 2'-iminobiotin, diaminobiotin, biotin sulfoxide, biocytin, etc. Biotin moieties bind to streptavidin with an affinity of at least $10^{-8}$M. A biotin moiety may also include a linker, e.g., -LC-biotin, -LC-LC-biotin, -SLC-biotin or -PEG$_n$-biotin where n is 3-12 (commercially available from Pierce Biotechnology).

The molecules of the subject methods may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids and polypeptides. The present invention is meant to include all such possible isomers, as well as, their racemic and optically pure forms. When the molecules described herein contain olefinic double bonds or other centers of geometric asymmetry, and unless specified otherwise, it is intended that the molecules include both E and Z geometric isomers. Likewise, all tautomeric forms are also intended to be included.

As used herein, a "vaccine" is an immunogenic preparation that is used to induce an immune response in individuals. A vaccine can have more than one constituent that is immunogenic. A vaccine can be used for prophylactic and/or therapeutic purposes. A vaccine does not necessarily have to prevent viral infections. Without being bound by theory, the vaccines of the invention can affect an individual's immune response in a manner such that viral infection occurs in a lesser amount (including not at all) or such that biological or physiological effects of the viral infection are ameliorated when the vaccine is administered as described herein.

As used herein, the term "epitope" refers to a molecule (or association of molecules), containing a region capable of eliciting an immune response and/or containing a region capable of specific binding with an antibody. An epitope may be selected, for example, from a portion of a protein not previously known to bind specifically to an antibody.

"Specific binding" refers to binding with a dissociation constant of no greater than about $10^{-6}$ M, preferably no greater than about $10^{-7}$ M, more preferably no greater than about $10^{-8}$ M, still more preferably no greater than about $10^{-9}$M, yet more preferably no greater than about $10^{-10}$ M, or alternatively with affinity of at least about $10^6$ M, preferably at least about $10^7$ M, more preferably at least about $10^8$ M, still more preferably at least about $10^9$ M, yet more preferably at least about $10^{10}$ M.

An "effective amount" or a "sufficient amount" of a substance is that amount sufficient to cause a desired biological effect, such as beneficial results, including clinical results, and, as such, an "effective amount" depends upon the context in which it is being applied. In the context of this invention, an example of an effective amount of a vaccine is an amount sufficient to induce an immune response (e.g., antibody production) in an individual. An effective amount can be administered in one or more administrations.

"Stimulation" or "induction" of an immune response can include both humoral and/or cellular immune responses. In one aspect, it refers to an increase in the response, which can arise from eliciting and/or enhancement of a response as compared to the immune response when no vaccine is given at all.

As used herein, the term "neutralizing" refers to a moiety that is capable of preventing or inhibiting virus infection in a sample. The viral infection is reduced and in some cases, inhibited. Reduction of viral infection can be at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99% or 100% from the amount of infection that would have occurred had the moiety not been present in the sample. In some cases, the sample is a subject. Any convenient assays for viral infection may be utilized. In some instances, a neutralizing moiety is capable of reducing or inhibiting viral replication. Reduction of viral replication can be at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99% or 100% from the amount of replication that would have occurred had the moiety not been present in the sample. Any convenient assays for viral replication may be utilized.

As used herein, the term "broad spectrum" refers to the anti-viral activity of a single moiety (e.g., an antibody or compound) that is active against two or more different viruses, such as three or more, four or more, five or more, six or more, eight or more, 10 or more different viruses. The two or more different viruses may be selected from different virus sub-groups (e.g., Influenza A group 1 or Influenza A group 2), or may be selected from within the same group (e.g., two or more of H1, H2, H5, H6, H8 and H9 group 1 influenza A viruses, or two or more of H3, H4, H7 and H10 Group 2 Influenza A viruses).

DETAILED DESCRIPTION

GB1 peptidic compounds that specifically bind to a hemagglutinin target protein, and libraries that include the same, as well as methods of making and using the same, are provided. Also provided are methods and compositions for making and using the compounds. Aspects of the invention include methods of screening libraries of L-peptidic compounds for specific binding to a D-peptidic hemagglutinin (HA) target protein. Once a L-peptidic compound has been identified that specifically binds to the D-peptidic hemagglutinin target protein, the D-enantiomer of the selected L-peptidic compound may be produced. In some embodiments, the D-enantiomer of the selected L-peptidic compound binds to, and in some instances, neutralizes influenza virus particles.

L-peptidic HA target proteins that find use in vaccines are also provided. The HA target proteins (e.g., HA coiled coil mimics) may be conjugated to a carrier to produce a HA mimic conjugate. Also provided are methods and compositions for making and using the conjugates, including methods of inducing an antibody response in a subject.

Before certain embodiments are described in greater detail, it is to be understood that this invention is not limited to certain embodiments described, as such may, of course, vary. It is also to be understood that the terminology used herein is for the purpose of describing certain embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Compounds

As summarized above, aspects of the invention include GB1 peptidic compounds that specifically bind to a hemagglutinin target protein. In some cases, the GB1 peptidic compounds are D-peptidic compounds that specifically bind to a L-peptidic hemagglutinin target protein. In other cases, the hemagglutinin target protein is D-peptidic and the compound is L-peptidic. Also provided are libraries of GB1 peptidic compounds.

The subject GB1 peptidic compounds have a GB1 scaffold domain of the same structural motif as the B1 domain of Protein G (GB1), where the structural motif of GB1 is characterized by a motif that includes an arrangement of four β-strands and one α-helix (also referred to as a 4β-1α motif) around a hydrophobic core. The subject GB1 peptidic compounds include mutations at various non-core positions of the 4β-1α motif, e.g., variant amino acids at non-core positions within a GB1 scaffold domain. In many embodiments, the four β-strands and one α-helix motifs of the structure are arranged in a hairpin-helix-hairpin motif, e.g., β1-β2-α1-β3-β4 where β1-β4 are β-strand motifs and α1 is a helix motif.

The positions to be mutated are selected to minimize structural perturbations of the GB1 scaffold domain and to ensure that the subject GB1 peptidic compounds can maintain a folded state under physiological conditions. Another aspect of the subject compounds is the selection of amino acid positions to be mutated such that the amino acids can form a potential binding surface in the GB1 scaffold domain, whether or not the residues actually contact a target protein. One way of determining whether an amino acid position is part of a potential binding surface involves examining the three dimensional structure of the GB1 scaffold domain, using a computer program such as the UCSF Chimera program. Other ways include crystallographic and genetic mutational analysis. Any convenient method may be used to determine whether an amino acid position is part of a potential binding surface.

The mutations of the parent GB1 domain may be concentrated at one of several different potential binding surfaces of the scaffold domain. Several distinct arrangements of mutations of the GB1 scaffold domain at non-core positions of the hairpin-helix-hairpin scaffold domain are provided. The majority of the mutations are at non-core positions of the parent GB1 domain (e.g., solvent exposed or boundary positions) however in some cases one or more mutations (e.g., 1 or 2 mutations) may be located at hydrophobic core positions. In certain embodiments, mutations at hydrophobic core positions may be tolerated without significantly disrupting the GB1 scaffold structure, such as, when those core mutations are selected in a loop region. In certain embodiments, mutations at boundary positions may also be tolerated without significantly disrupting the GB1 scaffold structure. In such cases the loop region may form a structure or conformation that is different to that of the parent GB1 scaffold. Mutations at such positions may confer desirable properties upon the resulting GB1 compounds, such as stability, a certain structural property, or specific binding to a target molecule.

In some embodiments, the sequence of the GB1 scaffold domain is optimized for stability. In some embodiments, mutations at hydrophobic core and/or boundary positions are included to optimize the stability of a GB1 peptidic structure. In some cases, optimization of the stability is performed when the GB1 structure is disrupted by mutations at a target protein-binding surface. For example, one or more mutations in the variable domain of a GB1 peptidic compound that provide for specific binding to a hemagglutinin target protein may lead to disruption of the hydrophobic core structure of the compound. In such cases, one or more further mutations may be introduced, or optimization of the underlying scaffold sequence may be performed, to optimize stability and minimize any disruptions to the structure and produce a stable GB1 peptidic compound that specifically binds to the hemagglutinin target protein. In certain embodiments, the one or more stabilizing mutations may include mutations to hydrophobic core and/or boundary residues, and may be located in a fixed domain or a variable domain of the structure.

The positions of the mutations in the parent GB1 domain may be described herein either by reference to a structural motif or region, or by reference to a position number in the primary sequence of the domain. FIG. 1 illustrates the alignment of the position numbering scheme for a GB1 scaffold domain relative to its β1, β2, α1, β3 and β4 motifs, and relative to the positions of mutations found in certain subject compounds. Positions marked with an asterix indicate exemplary positions at which mutations that include the insertion of one or more amino acids may be included. Any GB1 peptidic domain sequence may be substituted for the GB1 scaffold sequence depicted in FIG. 1, and the positions of the mutations that define a subject compound may be transferred from one scaffold to another by any convenient method. For example, a sequence alignment method may be used to place any GB1 scaffold domain sequence within the framework of the position numbering scheme illustrated in FIG. 1. Alignment methods based on structural motifs such as β-strands and α-helices may also be used to place a GB1 scaffold domain sequence within the framework of the position numbering scheme illustrated in FIG. 1.

In some cases, a first GB1 scaffold domain sequence may be aligned with a second GB1 scaffold domain sequence that is one or more amino acids longer or shorter. For example, the second GB1 scaffold domain may have one or more additional amino acids at the N-terminal or C-terminal relative to the first GB1 scaffold, or may have one or more additional amino acids in one of the loop regions of the structure. In such cases, a numbering scheme such as is described below for insertion mutations may be used to relate two GB1 scaffold domain sequences.

A subject GB1 peptidic compound may include a hairpin-helix-hairpin domain described by formula (I):

$$P1\text{-}\alpha1\text{-}P2 \qquad (I)$$

where P1 and P2 are independently beta-hairpin domains and α1 is a helix domain and P1, α1 and P2 are connected independently by linking sequences of between 1 and 10 residues in length. In some embodiments, in formula (I), P1 is β1-β2 and P2 is β3-β4 such that the compound is described by formula (II):

$$\beta1\text{-}\beta2\text{-}\alpha1\text{-}\beta3\text{-}\beta4 \qquad (II)$$

where β1, β2, β3 and β4 are independently beta-strand domains and α1 is a helix domain, and β1, β2, α1, β3 and β4 are connected independently by linking sequences of between 1 and 10 residues in length, such as, between 2 and 8 residues, or between 3 and 6 residues in length. In certain embodiments, each linking sequence is independently of 3, 4, 5, 6, 7 or 8 residues in length. In certain embodiments, each linking sequence is independently of 3, 4, 5, 6, 7 or 8 residues in length, such as 4 or 5 residues in length.

In certain embodiments, the linking sequences may form a loop or a turn structure. For example, the two antiparallel β-strands of a hairpin motif may be connected via a loop. Mutations in a linking sequence that includes insertion or deletion of one or more amino acid residues may be tolerated without significantly disrupting the GB1 scaffold domain structure. In some embodiments, in formulas (I) and (II), the subject compound includes mutations in one or more linking sequences. In certain embodiments, 80% or more, 90% or more, 95% or more, or even 100% of the mutations are at positions within the regions of the linking sequences. In certain embodiments, in formulas (I) and (II), at least one of the linking sequences is one or more (e.g., such as 2 or more) residues longer in length than the corresponding linking sequence of the GB1 scaffold domain. In certain embodiments, in formulas (I) and (II), at least one of the linking sequences is one or more residues shorter in length than the corresponding linking sequence of the GB1 scaffold domain.

In some embodiments, one or more positions in the scaffold may be selected as positions at which to include insertion mutations, e.g., mutations that include the insertion of 1 or 2 additional amino acid residues in addition to the amino acid residue being substituted. In certain embodiments, the insertion mutations are selected for inclusion in one or more loop regions, or at the N-terminal or C-terminal of the scaffold. The positions of the variant amino acids that are inserted may be referred to using a letter designation with respect to the numbered position of the mutation, e.g., an insertion mutation of 2 amino acids at position 38 may be referred to as positions 38a and 38b.

In certain embodiments, the subject compound includes a mutation at position 38 that includes insertion of 0, 1 or 2 variant amino acids. In certain embodiments, the subject compound includes a mutation at position 19 that includes insertion of 0, 1 or 2 variant amino acids. In certain embodiments, the subject compound includes a mutation at position 1 that include insertion of 2 variant amino acids, and at positions 19 and 47 that each include insertion of 0, 1 or 2 variant amino acids. In certain embodiments, the subject compound includes mutations at positions 9 and 38 that each include insertion of 0, 1 or 2 variant amino acids, and at position 55 that includes insertion of 1 variant amino acid. In certain embodiments, the subject compound includes a mutation at position 9 that includes insertion of 0, 1 or 2 variant amino acids, and at position 55 that includes insertion of 1 variant amino acid. In certain embodiments, the subject compound includes a mutation at position 1 that includes insertion of 1 variant amino acid, and at position 47 that includes insertion of 0, 1 or 2 variant amino acids.

In some cases, when an insertion mutation (e.g., insertion of one or more additional variant amino acids) is made in a GB1 scaffold, the resulting GB1 compound variants may be aligned with the parent GB1 scaffold in different ways. For example, an insertion mutation including 2 additional variant amino acids at position 38 of the GB1 scaffold may lead to GB1 compound variants where the loop regions between the cd and P3 regions can be aligned with the GB1 scaffold domain in two or more distinct ways. In other words, the resulting GB1 compounds may encompass various distinct loop sequences and/or structures that align differently with the parent GB1 scaffold domain. In some cases, the various distinct loop sequences are produced when the insertion mutation is in a variable loop region (e.g. where most of the loop region is being mutated).

In some embodiments, the subject compound includes 4 or more, such as, 5 or more, 6 or more, 7 or more, 8 or more, 9 or more, 10 or more, 11 or more, 12 or more, 13 or more, 14 or more, or 15 or more mutations at different positions of the hairpin-helix-hairpin domain. The mutations may involve the deletion, insertion, or substitution of the amino acid residue at the position being mutated. The mutations may include substitution with any naturally or non-naturally occurring amino acid, or an analog thereof.

In some embodiments, the subject compound includes 3 or more different non-core mutations, such as, 4 or more, 5 or more, 6 or more, 7 or more, 8 or more, 9 or more, 10 or more, 11 or more, or 12 or more different non-core mutations in a region outside of the β1-β2 region.

In some embodiments, the subject compound includes 3 or more different non-core mutations, such as, 4 or more, 5 or more, 6 or more, 7 or more, 8 or more, 9 or more, 10 or more or 11 or more different non-core mutations in the α1 region.

In some embodiments, the subject compound includes 3 or more different non-core mutations, such as 4 or more, 5 or more, 6 or more, 7 or more, 8 or more, 9 or more or 10 or more different non-core mutations in the β3-β4 region.

In some embodiments, the subject compound includes at least 5 or more different non-core mutations, such as 6 or more, 7 or more, 8 or more, 9 or more, 10 or more, 11 or more, or 12 or more different non-core mutations in the α1-β3 region.

In certain embodiments, the subject compound includes ten or more different mutations, where the ten or more different mutations are located at positions selected from the group consisting of positions 21-24, 26, 27, 30, 31, 34, 35, 37-41. In certain embodiments, one or more mutations (e.g., 1 or 2 mutations) are at core positions. In certain embodiments, one or more mutations (e.g., 1 or 2 mutations) are at boundary positions. In certain embodiments, ten or more mutations (e.g., 10, 11, 12, 13 or more mutations) are at solvent exposed positions.

In certain embodiments, the subject compound includes ten or more different mutations, where the ten or more different mutations are located at positions selected from the group consisting of positions 18-24, 26-28, 30-32, 34 and 35. In certain embodiments, one or more mutations (e.g., 1 mutation) are at core positions. In certain embodiments, ten or more mutations (e.g., 10, 11, 12, 13, 14 or more mutations) are at solvent exposed positions.

In certain embodiments, the subject compound includes ten or more different mutations, where the ten or more different mutations are located at positions selected from the group consisting of positions 1, 18-24 and 45-49. In certain embodiments, one or more mutations (e.g., 1 mutation) are at core positions. In certain embodiments, ten or more mutations (e.g., 10, 11, 12 or more mutations) are at solvent exposed positions.

In certain embodiments, the subject compound includes ten or more different mutations, where the ten or more different mutations are located at positions selected from the group consisting of positions 7-12, 36-41, 54 and 55. In certain embodiments, one or more mutations (e.g., 1 mutation) are at core positions. In certain embodiments, one or more mutations (e.g., 2, 3 or 4 or more mutations) are at boundary positions. In certain embodiments, five or more mutations (e.g., 6, 7, 8, 9 or more mutations) are at solvent exposed positions.

In certain embodiments, the subject compound includes ten or more different mutations, where the ten or more different mutations are located at positions selected from the group consisting of positions 3, 5, 7-14, 16, 52, 54 and 55. In certain embodiments, one or more mutations (e.g., 2, 3 or more mutations) are at boundary positions. In certain embodiments, nine or more mutations (e.g., 10, 11, 12 or more mutations) are at solvent exposed positions.

In certain embodiments, the subject compound includes ten or more different mutations, where the ten or more different mutations are located at positions selected from the group consisting of positions 1, 3, 5, 7, 41, 43, 45-50 52 and 54. In certain embodiments, one or more mutations (e.g., 2 or more mutations) are at boundary positions. In certain embodiments, nine or more mutations (e.g., 10, 11, 12 or more mutations) are at solvent exposed positions.

In certain embodiments, the subject compound includes five or more different mutations in the α1 region. In certain embodiments, five or more different mutations are located at positions selected from the group consisting of positions 22-24, 26, 27, 30, 31, 34 and 35.

In certain embodiments, the subject compound includes ten or more different mutations in the α1 region. In certain embodiments, the ten or more different mutations are located at positions selected from the group consisting of positions 22-24, 26, 27, 28, 30, 31, 32, 34 and 35.

In certain embodiments, the subject compound includes three or more different mutations in the β3-β4 region. In certain embodiments, the three or more different mutations are located at positions selected from the group consisting of positions 41, 54 and 55. In certain embodiments, the three or more different mutations are located at positions selected from the group consisting of positions 52, 54 and 55.

In certain embodiments, the subject compound includes five or more different mutations in the β3-β4 region. In certain embodiments, the five or more different mutations are located at positions selected from the group consisting of positions 45-49.

In certain embodiments, the subject compound includes nine or more different mutations in the β3-β4 region. In certain embodiments, the nine or more different mutations are located at positions selected from the group consisting of positions 41, 43, 45-50 52 and 54.

In certain embodiments, the subject compound includes two or more different mutations in the region between the α1 and β3 regions, e.g., mutations in the linking sequence between α1 and β3. In certain embodiments, the two or more different mutations are located at positions selected from the group consisting of positions 37-40.

In certain embodiments, the subject compound includes three or more, four or more, five or more, six or more, or ten or more different mutations in the β1-β2 region. In certain embodiments, the ten or more different mutations in the β1-β2 region are located at positions selected from the group consisting of positions 3, 5, 7-14 and 16.

In some embodiments, the subject compound is described by a formula independently selected from the group consisting of:

F1-V1-F2  (III);

F3-V2-F4  (IV);

V3-F5-V4-F6-V5-F7  (V);

F8-V6-F9-V7-F10-V8  (VI);

V9-F11-V10  (VII); and

V11-F12-V12  (VIII)

where F1, F2, F3, F4, F5, F6, F7, F8, F9, F10, F11 and F12 are fixed regions and V1, V2, V3, V4, V5, V6, V7, V8, V9, V10, V11 and V12 are variable regions;

where the variable regions of any one formula include a combined total of three or more different non-core mutations in a region outside of the β1-β2 region.

In certain embodiments, the subject compound is described by formula (III), where:

F1 comprises a sequence having 60% or more (e.g., 70% or more, 80% or more, 90% or more, or 95% or more) amino acid sequence identity to the amino acid sequence TYKLIL-NGKTLKGETTTEA (SEQ ID NO:2);

F2 comprises a sequence having 60% or more (e.g., 70% or more, 80% or more, 90% or more, or 95% or more) amino acid sequence identity to an amino acid sequence TYDDAT-KTFTVTE (SEQ ID NO:3); and V1 comprises a sequence that comprises 10 or more mutations (e.g., 11, 12, 13, 14 or 15 or more mutations) compared to the parent amino acid sequence VDAA-TAEKVFKQYANDNGVDGEW (SEQ ID NO:4).

In certain embodiments, in formula (III), V1 comprises a sequence of the following formula: VXXXXXAXX-VFXXYAXXNXXXXXW (SEQ ID NO:140), where each X is a variant amino acid.

In certain embodiments, in formula (III), F1 comprises the sequence TYKLILNGKTLKGETTTEA (SEQ ID NO:2), F2 comprises the sequence TYDDATKTFTVTE (SEQ ID NO:3), and V1 comprises a sequence of the following formula: VXXXXXAXXVFXXYAXXNXXXXXW (SEQ ID NO:141) where each X is independently selected from the group consisting of A, D, F, S, V and Y.

In certain embodiments, in formula (III), the mutation at position 19 in V1 includes insertion of 0, 1 or 2 variant amino acids.

In certain embodiments, the subject compound is described by formula (IV), where:

F3 comprises a sequence having 60% or more (e.g., 70% or more, 80% or more, 90% or more, or 95% or more) amino acid sequence identity to the amino acid sequence TYKLIL-NGKTLKGETT (SEQ ID NO:142);

F4 comprises a sequence having 60% or more (e.g., 70% or more, 80% or more, 90% or more, or 95% or more) amino acid sequence identity to an amino acid sequence GVDGEW-TYDDATKTFTVTE (SEQ ID NO:143); and V2 comprises a sequence that comprises 10 or more mutations (e.g., 11, 12, 13, 14 or 15 or more mutations) compared to the parent amino acid sequence TEAVDAA-TAEKVFKQYANDN (SEQ ID NO:144).

In certain embodiments, in formula (IV), V2 comprises a sequence of the formula: TXXXXXXXAXXXFXXXAXXN (SEQ ID NO:145), where each X is a variant acid.

In certain embodiments, in formula (IV), F3 comprises the sequence TYKLILNGKTLKGETT (SEQ ID NO:142), F4 comprises the sequence GVDGEWTYDDATKTFTVTE (SEQ ID NO:143), and V2 comprises a sequence of the formula: TXXXXXXXAXXXFXXXAXXN (SEQ ID NO:146) where each X is independently selected from the group consisting of A, D, F, S, V and Y.

In certain embodiments, in formula (IV), the mutation at position 3 of V2 includes insertion of 0, 1 or 2 variant amino acids.

In certain embodiments, the subject compound is described by formula (V), where:

F5 comprises a sequence having 60% or more (e.g., 70% or more, 80% or more, 90% or more, or 95% or more) amino acid sequence identity to the amino acid sequence KLIL-NGKTLKGETT (SEQ ID NO:147);

F6 comprises a sequence having 60% or more (e.g., 70% or more, 80% or more, 90% or more, or 95% or more) amino acid sequence identity to an amino acid sequence EKVFKQYANDNGVDGEWT (SEQ ID NO:148);

F7 comprises a sequence having 60% or more (e.g., 70% or more, 80% or more, 90% or more, or 95% or more) amino acid sequence identity to an amino acid sequence FTVTE (SEQ ID NO:149);

V3 comprises a sequence that comprises one or more mutations (e.g., 2 or more mutations) compared to the parent amino acid sequence TY; and V4 comprises a sequence that comprises 3 or more mutations (e.g., 4, 5, 6 or 7 or more mutations) compared to the parent amino acid sequence TEAVDAATA (SEQ ID NO:150); and V5 comprises a sequence that comprises 3 or more mutations (e.g., 4 or 5 or more mutations) compared to the parent amino acid sequence YDDATKT (SEQ ID NO:151).

In certain embodiments, in formula (V), V3 comprises a sequence of the formula XY, V4 comprises a sequence of the formula TXXXXXXXA (SEQ ID NO:152), and V5 comprises a sequence of the formula YXXXXXT (SEQ ID NO:153) where each X is a variant amino acid.

In certain embodiments, in formula (V), F5 comprises the sequence KLILNGKTLKGETT (SEQ ID NO:147), F6 comprises the sequence EKVFKQYANDNGVDGEWT (SEQ ID NO:148), F7 comprises the sequence FTVTE (SEQ ID NO:149), V3 comprises a sequence of the formula XY, V4 comprises a sequence of the formula TXXXXXXXA (SEQ ID NO:154), and V5 comprises a sequence of the formula YXXXXXT (SEQ ID NO:155) where each X is independently selected from the group consisting of A, D, F, S, V and Y.

In certain embodiments, in formula (V), the mutation at position 1 of V3 includes insertion of +2 variant amino acids, and the mutations at positions 3 and 4 of V4 and V5, respectively, each include insertion of 0, 1 or 2 variant amino acids.

In certain embodiments, the subject compound is described by formula (VI), where:

F8 comprises a sequence having 60% or more (e.g., 70% or more, 80% or more, 90% or more, or 95% or more) amino acid sequence identity to the amino acid sequence TYKLI (SEQ ID NO:156);

F9 comprises a sequence having 60% or more (e.g., 70% or more, 80% or more, 90% or more, or 95% or more) amino acid sequence identity to the amino acid sequence ETTTEAVDAATAEKVFKQYAN (SEQ ID NO:157);

F10 comprises a sequence having 60% or more (e.g., 70% or more, 80% or more, 90% or more, or 95% or more) amino acid sequence identity to the amino acid sequence TYDDATKTFT (SEQ ID NO:158);

V6 comprises a sequence that comprises 3 or more mutations (e.g., 4, 5 or 6 or more mutations) compared to the parent amino acid sequence LNGKTLKG (SEQ ID NO:159);

V7 comprises a sequence that comprises 3 or more mutations (e.g., 4, 5 or 6 or more mutations) compared to the parent amino acid sequence DNGVDGEW (SEQ ID NO:160);

V8 comprises a sequence that comprises one or more mutations (e.g., 2 or more mutations) compared to the parent amino acid sequence VTE.

In certain embodiments, in formula (VI), V6 comprises a sequence of the formula LXXXXXXG (SEQ ID NO:161), V7 comprises a sequence of the formula DXXXXXXW (SEQ ID NO:162), and V8 comprises a sequence of the formula VXX where each X is a variant amino acid.

In certain embodiments, in formula (VI), F8 comprises the sequence TYKLI (SEQ ID NO:156), F9 comprises the sequence ETTTEAVDAATAEKVFKQYAN (SEQ ID NO:157), F10 comprises the sequence TYDDATKTFT (SEQ ID NO:158), V6 comprises a sequence of the formula LXXXXXXG (SEQ ID NO:163), V7 comprises a sequence of the formula DXXXXXXW (SEQ ID NO:164), and V8 comprises a sequence of the formula VXX where each X is independently selected from the group consisting of A, D, F, S, V and Y.

In certain embodiments, in formula (VI), the mutations at position 4 of V6 and V7 each include insertion of 0, 1 or 2 variant amino acids, and the mutation at position 3 of V8 includes insertion of 1 variant amino acid.

In certain embodiments, the subject compound is described by formula (VII), where:

F11 comprises a sequence having 60% or more (e.g., 70% or more, 80% or more, 90% or more, or 95% or more) amino acid sequence identity to an amino acid sequence EAVDAATAEKVFKQYANDNGVDGEWTYDDATKT (SEQ ID NO:165);

V9 comprises a sequence that comprises 6 or more mutations (e.g., 7, 8, 9, 10 or 11 or more mutations) compared to the parent amino acid sequence TYKLILNGKTLKGETTT (SEQ ID NO:166; and V10 comprises a sequence that comprises 2 or more mutations (e.g., 3 or more mutations) compared to the parent amino acid sequence FTVTE (SEQ ID NO:167).

In certain embodiments, in formula (VII), V9 comprises a sequence of the formula TYXLXLXXXXXXXXXTXT (SEQ ID NO:168), and V10 comprises a sequence of the formula FXVXX (SEQ ID NO:169), where each X is a variant amino acid.

In certain embodiments, in formula (VII), F11 comprises the sequence EAVDAATAEKVFKQYANDNGVDGEWTYDDATKT (SEQ ID NO:165); V9 comprises a sequence of the formula TYXLXLXXXXXXXXXTXT (SEQ ID NO:170), and V10 comprises a sequence of the formula FXVXX (SEQ ID NO:171), where each X is independently selected from the group consisting of A, D, F, S, V and Y.

In certain embodiments, in formula (VII), the mutation at position 9 of V9 includes insertion of 0, 1 or 2 variant amino acids, and the mutation at position 5 of V10 includes insertion of 1 variant amino acid.

In certain embodiments, the subject compound is described by formula (VIII), where:

F12 comprises a sequence having 60% or more (e.g., 70% or more, 80% or more, 90% or more, or 95% or more) amino acid sequence identity to the amino acid sequence KTLKGETTTEAVDAATAEKVFKQYANDNGVD (SEQ ID NO:172);

V11 comprises a sequence that comprises 3 or more mutations (e.g., 4 or more mutations) compared to the parent amino acid sequence TYKLILNG (SEQ ID NO:173);

V12 comprises a sequence that comprises 5 or more mutations (e.g., 6, 7, 8, 9 or 10 or more mutations) compared to the parent amino acid sequence GEWTYDDATKTFTVTE (SEQ ID NO:174).

In certain embodiments, in formula (VIII), V11 comprises a sequence of the formula XYXLXLXG (SEQ ID NO:175), and V12 comprises a sequence of the formula GXWXYXXXXXXXFXVXE (SEQ ID NO:176), where each X is a variant amino acid.

In certain embodiments, in formula (VIII), F12 comprises the sequence KTLKGETTTEAVDAATAEKVFKQYANDNGVD (SEQ ID NO:172), V11 comprises a sequence of the formula XYXLXLXG (SEQ ID NO:177), and V12 comprises a sequence of the formula GXWXYXXXXXXXFXVXE (SEQ ID NO:178), where each X is independently selected from the group consisting of A, D, F, S, V and Y.

In certain embodiments, in formula (VIII), the mutation at position 8 of V12 includes insertion of 0, 1 or 2 variant amino acids, and the mutation at position 1 of V11 includes insertion of 2 variant amino acids.

In some embodiments, the compound includes a peptidic sequence of between 30 and 100 residues, such as between 50 and 100, between 30 and 90, between 50 and 90, between 60 and 90, between 30 and 80, between, between 40 and 80, between 50 and 80, between 40 and 70, between 45 and 60 residues, or between 50 and 56 residues. In certain embodiments, the compound includes a GB1 motif having a peptidic sequence of 50, 51, 52, 53, 54, 55, 56, 57, 58, 59 or 60 residues. In certain embodiments, the peptidic sequence is of 54, 55, 56 or 57 residues, such as 55 or 56 residues. In certain embodiments, the compound includes a peptidic sequence of 55 or more residues, such as 60 or more residues, 65 or more residues, 70 or more residues, 75 or more residues, 80 or more residues, 90 or more residues, or even 100 or more residues.

In some embodiments, the subject compound includes a GB1 scaffold domain and a variable domain. The variable domain may be a part of the GB1 scaffold domain and may be either a continuous or a discontinuous sequence of residues. A variable domain that is defined by a discontinuous sequence of residues may include contiguous variant amino acids at positions that are arranged close in space relative to each other in the structure of the compound. The variable domain may form a potential binding interface of the subject compound. The variable domain may define a binding surface area of a suitable size for forming protein-protein interactions of high affinity (e.g., 300 nM or less, such as 100 nM or less, 30 nM or less, 10 nM or less, 3 nM or less, or 1 nM or less) and specificity. The variable domain may include a surface area of between 600 and 1800 Å$^2$, such as between 800 and 1600 Å$^2$, between 1000 and 1400 Å$^2$, between 1100 and 1300 Å$^2$, or about 1200 Å$^2$.

The individual sequences of the subject compounds can be determined as follows. Any GB1 scaffold as defined herein may be selected as a scaffold for a subject compound. The positions of the mutations in the GB1 scaffold domain may be selected as described herein, e.g., as depicted in FIG. 1 for surfaces 1 to 6, where the GB1 scaffold domain may be aligned with the framework of FIG. 1 as described above. The nature of the mutation at each variant amino acid position may be selected, e.g., substitution with any naturally occurring or non naturally occurring amino acid and may confer on the compound variant a desirable property (e.g., increased solubility, stability or specific binding to a hemagglutinin target molecule). Certain variant amino acid positions may be selected as positions where mutations can include the insertion or deletion of amino acids, e.g., the insertion of 1 or 2 amino acids where the variant amino acid position occurs in a loop or turn region of the scaffold. In certain embodiments, the mutations can include the insertion or amino acids at one or more positions selected from positions 1, 9, 19, 38, 47 and 55. After selection of the GB1 scaffold, selection of the positions of variant amino acids, and selection of the nature of the mutations at each position, the individual sequences of the subject compounds can be determined.

Also provided are GB1 peptidic compounds that have been optimized for binding to a hemagglutinin target molecule by affinity maturation, e.g., second generation GB1 peptidic compounds based on a parent GB1 peptidic compound that binds to a hemagglutinin target molecule, where the second generation GB1 peptidic compounds are optimized for binding affinity and specificity.

In certain embodiments, the subject peptidic compounds specifically bind to a hemagglutinin target protein with high affinity, e.g., as determined by an SPR binding assay or an ELISA assay. The subject compounds may exhibit an affinity for a target protein of 1 uM or less, such as 300 nM or less, 100 nM or less, 30 nM or less, 10 nM or less, 5 nM or less, 2 nM or less, 1 nM or less, 300 pM or less, or even less. The subject peptidic compounds may exhibit a specificity for a hemagglutinin target protein, e.g., as determined by comparing the affinity of the compound for the target protein with that for a reference protein (e.g., an albumin protein), that is 5:1 or more 10:1 or more, such as 30:1 or more, 100:1 or more, 300:1 or more, 1000:1 or more, or even more. In some cases, the GB1 peptidic compounds may be optimized for any desirable property, such as protein folding, protease stability, thermostability, compatibility with a pharmaceutical formulation, etc. Any convenient methods of affinity maturation may be used to select second generation GB1 peptidic compounds, e.g., phage display methods.

In some embodiments, the affinity maturation of a subject compound may include holding a fraction of the variant amino acid positions as fixed positions while the remaining variant amino acid positions are varied to select optimal amino acids at each position. A parent GB1 peptidic compound that specifically binds to a hemagglutinin target molecule may be selected as a scaffold for an affinity maturation compound. In some cases, a number of affinity maturation compounds are prepared that include mutations at limited subsets of the variant amino acid positions of the parent (e.g., mutations at 4 of 15 variable positions), while the rest of the variant positions are held as fixed positions. The positions of the mutations may be tiled through the scaffold sequence to produce a series of compounds such that mutations at every variant position is represented and a diverse range of amino acids are substituted at every position (e.g., all 20 naturally occurring amino acids). Mutations that include deletion or insertion of one or more amino acids may also be included at variant positions of the affinity maturation compounds. An affinity maturation compound may be prepared and screened using any convenient method, e.g., phage display library screening, to identify second generation compounds having an improved property, e.g., increased binding affinity for a target molecule, protein folding, protease stability, thermostability, compatibility with a pharmaceutical formulation, etc.

In some embodiments, the affinity maturation of a subject compound may include holding most or all of the variant amino acid positions in the variable regions of the parent GB1 compound as fixed positions, and introducing contiguous mutations at positions adjacent to these variable regions. Such mutations may be introduced at positions in the parent GB1 compound that were previously considered fixed positions in the original GB1 scaffold domain. Such mutations may be used to optimize the GB1 compound variants for any desirable property, such as protein folding, protease stability, thermostability, compatibility with a pharmaceutical formulation, etc.

Methods

As summarized above, aspects of the invention include methods of producing D-peptidic compounds that specifically bind to hemaggluttinin target proteins. D-peptidic compounds are enantiomers of L-peptidic compounds. D-peptidic compounds may be composed of D-amino acid residues. In some embodiments, the D-peptidic compounds are resistant to proteases and have longer serum and/or saliva half-lives than their L-peptidic compound enantiomers. In certain embodiments, the D-peptidic compounds have 10% or greater, such as 20% or greater, 30% or greater, 40% or greater, 50% or greater, 100% or greater, 200% or greater stability to a protease compared to a L-peptidic compound, in a protease stability assay such as that described by Tugyi et al. (2005), "Partial D-amino acid substitution: Improved enzymatic stability and preserved Ab recognition of a MUC2 epitope peptide", PNAS, 102, 413-418; and Fischer, P M. (2003). In certain embodiments, D-peptidic compounds can be systemically absorbed after oral administration. In certain embodiments, the D-peptidic compounds have low immunogenicity compared to an L-peptidic compound. In certain embodiments, the D-peptidic compounds are 10% or less, 20% or less, 30% or less, 40% or less, 50% or less, 70% or less, or 90% or less immunogenic compared to an L-peptidic compound, in an immunogenicity assay such as that described by Dintzis et al., "A Comparison of the Immunogenicity of a Pair of Enantiomeric Proteins" Proteins: Structure, Function, and Genetics 16:306-308 (1993).

One aspect of the subject methods of producing D-peptidic compounds includes screening L-peptidic libraries for binding to D-peptidic hemagglutinin target proteins, e.g., a D-peptidic mimic of a hemagglutinin protein. By screening is meant contacting the target protein with a library of peptidic compounds and determining whether or not one or more members of the library specifically bind to the target. Aspects of the subject methods include contacting a sample containing a D-peptidic hemagglutinin target protein with a L-peptidic library.

The D-target proteins may be D-enantiomers of any convenient target proteins, e.g., therapeutic or diagnostic targets, such that the D-enantiomers have a chiral specificity for ligands that is the opposite of the L-target protein. In some embodiments, the D-target protein is a D-peptidic fragment of a therapeutic or diagnostic target, e.g., a fragment that includes a particular motif of the original target of interest. In some embodiments, the D-target protein is a D-peptidic mimic of a therapeutic or diagnostic target, or fragment thereof.

In some embodiments, the D-target protein, or mimic thereof, comprises 10 or more, 15 or more, 20 or more, 25 or more, 30 or more amino acid residues, such as 35 or more, 40 or more, 45 or more, 50 or more, 55 or more, 60 or more, 65 or more, 70 or more, 75 or more, 80 or more, 85 or more, 90 or more, 95 or more, 100 or more, 110 or more, 120 or more, 125 or more, 130 or more, 140 or more, 150 or more, 175 or more, or 200 more residues. In certain embodiments, the residues of the D-target protein, or mimic thereof, form a continuous sequence. In other embodiments, the residues of the D-target protein, or mimic thereof, may be discontinuous, e.g., linked sequence fragments. In certain embodiments, the D-target protein includes a dimer of sequences, each sequence having 10 or more residues (e.g., 15 or more, 20 or more, 25 or more, 30 or more amino acid residues, etc.) linked via a peptidic or non-peptidic linker. In certain embodiments, the D-target protein is 40 residues or larger, i.e., includes 40 or more residues, such as 65 or more residues. In some embodiments, the D-target protein has a MW of between 3,300 and 22,000 Da, such as between 4,400 and 22,000 Da, between 4,400 and 11,000 Da, between 4,400 and 8,800 Da, between 4,400 and 6,600 Da.

The D-target proteins are D-peptidic, e.g., composed of D-amino acids and glycine, and may be prepared using any convenient synthetic methods. In some embodiments, the D-target proteins are prepared using stepwise solid phase peptide synthesis methods, e.g., such as the stepwise addition of amino acids in a solid-phase Merrifield-type synthesis. Such methods may be used to prepare D-targets of high purity that are free from undesirable side products. For the synthesis of a D-target protein, D-amino acids or protected D-amino acids are utilized rather than the L-amino acids. D-amino acids suitable for polypeptide synthesis are commercially available, e.g., from the Peptide Institute (Osaka, Japan); Peptides International (Louisville, Ky.); Bachem Bioscience (Philadelphia, Pa.); and Bachem California, (Torrance, Calif.). A summary of some of the various methods available for synthesizing D-target proteins can be found in Steward et al., in "Solid Phase Peptide Synthesis", W.H. Freeman Co., San Francisco, 1969; Bodanszky et al., in "Peptide Synthesis", John Wiley & Sons, Second Edition, 1976 and Meienhofer, in "Hormonal Proteins and Peptides", Vol. 2, p. 46, Academic Press (New York), 1983; and Kent, Ann. Rev. Biochem., 57, 957, 1988, for solid phase peptide synthesis, and Schroder et al., in "The Peptides", Vol. 1, Academic Press (New York), 1965 for solution synthesis. Any convenient protecting group strategies may be used such as, but are not limited to, Fmoc solid-phase peptide synthesis and Boc solid-phase peptide synthesis strategies. In Boc solid-phase peptide synthesis a Boc-amino protecting group is used at the amino terminal and benzyl or benzyl-based protecting groups may be used for the protection of sidechain functional groups. In Fmoc solid-phase peptide synthesis a Fmoc-amino protecting group is used at the amino terminal and tert-butyl or benzyl-based protecting groups may be used for protection of sidechain functional groups. Convenient protecting groups that may be used in such synthetic methods are described in the above references and by McOmic in "Protective Groups in Organic Chemistry", Plenum Press, New York, 1973; and Greene and Wuts, "Protective Groups in Organic Synthesis", John Wiley & Sons, 4th Edition, 2006.

In some embodiments, the D-target proteins are prepared by the assembly of polypeptide building blocks using native chemical ligation methods. In this procedure, two or more polypeptide fragments are first synthesized, that contain termini adapted for native chemical ligation or for kinetically controlled ligation. After stepwise chemical synthesis and cleavage from their respective solid phase resins, and after purification e.g. by reverse phase HPLC, two of the two or more polypeptides are mixed and reacted to join the adapted termini and form a larger, linear polypeptide that includes the two polypeptides linked by a native amide bond. Further native chemical ligation and/or kinetically controlled ligation reactions can then be performed to add further polypeptide fragments in a convergent synthetic strategy. For a review of native chemical ligation and kinetically controlled ligation methods for the preparation of proteins see, e.g., "Total chemical synthesis of proteins," Stephen B. H. Kent, Chem. Soc. Reviews, 38, 338-51 (2009). After the polypeptide chain corresponding to the D-target protein has been prepared, it is folded with concomitant formation of native disulfide bonds if such are present in the native L-protein target, to form the defined tertiary structure that is the mirror image of the native L-protein target.

Once the D-target protein has been produced, it may be optionally purified or used without further purification. Purification may be performed using any convenient method, for example, using chromatography (e.g., RP-HPLC, ion exchange, affinity, and sizing column chromatography), centrifugation, differential solubility, or any other convenient technique for the purification of proteins.

In some cases, the synthetic D-target protein that is produced exists in a random coil or an unfolded state. The D-target protein may then be folded using any convenient method, such that the D-target protein folds from the random coil or unfolded state into a characteristic three-dimensional structure. In some cases, folding a D-target protein includes dissolving the protein in an aqueous buffer under conditions that mimic physiological conditions (e.g., conditions of pH, ionic strength, temperature, and the like) and allowing the D-target protein to fold into a characteristic three-dimensional structure in solution over a period of time (e.g., 2 days). The progress of folding of the D-target protein may be followed using any convenient methods, such as HPLC, circular dichroism, etc. See, e.g., Boerema et al., ("Total synthesis by modern chemical ligation methods and high resolution (1.1 Å) X-ray structure of ribonuclease A," Peptide Science, 90(3), 278-286, 2008) for an exemplary folding method of a synthetic protein. The D-target protein may form a structure that is the mirror image of that of the L-target protein of interest. In some cases, the protein folding solution is achiral. In some cases, the protein folding solution includes one or more chiral components, or enantiomers thereof, that may modulate the kinetics of protein folding.

Hemagglutinin Target Proteins

In some embodiments, the target protein is a hemagglutinin protein. Hemagglutinin (HA) is found on the surface of influenza viruses. HA has a N-terminal domain ($HA_1$) that binds to the viral receptor, and a C-terminal domain ($HA_2$) that mediates fusion with the host cell. In some cases, antibodies that effectively neutralize a broad range of influenza A viruses bind to a conserved epitope in the $HA_2$ region of the influenza hemagglutinin protein.

As used herein, the term "a hemagglutinin target protein" refers to all members of the hemagglutinin family, and fragments and protein mimics thereof, and enantiomers thereof. The term "hemagglutinin target protein" is intended to include L- and D-enantiomers and recombinant and synthetic molecules, which can be prepared using any convenient recombinant expression methods or using any convenient synthetic methods, or purchased commercially, as well as fusion proteins containing a target protein, as well as synthetic L- or D-proteins (e.g., a D-peptidic HA fragment or mimic). As used herein, the term "hemagglutinin mimic" refers to a peptidic compound that is L-peptidic or D-peptidic and that functionally and/or structurally mimics a hemagglutinin target protein or a portion or fragment thereof, or an enantiomer thereof. In some embodiments, the hemagglutinin mimic may have a peptidic sequence that is different from the hemagglutinin target protein but which still substantially retains one or more biochemical properties of the hemagglutinin target protein, such as a binding interaction to an antibody. It is understood that a hemagglutinin (HA) mimic may be a mimic of a D-target protein or a L-target protein, and as such may be referred to as a D-peptidic or L-peptidic hemagglutinin mimic, and that although a D-peptidic hemagglutinin mimic does not have the same biochemical properties as a corresponding L-peptidic hemagglutinin mimic, the mimics do have mirror image structures.

In some embodiments, the hemagglutinin target protein is D-peptidic (e.g., the D-enantiomer of a L-target protein, or the D-enantiomer of a L-peptidic mimic of a L-target protein), and as such is a compound that includes D-peptidic motifs corresponding to an enantiomer of the original L-hemagglutinin target protein of interest. In certain embodiments, the hemagglutinin target protein is an enantiomer of the native hemagglutinin protein of influenza A (HA), or a fragment thereof, or a mimic thereof.

In some cases, the hemagglutinin target protein is a HA mimic that finds use as a D-peptidic targets for screening or, alternatively, finds use in L-peptidic conjugates for vaccines.

Epitopes

HA mimics of interest may include the minimum essential features of the epitope of an influenza neutralizing antibody. A "neutralizing antibody" refers to immunoglobulin from a host animal which is capable of preventing or inhibiting virus infection. In some cases, the minimum essential features of the epitope are those residues determined by overlaying the HA epitope sequence onto an alpha helical coiled coil template, represented by the heptad repeat sequence (abcdefg)$_n$. As used herein, "minimum essential features of the epitope" refers to residues of the HA epitope that are conserved in the corresponding a coiled coil HA mimic sequence. In general terms, the HA epitopes of interest are aligned with the repeating heptad sequence (abcdefg)$_n$, on each strand of the coiled coil template, where the amino acids at positions "a" and "d" in both strands, are hydrophobic residues of the template, and the amino acids at positions "b", "c", "e", "f", and "g" correspond to the amino acid residues at corresponding. The display of a HA epitope on a coiled coil scaffold may be achieved using any convenient methods, for example, methods adapted from those described by Corti et al. for optimizing the register or positioning of an epitope with respect to an underlying coiled coil scaffold (see FIG. 8).

Residues of any convenient HA epitopes of interest may be inserted into/overlaid onto the scaffold at surface exposed positions on each strand, e.g., as described above. In certain embodiments, the coiled coil scaffold mimics the structure of Helix A of HA. In some embodiments, the coiled coil scaffold has a heptad repeat sequence that includes a repeating pattern of hydrophobic residues that are capable of forming interstrand hydrophobic interactions.

In some embodiments, the D-peptidic hemagglutinin target protein is a D-enantiomer of a protein mimic of an influenza HA protein fragment, for example a mimic of the HA$_2$ region of HA. In some embodiments, the influenza neutralizing antibody has broad spectrum activity against Group 1 Influenza A viruses (e.g., one or more of H1, H2, H5, H6, H8 and H9 viruses). In some embodiments, the influenza neutralizing antibody has broad spectrum activity against Group 2 Influenza A viruses (e.g., one or more of H3, H4, H7 and H10 viruses). Any convenient HA epitopes may be used in producing the subject D-target proteins, for example, an HA epitope that binds to influenza A neutralizing antibodies as described by Hodges et al. (WO2011/094363, US2012/0009212 and US2012/0014972), Ekiert et al. ("A highly conserved neutralizing epitope on group 2 influenza A viruses" Science Express, 7 Jul. 2011, 1204839 and supporting online material, and Corti et al. "A neutralizing antibody selected from plasma cells that binds to group I and group 2 influenza A hemagglutinins" Science Express, 28 Jul. 2011, 1205669 and supporting online material, revised 12 Aug. 2011, the disclosures of which are herein incorporated by reference.

In certain embodiments, the hemagglutinin mimic incorporates, via a coiled coil scaffold overlap, an epitope having 60% or greater amino acid sequence identity, such as 65% or greater, 70% or greater, 75% or greater, 80% or greater, 90% or greater, or 95% or greater amino acid sequence identity to an epitope of a HA protein of interest, or a consensus sequence thereof. The epitope may be a continuous or a discontinuous epitope and so the epitope-mimicking sequence of HA mimic may also be continuous or discontinuous. HA epitopes of interest include, but are not limited to, sequences H1-H16 corresponding to helix A of hemagglutinin proteins of various influenza A strains, or a consensus sequence thereof:

```
                                  (SEQ ID NO:  47)
H1    (1-24)    QKSTQNAIDGITSKVNSVIEKMNT (SEQ ID NO:  48)
H2    (1-24)    KESTQKAIDGITNRVNSVIEKMNT (SEQ ID NO:  49)
H3    (1-24)    LKSTQAAIDQINGKLNRVIEKTNE (SEQ ID NO:  50)
H4    (1-24)    LKSTQAAIDQINGKLNRLIEKTND (SEQ ID NO:  51)
H5    (1-24)    KESTQKAIDGITNKVNSIIDKMNT (SEQ ID NO:  52)
H6    (1-24)    RESTQKAVDGITNKVNSIIDKMNT (SEQ ID NO:  53)
H7    (1-24)    YKSTQSAIDQITGKLNRLIEKTNQ (SEQ ID NO:  54)
H8    (1-24)    QKSTQEAIDKITNKVNNIVDKMNR (SEQ ID NO:  55)
H9    (1-24)    KGSTQKAIDKITSKVNNIIDKMNK (SEQ ID NO:  56)
H10   (1-24)    YKSTQAAIDQITGKLNRLIEKTNT (SEQ ID NO:  57)
H11   (1-24)    KESTQKAIDQITSKVNNIVDRMNT (SEQ ID NO:  58)
H12   (1-24)    RDSTQRAIDNMQNKLNNVIDKMNK (SEQ ID NO:  59)
H13   (1-24)    KESTQKAIDQITTKINNIIDKMNG (SEQ ID NO:  60)
H14   (1-24)    LKSTQAAIDQINGKLNRLIEKTNE (SEQ ID NO:  61)
H15   (1-24)    YKSTQAAIDQITGKLNRLIEKTNK (SEQ ID NO:  62)
H16   (1-24)    KASTQKAIDEITTKINNIIEKMNG.
```

In some embodiments, the HA epitope of interest includes the sequence of Helix A 41-57 TQNAIDGITSKVNSVIE (SEQ ID NO:63). In some embodiments, the HA epitope of interest includes a consensus sequence of Helix A 41-57, e.g., a sequence based on a high degree of conservation of several amino acids across all 16 influenza subtypes. Such a consensus sequence may include the following amino acids at various positions (degree of conservation across influenza subtypes shown in parentheses): T41 (99.98); Q42 (99.96); I45 (99.23); D46 (99.60); I48 (93.61); T49 (74.95); V52 (99.91); N53 (99.93); V55 (99.71); I56 (99.90); E57 (94.14).

In certain embodiments, the HA epitope of interest has a consensus sequence described the following formula: TQXXIDXITXXVNXVIE (IX) (SEQ ID NO:64), where each X is independently selected from any amino acid. In some embodiments, in formula (IX), each X is independently selected from one of the amino acid residues found at the corresponding positions of epitopes H1-H16. In certain embodiments, the HA epitope of interest includes a sequence described the following:

```
                                                           (SEQ ID NO: 65)
TQ(A/E/K/N/R/S)A(I/V)D(E/G/K/N/Q)I(T/N)(G/N/S/T)(K/R)(I/L/V)N(N/R/S)(I/L/V)
(I/V)(D/E).
```

In some instances, the HA epitope of interest has a sequence of any convenient Group 2 influenza A virus epitope that binds to a broadly neutralizing antibody to Group 2 influenza A viruses (see e.g., Table 1 of supporting online material for Ekiert et al., Science Express, 7 Jul. 2011, 1204839, the disclosure of which is herein incorporated by reference). In some embodiments, the HA epitope includes a sequence having 80% or greater (such as 90% or greater) amino acid sequence identity to the following:

```
                                                           (SEQ ID NO: 84)
E(E/Q)G(V/I/M)(D/N)R(E/Q)(T/E/I/R)G(Q/T)AA(L/Y)(N/D)(G/E/A).
```

In some cases, the HA epitope of interest includes a sequence described by one of the exemplary consensus sequences of an influenza A virus epitope as described in Tables S3 and S4 of supporting online material for Ekiert et al., Science Express, 7 Jul. 2011, 1204839, the disclosure of which is herein incorporated by reference. In certain embodiments, the HA epitope includes a sequence having 80% or greater (such as 90% or greater) amino acid sequence identity to the following:

```
                      (SEQ ID NO: 85)
EEG(V/I)DRETGQAALN(G/E);

(SEQ ID NO: 86)
EEGVDRETGQAALNG.
```

Coiled Coil Scaffold

A coiled coil scaffold is a stable, two-stranded alpha helical peptide template that can display one or more HA epitopes of interest (e.g., as described herein). In some cases, the coiled coil scaffold displays a first epitope that comprises a HA epitope, and a second epitope that comprises a non-influenza protein epitope, such as one of the epitopes described by Hodges et al. in US 2012/0009212. In some instances, the coiled coil scaffold displays two or more HA epitopes of interest, where the two or more HA epitopes may be homologous or heterologous.

Any convenient coiled coil scaffolds may be utilized in the preparation of subject HA mimics. Coiled coil scaffolds which may be adapted for use in the subject HA mimics as vaccines or as D-peptidic targets are described by Hodges et al. in WO2011/094363, US2012/0009212 and US2012/0014972, the disclosures of which are herein incorporated by reference.

As used herein, the terms "peptide template", "scaffold", "templated epitope" and "epitope template" are used interchangeably, and refer to sequence of residues that includes an underlying motif upon which a biologically active sequence of interest (e.g., an epitope) is overlaid to produce a new hybrid sequence.

In certain embodiments, the D-peptidic hemagglutinin target protein is an enantiomer of a mimic of a HA protein of interest (e.g., a mimic of the $HA_2$ region of HA) that includes the minimum essential features of one of the HA epitopes of interest (e.g., H1-H16) displayed on a coiled coil scaffold. Any convenient coiled coil scaffold may be utilized in displaying a HA epitope of interest. In some embodiments, the coiled coil scaffold includes parallel strands of alpha-helical structure that are stabilized via hydrophobic core interactions and an interchain linker. Residues of the HA epitope of interest may then be inserted into the scaffold at surface exposed positions on each strand. In certain embodiments, the coiled coil scaffold mimics the structure of Helix A of HA. In some embodiments, the coiled coil scaffold has a heptad repeat sequence that includes a repeating pattern of hydrophobic residues that are capable of forming interstrand hydrophobic interactions.

In certain embodiments, each strand of the two-stranded helix comprises a repeating heptad sequence $(\underline{a}bc\underline{d}efg)_n$, where amino acids at position "a" in both strands, and at position "d" in both strands, are hydrophobic residues (e.g., positions "a" are isoleucines and positions "d" are leucines), such that the repeating "a" and "d" residues form stabilizing inter-strand hydrophobic interactions (see e.g., FIG. 4 of WO2001/094363). The remaining positions b, c, e, f, and g of the heptad repeat sequence may be used to display some of the residues of the HA epitope of interest (e.g., some of residues 1-24 of epitopes H1-H16). The display of a HA epitope on a coiled coil scaffold may be achieved using any convenient methods, for example, methods adapted from those described by Corti et al. for optimizing the register or positioning of an epitope with respect to an underlying coiled coil scaffold (see FIG. 8). In a displayed epitope, the heptad repeat sequence may begin and end at any convenient places in the heptad and may include one or more (e.g., 1, 2 or 3) heptads or fragments thereof, e.g., defgabcdefga. In describing the alignment of the heptad repeat register with respect to the epitope of interest, the numbering system depicted in FIG. 9 may be utilized, as illustrated by registers 1-7. For example, a coiled coil mimic having register 1 may be described as having a heptad repeat beginning at position 4 (i.e., where the "a" residue of the heptad repeat is located at position 4 of the epitope). The two peptidic strands may be connected via a linker, e.g., a disulfide bridge between cysteine residues of the two peptide strands. The linker may be positioned N-terminal or C-terminal relative to the heptad repeat sequence. In some embodiments, the HA coiled coil mimic is described by one of formulas (X) and (XI):

$$\begin{array}{c} T^1\!-\!Z^1 \\ | \\ L \\ | \\ T^2\!-\!Z^2 \end{array} \quad (X)$$

$$\begin{array}{c} Z^1\!-\!T^1 \\ | \\ L \\ | \\ Z^2\!-\!T^2 \end{array} \quad (XI)$$

where $Z^1$ and $Z^2$ are peptidic sequences that each independently include a HA epitope displayed on a coiled coil scaffold, $T^1$ and $T^2$ are optional tethers, and L is a linker. In some instances, in formulas (X) or (XI), the HA coiled coil mimic is L-peptidic. In other instances, in formulas (X) or (XI), the HA coiled coil mimic is D-peptidic. In some embodiments, $Z^1$ and $Z^2$ are identical sequences, such that the HA mimic is homodimeric. $Z^1$ and $Z^2$ may include a heptad repeat sequence as described herein, e.g., as described in FIG. 9.

In some instances, the HA coiled coil mimic includes a HA epitope arranged on a coiled coil scaffold according to the alignment of the heptad repeat sequence with epitope H1 illustrated in FIG. 9 as sequence CC H1 overlap. Any convenient epitope (e.g., epitopes H1 to H16) may be aligned as demonstrated for H1 in general formula CC H1 overlap (FIG. 9). In certain embodiments, the HA coiled coil mimic includes one or more sequences described by one of the following:

|  |  | (SEQ ID NO: 87) |
|---|---|---|
| H1 | (1-24) | QKSaQNdIDGaTSdVNSaIEd |

|  |  | (SEQ ID NO: 88) |
|---|---|---|
| H2 | (1-24) | KESaQKdIDGaTNdVNSaIEd |

|  |  | (SEQ ID NO: 89) |
|---|---|---|
| H3 | (1-24) | LKSaQAdIDQaNGdLNRaIEd |

|  |  | (SEQ ID NO: 90) |
|---|---|---|
| H4 | (1-24) | LKSaQAdIDQaNGdLNRaIEd |

|  |  | (SEQ ID NO: 91) |
|---|---|---|
| H5 | (1-24) | KESaQKdIDGaTNdVNSaIDd |

|  |  | (SEQ ID NO: 92) |
|---|---|---|
| H6 | (1-24) | RESaQKdVDGaTNdVNSaIDd |

|  |  | (SEQ ID NO: 93) |
|---|---|---|
| H7 | (1-24) | YKSaQSdIDQaTGdLNRaIEd |

|  |  | (SEQ ID NO: 94) |
|---|---|---|
| H8 | (1-24) | QKSaQEdIDKaTNdVNNaVDd |

|  |  | (SEQ ID NO: 95) |
|---|---|---|
| H9 | (1-24) | KGSaQKdIDKaTSdVNNaIDd |

|  |  | (SEQ ID NO: 96) |
|---|---|---|
| H10 | (1-24) | YKSaQAdIDQaTGdLNRaIEd |

|  |  | (SEQ ID NO: 97) |
|---|---|---|
| H11 | (1-24) | KESaQKdIDQaTSdVNNaVDd |

|  |  | (SEQ ID NO: 98) |
|---|---|---|
| H12 | (1-24) | RDSaQRdIDNaQNdLNNaIDd |

|  |  | (SEQ ID NO: 99) |
|---|---|---|

-continued

|  |  | (SEQ ID NO: 99) |
|---|---|---|
| H13 | (1-24) | KESaQKdIDQaTTdINNaIDd |

|  |  | (SEQ ID NO: 100) |
|---|---|---|
| H14 | (1-24) | LKSaQAdIDQaNGdLNRaIEd |

|  |  | (SEQ ID NO: 101) |
|---|---|---|
| H15 | (1-24) | YKSaQAdIDQaTGdLNRaIEd |

|  |  | (SEQ ID NO: 102) |
|---|---|---|
| H16 | (1-24) | KASaQKdIDEaTTdINNaIEd | where "a" and "d" are each independently hydrophobic residues (e.g., Leu, Ile, Ala, Phe, or Val), and where the heptad repeat register of the sequences may be described as beginning at position 4 of epitopes H1-H16. In some embodiments, "a" and "d" are each independently isoleucine or leucine. In certain instances, each "a" is an isoleucine and each "d" is a leucine. It is understood that the above HA mimics may be L-peptidic or D-peptidic, and that the heptad repeat sequence may be extended further in the N-terminal and/or C-terminal direction, e.g., as illustrated in FIGS. 9-12.

In some instances, the HA coiled coil mimic includes an H1-H16 epitope sequence having a heptad repeat register 1, as depicted in FIG. 9. In certain instances, the HA coiled coil mimic includes an epitope sequence that does not have any one of registers 2-7, as depicted in FIG. 9. In certain instances, the HA coiled coil mimic includes an epitope sequence that does not have register 2, or register 3 or register 4, or register 5 or register 6 or register 7, as depicted in FIG. 9. In certain instances, the HA coiled coil mimic includes an H1-H16 epitope sequence that does not have register 4, as depicted in FIG. 9.

The tethers may be peptidic. In some embodiments, one or both of the tethers may further include an affinity tag (e.g., a biotin moiety). In some embodiments, when $T^1$ and $T^2$ are absent, the linker L connects $Z^1$ and $Z^2$ directly, e.g., via sidechain moieties of any two convenient residues. In some embodiments, the tethers $T^1$ and $T^2$ each independently include a peptidic sequence of 10 or fewer, such as, 8 or fewer, 6 or fewer, 5 or fewer, 4 or fewer, or 3 or fewer residues. In some embodiments, the tethers $T^1$ and $T^2$ include a cysteine-containing peptidic sequence, e.g., CAA or CRR. In some embodiments, L is a covalent bond, e.g., a disulfide bond that connects two cysteine residues. In some embodiments, L is peptidic. In some embodiments, L is a polyethyleneoxy or a $C_1$-$C_6$ linker. In some embodiments, L connects two residues of $T^1$ and $T^2$.

In certain embodiments, in formulas (X) and (XI), $Z^1$ and $Z^2$ each independently include one of the following sequences:

|  | (SEQ ID NO: 66) |
|---|---|
| lqksiqnlidGitslvnsi | |

|  | (SEQ ID NO: 67) |
|---|---|
| lkesiqklidGitnlvnsi | |

|  | (SEQ ID NO: 68) |
|---|---|
| llksiqalidqinGllnri | |

|  | (SEQ ID NO: 69) |
|---|---|
| iaalqksiqnlidGitslvnsiielmnt | |

|  | (SEQ ID NO: 70) |
|---|---|
| iaalkesiqklidGitnlvnsiielmnt | |

|  | (SEQ ID NO: 71) |
|---|---|
| iaallksiqalidqinGllnriieltne. | |

In certain embodiments, the D-target protein includes minimum essential features of one or more peptidic sequences selected from H1-H16, or a consensus sequence thereof. In certain embodiments, the D-target protein includes minimum essential features of one or more peptidic sequences selected from H1-H3, or a consensus sequence thereof.

In certain embodiments, the D-target protein includes a sequence having 60% or greater amino acid sequence identity, such as 65% or greater, 70% or greater, 75% or greater, 80% or greater, 90% or greater, 95% or greater amino acid sequence identity to one of sequences H1-H3.

Exemplary D-target protein mimics of hemagglutinin proteins of interest include but are not limited to one of the following Cys-Cys disulfide linked dimeric mimics:

```
1. H1 mimic:
biotin-nle--caalqksiqnlidGitslvnsi-amide  (SEQ ID NO: 72)
           |
        Ac-caalqksiqnlidGitslvnsi-amide    (SEQ ID NO: 73)
2. H2 mimic:
biotin-nle--caalkesiqklidGitnlvnsi-amide  (SEQ ID NO: 74)
           |
        Ac-caalkesiqklidGitnlvnsi-amide    (SEQ ID NO: 75)
3. H3 mimic:
biotin-nle--caallksiqalidqinGllnri-amide  (SEQ ID NO: 76)
           |
        Ac-caallksiqalidqinGllnri-amide    (SEQ ID NO: 77)
4. H1 mimic:
biotin-nle--iaalqksiqnlidGitslvnsiielmntcrr-amide  (SEQ ID NO: 78)
           |
        Ac-iaalqksiqnlidGitslvnsiielmntcrr-amide    (SEQ ID NO: 79)
5. H2 mimic:
biotin-nle--iaalkesiqklidGitnlvnsiielmntcrr-amide  (SEQ ID NO: 80)
           |
        Ac-iaalkesiqklidGitnlvnsiielmntcrr-amide    (SEQ ID NO: 81)
6. H3 mimic:
biotin-nle--iaallksiqalidqinGllnriieltnecrr-amide  (SEQ ID NO: 82)
           |
        Ac-iaallksiqalidqinGllnriieltnecrr-amide    (SEQ ID NO: 83)
```

In some embodiments, the D-target protein is a D-enantiomer of a coiled coil H1-H16 mimic as depicted in FIGS. 10-12. In certain embodiments, the coiled coil hemagglutinin mimic comprises a sequence having 70% or greater (such as 80% or greater, 90% or greater, or 95% or greater) amino acid sequence identity to one of SEQ ID NOs:124-139 of FIGS. 10-12. It is understood that any one of the coiled coiled mimics described herein may be adapted depending on the method of use. For example, any convenient N-terminal and C-terminal groups (e.g., biotin and acetyl or amide terminal capping groups) may be selected and optionally incorporated with any of the coiled coil mimics described herein. In some instances, the coiled coil H1-H16 mimics of interest as depicted in FIGS. 10-12 are utilized with a biotin group at the N-terminal or C-terminal of one of the sequences for use in the method of screening. Any convenient optional tags and/or optional capping groups, located at any convenient positions of the sequences, may be utilized. In some embodiments, the coiled coil HA mimic is a heterodimer comprising any two heterologous sequences selected from the H1-H16 sequences depicted in FIGS. 10-12.

In some instances, the D-target protein is a D-enantiomer of a peptidic sequence for use as a vaccine against influenza A, e.g., such as those described by Hodges et al. (WO2011/094363) and Corti et al. "A neutralizing antibody selected from plasma cells that binds to group 1 and group 2 influenza A hemagglutinins" Science Express, 28 Jul. 2011, 1205669 and supporting online material, revised 12 Aug. 2011.

In some embodiments, the D-target protein is a D-peptidic version of an HA mimic (e.g., as described by Hodges et al. (WO2011/094363)) that is a conformationally stabilized two-stranded peptide unit of the formula PX1-L-PX2, where L is a linker and PX1 and PX2 are each independently selected from D-enantiomers of one of the sequences 5A.T, 6A.T, 1A.T, 3A.T, 4A.t, 3M1.T/3M.T, 3M2.T/3M*.T, 3 Mp.t, 5P.T, 6P.T, and 5P.T, as described by Hodges et al. (WO2011/094363).

In some embodiments, the D-target protein is a D-enantiomer of a peptidic fragment of a therapeutic or diagnostic target, e.g., a fragment that includes a particular motif of the original target of interest.

In some instances, the D-target protein is a D-enantiomer of an HA mimic such as those described by Bommakanti et al., PNAS, v107, 13701-6, Aug. 3, 2010, "Design of an HA2-based E. coli expressed influenza immunogen that protects mice from pathogenic challenge". In certain embodiments, the D-target protein is described by the following sequence, or a fragment thereof:

```
                                            (SEQ ID NO: 103)
GLFGAIAGFI ENGWEGMIDG WYGFRHQNSE GTGQAADLKS

TQAAIDQING KLNRVIEKTN EKFHQIEKEF SEVEGRIQDL

EKYVEDTKID LWSYNAELLV ALENQHTIDL TDSEMNKLFE

KTRRQLRENA EDMGNGCFKI YHKCDNACIE SIRNGTYDHD

VYRDEALNNR FQ (H2)

SAGSAG (Linker)

DNSTATLCLG HHAVPNGTLV KTITDDQIEV TNATELVQSS
(H1)

GSAGSA (Linker)

NDKPFQNVNKITYGACPKYVKKQNTLKLATGMR (H1)

KLAAALEHHHHHH (His tag).
```

In certain embodiments, the D-target protein is described by the following sequence, or a fragment thereof:

```
                                            (SEQ ID NO: 104)
GLCGAIAGFI  ENGWEGMIDG  WYGFRHQNSE  GTGQAADLKC

TQAAIDQING  KLNRVIEKTN  EKDHQIEKEF  SEDEGRIQDL

EKYVEDTKID  LWSYNAELLV  ALENQHTIDL  TDSEMCKCFE

KTRRQLRENA  EDMGNGCFKI  YHKCDNACIE  SIRNGTYDHD

VYRDEALNNR  FQGSAGSAGD  NSTATLCLGH  HAVPNGTLVK

TITDDQIEVT  NATELVQSSG  SAGSANDKPF  QNTNKETTGA

CPKYVKKQNT  LKLATGMR.
```

In certain embodiments, the D-target protein is a D-enantiomer of a peptidic fragment that corresponds to a domain of the original target protein of interest. In certain embodiments, the D-target protein is a D-enantiomer of a peptidic fragment that corresponds to a structural motif of the original target protein of interest. In certain embodiments, the structural motif is a sequence of residues that folds to form a stable structure that mimics the structure of the original protein target. Such fragments may be of interest for ease of synthesis and/or for screening for specific binding to a particular motif of interest.

In some embodiments, the D-target protein is a D-enantiomer of a target protein mimic of a therapeutic or diagnostic target, or fragment thereof. In certain embodiments, the D-target protein is a D-enantiomer of a mimic of a native protein of interest, or a fragment thereof, that includes the minimum essential features of a potential binding surface of the target protein (e.g., an epitope). In certain embodiments, the D-target protein is a D-enantiomer of a mimic that includes a sequence having 60% or greater amino acid sequence identity, such as 65% or greater, 70% or greater, 75% or greater, 80% or greater, 90% or greater, 95% or greater amino acid sequence identity to a fragment (e.g., an epitope) of an original protein of interest.

In some embodiments, the D-target protein is a D-enantiomer of a protein mimic, e.g., a compound that includes peptidic motifs that mimic an original target protein of interest, e.g., as described above.

In certain embodiments, the D-target protein includes one or more peptidic sequences corresponding to the peptidic sequences of a binding motif of an original target protein of interest.

In certain embodiments, the D-target protein is a D-enantiomer of a mimic that includes a sequence having 60% or greater amino acid sequence identity, such as 65% or greater, 70% or greater, 75% or greater, 80% or greater, 90% or greater, 95% or greater amino acid sequence identity to a fragment of an original target protein of interest. In certain embodiments, the D-target protein is a D-enantiomer of a mimic that includes the minimum essential features of a binding motif displayed on a scaffold (e.g., a conformationally stabilized scaffold that closely mimics a motif of the original target protein).

In some embodiments, the production of a protein mimic is of interest when the native target protein is large and/or not accessible by chemical synthesis, or when screening for binding to one particular motif of the original target protein is desired.

Methods of Screening

As summarized above, aspects of the screening methods include contacting a sample containing a D-target protein that is a hemagglutinin target protein with a L-peptidic library.

In some embodiments, each compound of the L-peptidic library includes 10 or more residues, such as 15 or more, 20 or more, 25 or more, 30 or more, 35 or more, 40 or more, 50 or more, 60 or more, 70 or more, 80 or more, 90 or more, or 100 or more residues. In some embodiments, each compound of the L-peptidic library includes between 20 and 80 residues, such as between 30 and 80 residues, between 40 and 70 residues, between 45 and 60 residues, or between 52 and 58 residues. In certain embodiments, each compound of the subject library includes a peptidic sequence of 52, 53, 54, 55, 56, 57 or 58 residues. In certain embodiments, the peptidic sequence is of 55, 56 or 57 residues, such as 56 residues.

In some embodiments, each compound of the L-peptidic library includes a scaffold domain and a variable domain. The scaffold domain may have a structural motif that is conserved across the members of the library. The scaffold domain may fold to form a stable structure that includes a potential target protein binding surface that can carry variant amino acids without significantly disrupting the structure of the scaffold. The variant amino acids of the potential target binding surface may define a variable domain that is part of the scaffold domain. In some cases, the scaffold domain structure is not susceptible to unfolding in reducing intracellular environments, and does not significantly aggregate under physiological conditions.

A variety of scaffold domains may be used in the L-peptidic libraries. Scaffold domains of interest include but are not limited to non-immunoglobulin scaffold domains, such as those domains described in Table 1 of the review by Binz et al. ("Engineering novel binding proteins from nonimmunoglobulin domains," Nature Biotechnology 23, 1257-1268, 2005), which is entirely incorporated herein by reference.

In some embodiments, each compound of the L-peptidic library has a distinct variable domain that includes 5 or more, such as, 8 or more, 9 or more, 10 or more, 11 or more, 12 or more, 13 or more, 14 or more, or 15 or more mutations. The majority of mutations are included at various non-core positions of the scaffold, i.e., variant amino acids at non-core positions within a scaffold domain. The diversity of the libraries is designed to maximize diversity while minimizing structural perturbations of the scaffold domain. The positions to be mutated are selected to ensure that the compounds of the libraries can maintain a folded state under physiological conditions. Another aspect of generating diversity in the subject libraries is the selection of amino acid positions to be mutated such that the amino acids can form a potential binding surface in the scaffold domain, whether or not the residues actually bind a target protein. One way of determining whether an amino acid position is part of a potential binding surface involves examining the three dimensional structure of the scaffold domain, using a computer program such as the Chimera program (UCSF). Other ways include crystallographic and genetic mutational analysis. Any convenient method may be used to determine whether an amino acid position is part of a potential binding surface.

The mutations may be found at positions in the scaffold domain where the amino acid residue is at least in part solvent exposed. Solvent exposed positions can be determined using software suitable for protein modeling and three-dimensional structural information obtained from a crystal structure. The mutations of the scaffold domain may be concentrated at one of several different potential binding surfaces of the scaffold domain. In some instances, the majority of the mutations are at non-core positions of the scaffold domain (i.e., solvent exposed or boundary positions) however in some cases one or more mutations may be located at hydrophobic core positions. Mutations at such positions may confer desirable properties upon the resulting compound variant, such as stability, a certain structure, or specific binding to a target protein.

Another aspect of the diversity of the subject libraries is the size of the library, i.e, the number of distinct compounds of the library. In some embodiments, a subject library includes 50 or more distinct compounds, such as 100 or more, 300 or more, $1 \times 10^3$ or more, $1 \times 10^4$ or more, $1 \times 10^5$ or more, $1 \times 10^6$ or more, $1 \times 10^7$ or more, $1 \times 10^8$ or more, $1 \times 10^9$ or more, $1 \times 10^{10}$ or more, $1 \times 10^{11}$ or more, or $1 \times 10^{12}$ or more, distinct compounds.

In some embodiments, the scaffold domain is a GB1 scaffold domain, i.e., a scaffold domain of the same structural motif as the B1 domain of Protein G (GB1), where the structural motif of GB1 is characterized by a motif that includes an arrangement of four β-strands and one α-helix (i.e., a 4β-1α motif) around a hydrophobic core. In some embodiments, the four β-strands and one α-helix motifs of the structure are arranged in a hairpin-helix-hairpin motif, i.e., β1-β2-α1-β3-β4 where β1-β4 are β-strand motifs and cd is a helix motif.

In certain embodiments, the L-peptidic library comprises 50 or more distinct compounds, where each of the 50 or more distinct compounds is a GB1 peptidic compound, and where each compound of the library comprises at least three different non-core mutations in a region outside of the β1-β2 region.

Exemplary GB1 peptidic libraries for use in the subject methods are described in the copending U.S. application entitled "GB1 peptidic libraries and methods of screening the same" filed on Nov. 10, 2011 to Sidhu et al. and accorded Ser. No. [13/294,072], and U.S. provisional application Ser. No. 61/413,318 filed Nov. 12, 2010, which are entirely incorporated herein by reference. FIG. 1 illustrates the sequences of exemplary GB1 peptidic libraries 1 to 6 and shows the positions of variant amino acids in the GB1 scaffold domain. FIGS. 2 to 7 illustrate phage display libraries 1 to 6 including the polynucleotide sequences that encode the variable regions of each library of L-peptidic compounds.

The L-peptidic libraries may be prepared by any convenient methods, such as, methods that find use in the preparation of libraries of peptidic compounds, for example, display methods (e.g., as described above). Any convenient display methods may be used to display the L-peptidic libraries, such as cell-based display techniques and cell-free display techniques. In certain embodiments, cell-based display techniques include phage display, bacterial display, yeast display and mammalian cell display. In certain embodiments, cell-free display techniques include mRNA display and ribosome display.

In some embodiments, the L-peptidic library is a phage display library. The phage display libraries may be rapidly and efficiently screened for those sequences that specifically bind to a D-target protein. In certain embodiments, the phage is a filamentous bacteriophage, such as an M13, f1, fd, Pf3 phage or a derivative thereof, or a lambdoid phage, such as lambda, 21, phi80, phi81, 82, 424, 434, M13KO7 helper phage, M13R408, M13-VCS, and Phi X 174, pJuFo phage system (J. Virol. 2001 August; 75(15):7107-13), hyperphage (Nat. Biotechnol. 2001 January; 19(1):75-8) etc., or a derivative thereof. In some embodiments, each compound of the L-peptidic library is fused to at least a portion of a viral coat protein. Examples of viral coat proteins include infectivity protein PIII, major coat protein PVIII, p3, Soc, Hoc, gpD (of bacteriophage lambda), minor bacteriophage coat protein 6 (pVI) (filamentous phage; J. Immunol. Methods, 1999, 231 (1-2):39-51), variants of the M13 bacteriophage major coat protein (P8) (Protein Sci 2000 April; 9(4):647-54). Any convenient methods for displaying fusion polypeptides including L-peptidic compounds on the surface of bacteriophage may be used. For example methods as described in patent publication numbers WO 92/01047; WO 92/20791; WO 93/06213; WO 93/11236 and WO 93/19172. In certain embodiments, the helper phage is M13KO7, and the coat protein is the M13 Phage gene III coat protein. In certain embodiments, the host is E. coli or protease deficient strains of E. coli. Vectors, such as the fthl vector (Nucleic Acids Res. 2001 May 15; 29(10): E50-0) can be useful for the expression of the fusion protein.

Fusion polypeptides including L-peptidic compounds may be displayed on the surface of a cell or virus in a variety of formats and multivalent forms. See e.g., Wells and Lowman (1992) Curr. Opin. Struct. Biol B:355-362 and references cited therein. The multivalent forms of display have more than one target binding site which in some cases results in the identification of lower affinity clones and may also allow for more efficient sorting of rare clones during the selection process. In certain embodiments, a bivalent moiety such as an anti-MBP (maltose binding protein) Fab scaffold (a hinge and dimerization sequence from a Fab template), is used for displaying the L-peptidic compound variants on the surface of phage particles.

In monovalent phage display, a L-peptidic library may be fused to a coat protein (e.g., a gene III protein) or a portion thereof and expressed at low levels in the presence of wild type coat protein so that phage particles display one copy or none of the fusion proteins. Avidity effects are reduced relative to multivalent phage so that sorting is on the basis of intrinsic ligand affinity, and phagemid vectors are used, which simplify DNA manipulations. See e.g., Lowman and Wells (1991) Methods: A companion to Methods in Enzymology 3:205-216. In phage display, the phenotype of the phage particle, including the displayed polypeptide, corresponds to the genotype inside the phage particle, the DNA enclosed by the phage coat proteins.

The expression vector of a display system also can have a secretory signal sequence fused to the DNA encoding each L-peptidic compound. This sequence may be located immediately 5' to the gene encoding the fusion protein, and will thus be transcribed at the amino terminus of the fusion protein. However, in certain cases, the signal sequence has been demonstrated to be located at positions other than 5' to the gene encoding the protein to be secreted. This sequence targets the protein to which it is attached across the inner membrane of the bacterial cell. The DNA encoding the signal sequence may be obtained as a restriction endonuclease fragment from any gene encoding a protein that has a signal sequence. In some cases, prokaryotic signal sequences may be obtained from genes encoding, for example, LamB or OmpF (Wong et al., Gene, 68:1931 (1983), MalE, PhoA and other genes. An exemplary prokaryotic signal sequence is the E. coli heat-stable enterotoxin II (STII) signal sequence as described by Chang et al., Gene 55:189 (1987), and malE.

The expression vector may also include a promoter to drive expression of the fusion protein. Promoters most commonly used in prokaryotic vectors include the lac Z promoter system, the alkaline phosphatase pho A promoter, the bacteriophage gamma-$_{PL}$ promoter (a temperature sensitive promoter), the tac promoter (a hybrid trp-lac promoter that is regulated by the lac repressor), the tryptophan promoter, and the bacteriophage T7 promoter. Any convenient microbial promoters may be used.

The expression vector may include other nucleic acid sequences, for example, sequences encoding gD tags, c-Myc epitopes, FLAG tags, poly-histidine tags, fluorescence proteins (e.g., GFP), or beta-galactosidase protein which can be useful for detection or purification of the fusion protein expressed on the surface of the phage or cell. Nucleic acid sequences encoding, for example, a gD tag, also provide for positive or negative selection of cells or virus expressing the fusion protein. In some embodiments, the gD tag is fused to a L-peptidic compound which is not fused to the viral coat protein. Nucleic acid sequences encoding, for example, a polyhistidine tag, are useful for identifying fusion proteins including L-peptidic compounds that bind to a specific target using immunohistochemistry. Tags useful for detection of target binding can be fused to either a L-peptidic compound not fused to a viral coat protein or a L-peptidic compound fused to a viral coat protein.

In some cases, the expression vectors are phenotypic selection genes. The phenotypic selection genes are those encoding proteins that confer antibiotic resistance upon the host cell. By way of illustration, the ampicillin resistance gene (ampr), and the tetracycline resistance gene (tetr) are readily employed for this purpose.

The expression vector may also include nucleic acid sequences containing unique restriction sites and suppressible stop codons. The unique restriction sites are useful for moving L-peptidic compound domains between different vectors and expression systems. The suppressible stop codons are useful to control the level of expression of the fusion protein and to facilitate purification of L-peptidic compounds. For example, an amber stop codon can be read as Gln in a supE host to enable phage display, while in a non-supE host it is read as a stop codon to produce soluble L-peptidic compounds without fusion to phage coat proteins. These synthetic sequences can be fused to L-peptidic compounds in the vector.

In some cases, vector systems that allow the nucleic acid encoding a L-peptidic compound of interest to be easily removed from the vector system and placed into another vector system, may be used. For example, appropriate restriction sites can be engineered in a vector system to facilitate the removal of the nucleic acid sequence encoding the L-peptidic compounds. The restriction sequences are usually chosen to be unique in the vectors to facilitate efficient excision and ligation into new vectors. L-peptidic compound domains can then be expressed from vectors without extraneous fusion sequences, such as viral coat proteins or other sequence tags.

Between nucleic acid encoding L-peptidic compounds (gene 1) and the viral coat protein (gene 2), DNA encoding a termination codon may be inserted, such termination codons including UAG (amber), UAA (ocher) and UGA (opel). (Microbiology, Davis et al., Harper & Row, New York, 1980, pp. 237, 245-47 and 374). The termination codon expressed in a wild type host cell results in the synthesis of the gene 1 protein product without the gene 2 protein attached. However, growth in a suppressor host cell results in the synthesis of detectable quantities of fused protein. Such suppressor host cells are well known and described, such as E. coli suppressor strain (Bullock et al., BioTechniques 5:376-379 (1987)). Any acceptable method may be used to place such a termination codon into the mRNA encoding the fusion polypeptide.

The suppressible codon may be inserted between the first gene encoding the L-peptidic compounds, and a second gene encoding at least a portion of a phage coat protein. Alternatively, the suppressible termination codon may be inserted adjacent to the fusion site by replacing the last amino acid triplet in the L-peptidic compound domain or the first amino acid in the phage coat protein. When the plasmid containing the suppressible codon is grown in a suppressor host cell, it results in the detectable production of a fusion polypeptide containing the polypeptide and the coat protein. When the plasmid is grown in a non-suppressor host cell, the L-peptidic compound domain is synthesized substantially without fusion to the phage coat protein due to termination at the inserted suppressible triplet UAG, UAA, or UGA. In the non-suppressor cell the L-peptidic compound domain is synthesized and secreted from the host cell due to the absence of the fused phage coat protein which otherwise anchored it to the host membrane.

As summarized above, aspects of the screening methods include contacting a sample containing a D-target protein that is a hemagglutinin target protein, with a L-peptidic library. The contacting step may be performed under conditions suitable for specifically binding members of the L-peptidic library with the D-target, whether or not such binding occurs. Such conditions include aqueous conditions in which D-target proteins of interest are able to be maintained in a folded state. In some cases, the conditions, including pH, ionic strength, temperature, and the like, mimic physiological conditions.

The contacting of the L-peptidic library and the D-target protein may be performed using any convenient method, such as, phage display screening methods, enzyme assay methods, ELISA assay methods, or other convenient biological assay methods for assessing specific binding or the inhibition of binding. The contacting step may be performed where the D-target is in solution phase or immobilized on a support, such as a beads, nanoparticles, planar surfaces or 96-well plates, gels, etc., that may include agarose, acrylamide, glass, silica, silicon, gold, plastic, cellulose, various acrylic copolymers, hydroxyalkyl methacrylates, polyacrylic and polymethacrylic copolymers, nylon, polystyrene, polyethylene or polypropylene, or the like. Attachment of the D-target protein to a support may be accomplished by any convenient methods, e.g., methods as described in Methods in Enzymology, 44 (1976), and Hermanson, "Bioconjugate Techniques" 2nd Edition, Academic Press, 2008. In some cases, the D-target protein can be attached to a detectable moiety, such as biotin. The contacting step may be performed where the L-peptidic library is in solution phase, or attached to a support such as a bead, a nanoparticle or an array, or displayed (e.g., on a phage particle).

Another aspect of the subject methods includes determining whether a compound of the L-peptidic libraries specifically bind to the D-target protein of interest. The determining step may be carried out using any one or more of a variety a protocols for characterizing the specific binding or the inhibition of binding. For example, the determining or assessment steps of ELISA assays, enzyme assays, or other related biological assay for assessing specific binding or the inhibition of binding. The determining step may include use of fluorescence, mass spectrometry, or other analytical methods used in immunoassays (e.g., colorimetric methods).

For example, the D-target may include a fluorescent label. Illustrative fluorescent labels include, for example, fluorescein isothiocyanate, didansyl chloride, lanthanides and lanthanide chelates, Alexafluor® dyes, inorganic semiconductor nanocrystals (e.g., quantum dots composed of or IIUV semiconductors), and similar labels. Any fluorescence emissions may be detected visually or may be detected using suitable instruments, such as fluorescence microscopes, fluorimeters, cameras, or instruments that include a charge coupled device, a photomultiplier tube, a diode array and the like. Other labels that emit light, e.g., phosphorescent labels, chemiluminescent labels, etc., may also be used and detected using similar techniques as those used in connection with fluorescence detection.

In some cases, a colorimetric label such as an enzyme, e.g., horseradish peroxidase, may be used. After an enzyme substrate, such as o-phenylenediamine dihydrochloride, is added to the enzyme a colored product is produced if the colorimetric label is present. The colored product may be detected visually or may be detected using suitable instruments such as, UV/visible instruments, plate readers, etc. In some examples, the colorimetric label may be a dye, e.g., an organic or an inorganic dye.

Other detectable markers that find use in the subject methods include a radiolabel. For example, the radiolabel may be integrated into the D-target or may be added as a tag to the species. Illustrative radiolabels include, but are not limited to, $^{3}H$, $^{14}C$, $^{32}P$, $^{33}P$, $^{35}S$ and $^{125}I$.

Specific binding of L-peptidic compounds to D-target proteins may be measured using mass spectrometry. For example, the above species may be allowed a sufficient time to associate and the contents (after optional washing steps) of a particular complex, if formed, may be removed and analyzed using mass spectroscopy. Numerous different mass spectrometric techniques may be used. For example, matrix-assisted laser desorbed ionization (MALDI), electrospray ionization (ESI), fast atom bombardment (FAB), time of flight (TOF), MALDI/TOF, ESI/TOF, chemical ionization (CI), liquid secondary ion mass spectrometry (LSIMS) or other mass spectrometric techniques may be used. In some examples, tandem mass spectrometry may be performed. Mass spectrometric techniques are useful for distinguishing between association and non-association. In examples where mass spectrometry is used, an array may be generated on an appropriate substrate (e.g., a metal plate for MALDI). Identification of L-peptidic compounds that specifically bind D-target proteins may be accomplished, for example, by comparing the spectrometry data against databases of the L-peptidic library and the target proteins.

Any convenient proximity assays to assess specific binding may also be used. For example, the immobilized D-target may be labeled with a radioactive label. The L-peptidic compounds may include fluorescent labels, such that if specific binding of the two species occurs, radioactive emission will excite the fluorescent label, and fluorescence emission may be detected as a positive indicator of association. In some embodiments, the L-peptidic library is immobilized and the labeled D-target is in solution. Because this energy transfer process requires the radioactive label and the fluorescent label to be close, e.g., within a few microns, fluorescently labeled species that are not specifically bound would not emit light. Such proximity methods have the added benefit that no washing steps or separation steps are required to determine if association occurs.

The subject screening methods may also include in silico methods, in which one or more physical and/or chemical attributes of compounds of the L-peptidic libraries are expressed in a computer-readable format and evaluated by any one or more of a variety of molecular modeling and/or analysis programs and algorithms suitable for this purpose In some embodiments, the in silico method includes inputting one or more parameters related to the D-target protein, such as but not limited to, the three-dimensional coordinates of a known X-ray crystal structure of the D-target protein. In some embodiments, the in silico method includes inputting one or more parameters related to the compounds of the L-peptidic library, such as but not limited to, the three-dimensional coordinates of a known X-ray crystal structure of a parent scaffold domain of the library. In some instances, the in silico method includes generating one or more parameters for each compound in a peptidic library in a computer readable format, and evaluating the capabilities of the compounds to specifically bind to the target protein. The in silico methods include, but are not limited to, molecular modelling studies, biomolecular docking experiments, and virtual representations of molecular structures and/or processes, such as molecular interactions. The in silico methods may be performed as a pre-screen (e.g., prior to preparing a L-peptidic library and performing in vitro screening), or as a validation of binding compounds identified after in vitro screening.

Any convenient phage display screening methods may be used in the subject methods to screen the L-peptidic libraries. Screening for the ability of a fusion polypeptide including a compound of the L-peptidic library to bind a target protein can be performed in solution phase. For example, a D-target protein can be attached with a detectable moiety, such as biotin. Phage that bind to the D-target protein in solution can be separated from unbound phage by a molecule that binds to the detectable moiety, such as streptavidin-coated beads where biotin is the detectable moiety. Affinity of binders (L-peptidic compound fusions that bind to D-target protein) can be determined based on concentration of the D-target protein used, using any convenient formulas and criteria.

In some embodiments, the D-target protein may be attached to a suitable support. After attachment of the D-target protein to the support, the immobilized D-target is contacted with the phage library expressing the L-peptidic compound containing fusion polypeptides under conditions suitable for binding of at least a portion of the phage particles with the immobilized D-target. Bound particles ("binders") to the immobilized D-target protein are separated from those particles that do not bind to the D-target by washing. Wash conditions can be adjusted to result in removal of all but the higher affinity binders. Binders may be dissociated from the immobilized D-target by a variety of methods. These methods include, but are not limited to, competitive dissociation using a known ligand, altering pH and/or ionic strength. Selection of L-peptidic binders may involve elution from an affinity matrix with a ligand. Elution with increasing concentrations of ligand should elute displayed binding L-peptidic compounds of increasing affinity.

The L-peptidic binders can be isolated and then reamplified or expressed in a host cell and subjected to another round of selection for binding of D-target protein. Any number of rounds of selection or sorting can be utilized. One of the selection or sorting procedures can involve isolating binders that bind to an antibody to a polypeptide tag, such as antibodies to the gD protein, FLAG or polyhistidine tags. Another selection or sorting procedure can involve multiple rounds of sorting for stability, such as binding to a target protein that specifically binds to folded L-peptidic compound and does not bind to unfolded polypeptide followed by selecting or sorting the stable binders for binding to the D-target protein.

In some cases, suitable host cells are infected with the binders and helper phage, and the host cells are cultured under conditions suitable for amplification of the phagemid particles. The phagemid particles are then collected and the selection process is repeated one or more times until L-peptidic binders having the desired affinity for the D-target protein are selected. In certain embodiments, two or more rounds of selection are conducted.

After L-peptidic binders are identified by binding to the D-target protein, the nucleic acid can be extracted. Extracted DNA can then be used directly to transform *E. coli* host cells or alternatively, the encoding sequences can be amplified, for example using PCR with suitable primers, and then inserted into a vector for expression.

One strategy to isolate high affinity binders is to bind a population of phage to an affinity matrix which contains a low amount of ligand. Phage displaying high affinity L-peptidic compound is bound and low affinity compounds are washed away. The high affinity L-peptidic compound is then recovered by elution with the ligand or by other procedures which elute the phage from the affinity matrix. In certain embodiments, the process of screening is carried out by automated systems to allow for high-throughput screening of library candidates.

In certain embodiments, the subject peptidic compounds specifically bind to a target protein with high affinity, e.g., as determined by an SPR binding assay or an ELISA assay. The subject peptidic compounds may exhibit an affinity for a target protein of 1 uM or less, such as 300 nM or less, 100 nM or less, 30 nM or less, 10 nM or less, 5 nM or less, 2 nM or less, 1 nM or less, 500 pM or less, or even less. The subject peptidic compounds may exhibit a specificity for a target protein, e.g., as determined by comparing the affinity of the compound for the target protein with that for a reference protein (e.g., an albumin protein), that is 5:1 or more 10:1 or more, such as 30:1 or more, 100:1 or more, 300:1 or more, 1000:1 or more, or even more.

As such, determining whether a L-peptidic compound of the library is capable of specifically binding a target protein may be carried out by any number of methods, as well as combinations thereof. Once a L-peptidic compound has been identified that specifically binds to the D-target protein, the D-enantiomer of the selected L-peptidic compound may be produced. The D-enantiomer of the selected L-peptidic compound can specifically bind to the L-enantiomer of the D-target protein.

The synthetic D-enantiomer of a polypeptide is capable of folding into a structure that is the mirror image of the corresponding L-polypeptide. This principle applies to both polypeptide ligands and to target proteins. Likewise, if a chiral ligand and target can specifically bind with each other to form a complex, then the enantiomers of the ligand and target also specifically bind to each other to form a mirror image complex with a structure that has mirror image symmetry to the original complex.

The D-peptidic compound may be prepared using any convenient method, e.g. solid phase peptide synthesis methods, solution phase peptide synthesis methods, native chemical ligation methods, or enzymatic ligation methods. In some embodiments, the D-peptidic compounds are prepared using stepwise solid phase peptide synthesis methods, e.g., such as the stepwise addition of amino acids in a solid-phase Merrifield-type synthesis. For the synthesis of a D-peptidic compound, D-amino acids or protected D-amino acids are utilized rather than the L-amino acids. Any convenient protecting group strategies that may be used such as, but not limited to, Fmoc solid-phase peptide synthesis and Boc solid-phase peptide synthesis strategies. In Boc solid-phase peptide synthesis a Boc-amino protecting group is used at the amino terminal and benzyl or benzyl-based protecting groups may be used for protection of sidechain functional groups. In Fmoc solid-phase peptide synthesis, a Fmoc-amino protecting group is used at the amino terminal and tert-butyl or benzyl-based protecting groups may be used for protection of sidechain functional groups.

In some embodiments, the D-peptidic compounds are prepared by the assembly of polypeptide building blocks using native chemical ligation methods. In some cases, two polypeptide fragments are first synthesized that contain termini adapted for chemical ligation. After stepwise chemical synthesis and cleavage from their respective solid phase resins, the two polypeptides are mixed and reacted to join the adapted termini and produce a larger, linear polypeptide that includes the two polypeptides.

Once the D-peptidic compound has been produced, it may be optionally purified or used without further purification. Purification may be performed using any convenient method, for example, using chromatography (e.g., RP-HPLC, ion exchange, affinity, and sizing column chromatography), centrifugation, differential solubility, or any other convenient technique for the purification of proteins.

In some cases, after synthesis or purification, the D-peptidic compound exists in a random coil or an unfolded state. The D-peptidic compound may then be folded using any convenient method, such that the D-peptidic compound folds from the random coil or unfolded state into a characteristic three-dimensional structure. In some cases, folding the D-peptidic compound includes dissolving the compound in an aqueous buffer under conditions that mimic physiological conditions (e.g., conditions of pH, ionic strength, temperature, and the like) and allowing the compound to fold into a characteristic three-dimensional structure in solution over a period of time (e.g., 2 days). The progress of folding of the D-peptidic compound may be followed using any convenient methods, such as HPLC, circular dichroism, etc. See, e.g., Boerema et al., ("Total synthesis by modern chemical ligation methods and high resolution (1.1 Å) X-ray structure of ribonuclease A," Peptide Science, 90(3), 278-286, 2008) for an exemplary folding method of a synthetic protein. The D-peptidic compound may form a structure that is the mirror image of that of a corresponding L-enantiomer.

In some cases, the subject method further includes screening the synthesized D-peptidic compound for specific binding to the L-enantiomer of the D-target protein. This L-target protein may be a naturally occurring, a recombinant or fusion protein containing a target protein, or a synthetic protein, which can be prepared using any convenient methods, such as recombinant expression methods or synthetic methods, or purchased commercially. Screening of the D-peptidic compound may be performed using a cell-based assay, an enzyme assay, a ELISA assay, a surface plasmon resonance (SPR) binding assay or other convenient biological assay for assessing specific binding or the inhibition of binding.

In certain embodiments, the subject method includes: (i) contacting a sample containing a D-target protein that is a hemagglutinin target protein, with a L-peptidic library; (ii) determining whether a L-peptidic compound of the library specifically binds to the D-target protein; and (iii) producing the D-peptidic compound of the selected L-peptidic compound, if such a compound was identified.

Vaccines

Hemagglutinin target proteins of the invention (e.g., HA mimics as described above) can be used in various ways. In one aspect, a L-peptidic hemagglutinin target protein can be used as a vaccine or immunogenic composition to enhance an individual's immune response (e.g., antibody response). Any of the hemagglutinin target proteins described herein may be adapted for use as a vaccine. In some cases, conjugates of a coiled coil mimic of hemagglutinin (i.e., "HA mimic conjugate") find use as a vaccine. It is understood that when the subject HA mimics (e.g., as described herein) are used in a vaccine composition then the HA mimics are L-peptidic, so as to elicit an immune response to the natural hemagglutinin. It is understood that when a subject HA mimic is used as a vaccine then the peptidic sequences that comprise the HA mimic are complexed together as a coiled coil, and may be conjugated to a carrier protein, via an optional linker. When the subject HA mimics are used as targets for screening for binding to GB1 peptidic compounds, the HA mimics may be utilized as either their L-peptidic or D-peptidic enantiomers.

The HA mimic conjugate is produced by adapting a first amino acid sequence of a naturally occurring alpha helical epitope into a heptad repeat to form a first templated epitope (e.g., as described herein); adapting a second sequence of a naturally occurring alpha helical epitope into a heptad repeat to form a second templated epitope; forming a complex of the two templated epitopes to create a coiled-coil structure, e.g., where the first and second template epitopes (e.g., as described herein) are connected via a covalent linker; and linking the coiled-coil structure to a carrier, such as a carrier protein, to form the conjugate. In one embodiment, the two templated epitopes have different sequences. The invention also encompasses a method of generating an immune response by administering the conjugate to a subject, such as a subject in need thereof. The conjugate is administered to the subject in a sufficient amount to create a protective immune response in the subject. In one embodiment, at least one of the epitopes is an HA epitope. In one embodiment, at least one of the epitopes is not derived from an influenza virus protein.

Any convenient carriers may be used in the subject conjugates. Any carrier that is suitable for use in humans or other mammals may be used. In some instances, the carrier used for the conjugate is a protein such as keyhole limpet hemocyanin (KLH), bovine serum albumin (BSA), ovalbumin, tetanus toxoid, cholera subunit B, protein D from *H. influenza*, or diphtheria toxoid, or a non-proteinaceous moiety such as the polysaccharide alginic acid (alginate). The carrier protein can enhance the immunogenicity of the peptide epitopes. In one aspect, the carrier used is a carrier that is approved by the Food and Drug Administration (FDA) for use in humans.

Any convenient linkers may be utilized to connect an HA mimic of interest and a carrier in the subject conjugates. The linkers are optional components affixed to the templated epitopes of the coiled coil scaffold. They serve to link Templated Epitope 1, and Templated Epitope 2, to the carrier protein. They can provide additional functionality; for example, they can act as spacers to ensure that the coiled coil complex is kept at a sufficient distance from the carrier protein so that the desired coiled coil conformation of the peptide epitopes is not altered by the carrier protein. Inclusion of a non-genetically coded amino acid, such as norleucine or alpha-amino-3-guanidino propionic acid, or another moiety which can be easily assayed without interference from genetically coded amino acids, provides a convenient method of assaying concentration of the conjugate in a given preparation.

Any convenient conjugation chemistry may be utilized to connect the linker to the carrier. Conjugation chemistries of interest include but are not limited to, maleimide, iodoacetamide, and active esters such as N-hydroxysuccinimide esters.

In some instances, the carrier may be positioned N-terminal or C-terminal relative to one of the two peptidic sequences of the HA coiled coil mimic. In some embodiments, the HA mimic conjugate is described by one of formulas (XII) and (XIII):

$$\begin{bmatrix} T^1-Z \\ | \\ L \\ | \\ T^2-Z \end{bmatrix}_n - C \quad \text{(XII)}$$

$$C - \begin{bmatrix} Z^1-T^1 \\ | \\ L \\ | \\ Z^2-T^2 \end{bmatrix}_n \quad \text{(XIII)}$$

where $Z^1$ and $Z^2$ are peptidic sequences that each independently include a HA epitope displayed on a coiled coil scaffold, $T^1$ and $T^2$ are optional tethers, L is a linker, n is an integer of 1 or more, and C is a carrier, and where C is attached via an optional linker to one of Z1, Z2, T1, T2 or L. In certain cases, n is an integer of 1 to 100, such as 1 to 50, 1 to 30, or 1 to 20. In certain instances, n is 2 or more, 5 or more, or 10 or more. In certain instances, n is 50 or less, 30 or less, or 20 or less.

In certain embodiments, in the conjugates of formulas (XII) and (XIII), $Z^1$ and $Z^2$ are identical sequences, such that the HA mimic is homologous. In other embodiments, in the conjugates of formulas (XII) and (XIII), $Z^1$ and $Z^2$ are different, such that the HA mimic is heterologous. $Z^1$ and $Z^2$ may include a heptad repeat sequence as described herein, e.g., as described in FIGS. 9-12.

Heterodimer HA mimic conjugates can be prepared from two different HA epitopes, such as H1 (from Group 1) and H5 (from Group 2). This immunogen is expected to elicit antibodies against the corresponding regions of both H1 and H5 proteins, providing protection of subjects against challenge with both H1 and/or H5 strains of influenza virus, and potentially against other influenza A viruses in both Groups 1 and 2. Such a hetero two-stranded immunogen is expected to provide broader protection against many different influenza strains, with potential effect as the long-sought-after, broadly protective universal influenza vaccine.

Methods of Inducing an Antibody Response

Aspects of the invention include a method of inducing an antibody response in a subject in need thereof. The method includes administering to the subject a L-peptidic hemagglutinin target protein in an amount sufficient to induce an antibody response in the subject. Any convenient methods and materials for inducing an antibody response in a subject may be utilized in the subject methods, including but not limited to, methods and materials as described by Hodges et al. in US2012/0009212, the disclosure of which is herein incorporated in its entirety. In some instances, the method includes administering an L-peptidic coiled coil hemagglutinin mimic (e.g., as described herein) to the subject in an amount sufficient to induce an antibody response in the subject. In certain embodiments, the coiled coil hemagglutinin mimic comprises a sequence having 70% or greater (such as 80% or greater, 90% or greater, or 95% or greater) amino acid sequence identity to one of SEQ ID NOs:124-139 of FIGS. 10-12.

The enhanced immune response is relative to what an individual's immune response would be without exposure to the HA mimic. In another aspect of the invention, the HA mimics can be used to induce an immune response (e.g., antibody response) in the individual being given the conjugate. For example, an individual's antibody response can be enhanced or induced by generating a greater quantity of antibody and/or antibodies that are more effective at neutralizing virus(es) and/or pathogen(s) of interest. The antibody response can also be enhanced or induced by the generation of antibodies that binds with greater affinity to their targets. In some instances, the antibodies generated are capable to binding to viral strain of various subtypes. Antibodies that are induced or enhanced by the use of the conjugates described herein can be directed to conformational epitopes as well as linear epitopes.

In other aspects, compositions comprising the HA mimics as described herein can be used to increase the number of plasma cells and/or memory B cells that can produce antibodies. Methods for measuring specific antibody responses include enzyme-linked immunosorbent assay (ELISA) and are well known in the art. See, e.g., Current Protocols in Immunology (J. E. Coligan et al., eds., 1991). In some aspects, the administration of the HA mimics described herein can induce cytokine production (e.g., IL-4, IL-5, and IL-13) that is helpful for antibody production. Cytokine concentrations can be measured, for example, by ELISA. These and other assays to evaluate the immune response to an immunogen are well known in the art. See, for example, SELECTED METHODS IN CELLULAR IMMUNOLOGY (1980) Mishell and Shiigi, eds., W.H. Freeman and Co, and/or Current Protocols in Immunology (J. E. Coligan et al., eds., 1991).

Accordingly, the conjugates described herein can be considered immunogenic compositions. In one aspect, the conjugates can be a component in an immunogenic composition. In another aspect, the conjugates can be a component in a vaccine composition. In some cases, the conjugates are used to induce or enhance an individual's immune response (e.g., antibody production or antibody response) such that the viral infection is reduced and in some cases, inhibited. Reduction of viral infection can be at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99% or 100% from the amount of infection that would have occurred had the immune response not been induced or enhanced. Any convenient assays for viral infection may be utilized.

In some instances, the conjugates are used to induce or enhance an individual's immune response (e.g., antibody production or antibody response) such that the viral replication is reduced and in some cases, inhibited. Reduction of viral replication can be at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99% or 100% from the amount of replication that would have occurred had the immune response not been induced or enhanced. Any convenient assays for viral replication may be utilized.

The amount of the conjugate when used as a vaccine, to be administered to an individual in need thereof can be determined by various factors, such as the type of viral infection, the biological and/or physiological response from the individual receiving the vaccine and other factors known to one of skill in the art. As such, the amount of the conjugate to be administered can be adjusted accordingly to achieve the desired beneficial effects. In one aspect, the amount of the conjugate to be used is at least about 1 ug conjugate/kg of the individual. In other aspects, the amount of the conjugate to be used is at least about 2 ug/kg, 3 ug/kg, 4 ug/kg, 5 ug/kg, 6 ug/kg, 7 ug/kg, 8 ug/kg, 9 ug/kg, 10 ug/kg, 11 ug/kg, 12 ug/kg, 13 ug/kg, 14 ug/kg, 15 ug/kg, 16 ug/kg, 17 ug/kg, 18 ug/kg, 19 ug/kg, 20 ug/kg, 21 ug/kg, 22 ug/kg, 23 ug/kg, 24 ug/kg, 25 ug/kg, 26 ug/kg, 27 ug/kg, 28 ug/kg, 29 ug/kg, or 30 ug/kg. In other aspects, the amount of the conjugate to be used is at least about 35 ug/kg, 40 ug/kg, 45 ug/kg, 50 ug/kg, 55 ug/kg, 60 ug/kg, 65 ug/kg, 70 ug/kg, 75 ug/kg, 80 ug/kg, 85 ug/kg, 90 ug/kg, 95 ug/kg or 100 ug/kg.

The subject conjugates may be administered in a variety of ways. In some instances, the conjugate is administered as an injectable compound. The injection can be by needle injection or needle-free injection (e.g., jet injection). In another aspect, the conjugate is administered by intranasal delivery. The conjugates can also be administered intramuscularly, subcutaneously, intradermally or some combination of all three.

The conjugates may be administered with various timing. Timing can be readily determined based on the individual's immune parameters. In some cases, a one-time administration is contemplated. In other cases, administering the conjugate more than once is contemplated, where the conjugate can be administered 2, 3, 4, 5, or more times.

The conjugates can be considered as a pharmaceutical composition and or an immunogenic composition. In addition to the other carriers described herein, pharmaceutically acceptable carriers may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. The HA mimic may also be lyophilized, for subsequent reconstitution and use. The vaccines can also include a carrier as described here. Examples of carriers which may be used include, but are not limited to, alum, microparticles, liposomes, and nanoparticles. The conjugates, immunogens, and vaccines can also be administered with adjuvants. Exemplary adjuvants include alum (Alhydrogel® (Superfos, Denmark; aluminum hydroxide)), and Freund's complete and incomplete adjuvants.

Pharmaceutical compositions can also include vaccines which are formulated for use to induce an immune response to influenza virus. In certain embodiments, the invention provides a vaccine comprising a coiled coil mimic of HA, such as a mimic described in one of FIGS. 10-12.

Antibody Compositions

Also provided are antibody compositions that include one or more antibodies raised to an HA mimic conjugate (e.g., as described herein). In some cases, the antibodies or antibody compositions are effective at neutralizing virus(es) and/or pathogen(s) of interest. In some cases, the antibodies bind specifically to their target epitopes, e.g., without undesirable off-target binding. In some instances, the antibodies generated are capable to binding to viral strain of various subtypes, e.g., an influenza A subtype as described herein. The subject antibodies can be directed to conformational epitopes as well as linear epitopes. The subject antibody compositions may be contained in a sample, and may be monoclonal or polyclonal. The antibodies may be produced by recombinant methods or may be purified from a sample. The subject antibodies may be induced in any convenient subject.

Compositions

As summarized above, also provided are compositions for identifying D-peptidic compounds that specifically bind target proteins. In some embodiments, the composition includes a D-target protein that is a hemagglutinin target protein and a library of L-peptidic compounds. In certain embodiments, the D-target protein is an enantiomer of a protein mimic of an influenza HA protein fragment, for example a mimic of the $HA_2$ region of HA as described above.

In certain embodiments, each compound of the L-peptidic library includes a scaffold domain and a distinct variable domain that includes at least 5 mutations. In certain embodiments, the L-peptidic library is a phage display library. In certain embodiments, the L-peptidic library is a GB1 peptidic library, e.g., a library as described in copending U.S. application entitled "GB1 peptidic libraries and methods of screening the same" filed on Nov. 10, 2011 to Sidhu et al. and accorded Ser. No. [13/294,072].

Utility

The methods, HA target proteins and D-peptidic compounds of the invention, e.g., as described above, find use in a variety of applications. Applications of interest include, but are not limited to: therapeutic applications, research applications, and screening applications.

Therapeutic applications of interest include applications where the activity of a target protein is the cause or a compounding factor in disease progression. As such, the D-peptidic compounds of the subject methods find use in the treatment of a variety of different disease conditions in which the modulation of L-target protein activity in the host is desired. In some embodiments, the disease condition is an infection with influenza A, such as but not limited to, H1N1, H2N2, H3N2, or H5N1, and the D-peptidic compounds modulate the activity of the influenza hemagglutinin protein. In some embodiments, the D-peptidic compounds of the subject methods find use as broad spectrum anti-viral agents. In some embodiments, the subject D-peptidic compounds have broad spectrum activity against Group 1 Influenza A viruses (e.g., one or more of H1, H2, H5, H6, H8 and H9 viruses). In some embodiments, the subject D-peptidic compounds have broad spectrum activity against Group 2 Influenza A viruses (e.g., one or more of H3, H4, H7 and H10 viruses). In some embodiments, a combination of the subject D-peptidic compounds may be used to neutralize both Group I and Group 2 Influenza A viruses.

Also of interest are therapeutic applications where the prevention or reduction of a viral infection are desired. HA target proteins of the invention find use in vaccine compositions and therapeutic compositions for prophylactic or active treatment of infected individuals.

The D-peptidic compounds of the subject methods find use in a variety of research applications. For example, analyzing the roles of target proteins in modulating various biological processes, including but not limited to, virus infection. Other molecules such as antibodies that bind target proteins have found use in similar areas of biological research. See e.g., Sidhu and Fellhouse, "Synthetic therapeutic antibodies," Nature Chemical Biology, 2006, 2(12), 682-688.

Diagnostic applications include but are not limited to, the development of clinical diagnostics, e.g., in vitro diagnostics or in vivo tumor imaging agents. The D-peptidic compounds find use in diagnosing or confirming diagnosis of a disease condition, or susceptibility thereto. The D-peptidic compounds are also useful in methods for monitoring disease progression and/or response to treatment in patients who have been previously diagnosed with the disease. Diagnostic applications of interest include diagnosis of disease conditions, such as but not limited to, influenza A (e.g., H1N1, H2N2, H3N2, or H5N1). In some cases, the disease condition is a target-mediated condition where the target is a hemagglutinin protein. Molecules that bind target proteins, such as aptamers and antibodies, have previously found use as clinical diagnostic reagents, see for example, Jayasena, "Aptamers: An Emerging Class of Molecules That Rival Antibodies in Diagnostics," Clinical Chemistry. 1999; 45: 1628-1650.

The subject methods, e.g., as described above, find use in a variety of applications, including the production of D-peptidic compounds for a wide range of research and therapeutic applications, such as lead identification and affinity maturation, identification of diagnostic reagents, development of high throughput screening assays, development of drug delivery systems for the delivery of toxins or other therapeutic moieties, and vaccine applications. The subject methods may be exploited in multiple settings. The screening of peptide libraries has found use in the development of lead D-peptides as therapeutic agents, see Welch et al., "Potent D-peptide inhibitors of HIV-1 entry," PNAS, 2007, 104(43), 16828-16833.

The following examples are offered by way of illustration and not by way of limitation.

EXPERIMENTAL

Synthesis of Target Protein

D-target proteins are synthesized utilizing standard solid phase peptide synthesis (SPPS) and/or native chemical ligation methods (see e.g., review by Ackrill et al., Biopolymers (Pept Sci) 94: 495-503, 2010).

Antibody Binding of HA Mimics

The binding of HA mimics to influenza neutralizing antibodies is assessed using ELISA and SPR assays.

Phage Display of GB1 Peptidic Libraries

Cloning

The wild-type sequence of the Protein G B1 domain (Gronenborn et al., Science 253, 657-61, 1991) was prepared (Genscript USA Inc.) with an N-terminal FLAG tag and a C-terminal 10×His tag spaced by a Glycine-Glycine-Serine linker, is shown below:

```
                                          (SEQ ID NO: 5)
DYKDDDDK-GGS-TYKLILNGKTLKGETTTEAVDAATAEKVFKQYANDNG

VDGEWTYDDATKTFTVTE-GGS-HHHHHHHHHH-amber stop
```

This sequence was synthesized with NcoI and XbaI restriction sites at 5' and 3' respectively and cloned into a display vector as an N-terminal fusion to truncated protein 3 of M13 filamentous phage. The features of the vector include a ptac promoter and StII secretion leader sequence (MKKNIAFLLASMFVFSIATNAYA; SEQ ID NO: 6). This display version allows the display of GB1 in amber suppressor bacterial strains and is useful for expression of the protein in non-suppressor strains.

Optimization of Phage Display Levels

The presence of the His-tag and amber-stop at the C-terminus of the protein allows the purification of proteins/mutants without additional mutagenesis. In addition, to optimize for display of GB1 peptidic compounds, two additional constructs were tested for display-levels of GB1 (i) without His-tag and amber-stop (ii) with a hinge and dimerization sequence derived from a Fab-template (DKTHTCGRP; SEQ ID NO: 7) for dimeric display.

The following oligonucleotides were prepared (Integrated DNA Technologies Inc.), for site-directed mutagenesis:

i) 5'-<u>GTT ACC GAA GGC GGT TCT TCT AGA AGT GGT TCC GGT</u>-3'　　　SEQ ID NO: 8
　　　V　T　E　G　G　S　S　R　S　G　S　G　　　　　　　　　　　　SEQ ID NO: 9
　For removal of 10xHis and amber-stop ii) 5'-<u>TT ACC GAA GGC GGT TCT</u> GAC AAA ACT CAC ACA TGC GGC CGG CCC <u>AGT GGT TCC</u>　SEQ ID NO: 10
　　GGT GAT T-3'
　　　V　T　E　G　G　S　D　K　T　H-　　　　　　　　　　　　　　　SEQ ID NO: 11
　　T　C　G　R　P　S　G　S　G
　D　F
　For insertion of Fab-dimerization sequence to replace
　His-tag and amber stop Site-directed mutagenesis was performed by methods described by Kunkel et al. (Methods Enzymol., 1987, 154, 367-82) and the sequence was confirmed by DNA sequencing. For comparing display levels, phage for each construct was harvested from a 25 mL overnight culture using methods described previously (Fellouse & Sidhu, "Making antibodies in bacteria. Making and using antibodies" Howard & Kaser, Eds., CRC Press, Boca Raton, Fla., 2007). The phage concentrations were estimated using a spectrophotometer ($OD_{268}$=1 for $5\times10^{12}$ phage/ml) and normalized to the lowest concentration. Three-fold serial dilutions of phage for each construct were prepared and added to NUNC maxisorb plates previously coated with anti-FLAG antibody (5 μg/ml) and blocked with BSA (0.2% BSA in PBS). The plates were washed and assayed with anti-M13-HRP to detect binding. The HRP signal was plotted as function of phage concentration.

Preparation of GB1 Peptidic Libraries

The solvent accessible surface area (SASA) for each residue in the Protein Data Bank (PDB) structure 3 GB1 was estimated using the GETarea tool (Fraczkiewicz & Braun, "Exact and efficient analytical calculation of the accessible surface areas and their gradients for macromolecules," J. Comput. Chem. 1998, 19, 319-333). This tool also calculates the ratio of SASA in structure compared to SASA in a random coil. A ratio of 0.4 was used to identify solvent exposed residues (shown in bold):

(SEQ ID NO:1)
TYKLILNGKTLKGETTTEAVDAATAEKVFKQYANDNGVDGEWTYDDATKT
FTVTE.

Various contiguous stretches of solvent-accessible residues were selected for randomization (shown in red in FIGS. 2 to 7) taking into account the oligonucleotide length and homology requirements for Kunkel mutagenesis. The parent sequence is also shown in FIG. 1 with the numbering scheme and loop/beta-turn regions defined.

In addition, positions in the loops were selected for mutations that include insertion of 0, 1 or 2 additional amino acid residues in addition to substitution. Library 1: +0-2 insertions at position 38; Library 2: +0-2 insertions at position 19; Library 3: +2 insertions at position 1, +0-2 insertions at positions 19 and 47; Library 4: +0-2 insertions at positions 9 and 38, +1 insertion at position 55; Library 5: +0-2 insertions at position 9, +1 insertion at position 55; Library 6: +1 insertion at position 1, +0-2 insertions at position 47.

The following oligonucleotides were prepared (Integrated DNA Technologies) to make the libraries using the Kunkel mutagensis method:

Library 1:

(SEQ ID NO: 12)
5'-<u>ACGACCGAAGCAGTG</u> KHT KHT KHT KHT GCA KHT KHT GTT TTC KHT KHT

TAC GCC KHT KHT AAT KHT KHT KHT KHT KHT <u>TGGACCTACGATGAT</u>-3'

(SEQ ID NO: 13)
5'-<u>ACGACCGAAGCAGTG</u> KHT KHT KHT KHT GCA KHT KHT GTT TTC KHT KHT

TAC GCC KHT KHT AAT KHT KHT KHT KHT KHT KHT <u>TGGACCTACGATGAT</u>-3'

(SEQ ID NO: 14)
5'-<u>ACGACCGAAGCAGTG</u> KHT KHT KHT KHT GCA KHT KHT GTT TTC KHT KHT

TAC GCC KHT KHT AAT KHT KHT KHT KHT KHT KHT <u>TGGACCTACGATGAT</u>-3'

These oligonucleotides include the variable regions where each variant amino acid position is encoded by a KHT codon. SEQ ID NOs: 12-14 include mutations of +0, 1 or 2 additional variant amino acids, respectively, at the position equivalent to position 38 of the scaffold.

Library 2:

(SEQ ID NO: 15)
5'-<u>GGTGAAACCACGACC</u> KHT KHT KHT KHT KHT KHT KHT GCA KHT KHT KHT

TTC KHT KHT KHT GCC KHT KHT <u>AATGGCGTGGATGGT</u>-3'

```
                                                          (SEQ ID NO: 16)
5'-GGTGAAACCACGACC KHT KHT KHT KHT KHT KHT KHT KHT GCA KHT KHT

KHT TTC KHT KHT KHT GCC KHT KHT AATGGCGTGGATGGT-3'

(SEQ ID NO: 17)
5'-GGTGAAACCACGACC KHT KHT KHT KHT KHT KHT KHT KHT KHT GCA KHT

KHT KHT TTC KHT KHT KHT GCC KHT KHT AATGGCGTGGATGGT-3'
```

These oligonucleotides include the variable regions where each variant amino acid position is encoded by a KHT codon. SEQ ID NOs: 15-17 include insertion mutations of +0, 1 or 2 additional variant amino acids, respectively, at the position equivalent to position 19 of the scaffold.

Library 3:

```
                                                          (SEQ ID NO: 18)
5'-GATGATAAAGGCGGTAGC KHT KHT KHT TACAAACTGATTCTGAAC-3'

(SEQ ID NO: 19)
5'-AAAGGTGAAACCACGACC KHT KHT KHT KHT KHT KHT KHT

GCAGAAAAGTTTTCAAA-3'

(SEQ ID NO: 20)
5'-AAAGGTGAAACCACGACC KHT KHT KHT KHT KHT KHT KHT KHT

GCAGAAAAGTTTTCAAA-3'

(SEQ ID NO: 21)
5'-AAAGGTGAAACCACGACC KHT KHT KHT KHT KHT KHT KHT KHT KHT

GCAGAAAAGTTTTCAAA-3'

(SEQ ID NO: 22)
5'-GATGGTGAATGGACCTAC KHT KHT KHT KHT KHT
ACCTTCACGGTTACCGAA-3'

(SEQ ID NO: 23)
5'-GATGGTGAATGGACCTAC KHT KHT KHT KHT KHT KHT

ACCTTCACGGTTACCGAA-3'

(SEQ ID NO: 24)
5'-GATGGTGAATGGACCTAC KHT KHT KHT KHT KHT KHT KHT

ACCTTCACGGTTACCGAA-3'
```

These oligonucleotides include the variable regions where each variant amino acid position is encoded by a KHT codon. SEQ ID NO: 18 includes an insertion mutation of +2 variant amino acids at the position equivalent to position 1 of the scaffold. SEQ ID NOs: 19-21 include mutations of +0, 1 or 2 additional variant amino acids, respectively, at the position equivalent to position 19 of the scaffold. SEQ ID NOs: 22-24 include mutations of +0, 1 or 2 additional variant amino acids, respectively, at the position equivalent to position 47 of the scaffold.

Library 4

```
                                                          (SEQ ID NO: 25)
5'-ACGTACAAACTGATTCTG KHT KHT KHT KHT KHT

KHT GGTGAAACCACGACCGAA-3'

(SEQ ID NO: 26)
5'-ACGTACAAACTGATTCTG KHT KHT KHT KHT KHT

KHT KHT GGTGAAACCACGACCGAA-3'

(SEQ ID NO: 27)
5'-ACGTACAAACTGATTCTG KHT KHT KHT KHT KHT

KHT KHT KHT GGTGAAACCACGACCGAA-3'

(SEQ ID NO: 28)
5'-AAACAGTACGCCAACGAT KHT KHT KHT KHT KHT

KHT TGGACCTACGATGATGCG-3'

(SEQ ID NO: 29)
5'-AAACAGTACGCCAACGAT KHT KHT KHT KHT KHT

KHT KHT TGGACCTACGATGATGCG-3'

(SEQ ID NO: 30)
5'-AAACAGTACGCCAACGAT KHT KHT KHT KHT KHT

KHT KHT KHT TGGACCTACGATGATGCG-3'

(SEQ ID NO: 31)
5'-ACGAAAACCTTCACGGTT KHT KHT KHT

GGCGGTTCTGACAAAACT-3'
```

These oligonucleotides include the variable regions where each variant amino acid position is encoded by a KHT codon. SEQ ID NOs: 25-27 include mutations of +0, 1 or 2 additional variant amino acids, respectively, at the position equivalent to position 9 of the scaffold. SEQ ID NOs: 28-30 include mutations of +0, 1 or 2 additional variant amino acids, respectively, at the position equivalent to position 38 of the scaffold. SEQ ID NO: 31 includes an insertion mutation of +2 variant amino acids at the position equivalent to position 55 of the scaffold.
Library 5

```
                                                      (SEQ ID NO: 32)
5'-AAAGGCGGTAGCACGTAC KHT CTG KHT CTG KHT KHT KHT KHT KHT KHT KHT

KHT ACC KHT ACCGAAGCAGTGGATGCA-3'

(SEQ ID NO: 33)
5'-AAAGGCGGTAGCACGTAC KHT CTG KHT CTG KHT KHT KHT KHT KHT KHT KHT

KHT KHT ACC KHT ACCGAAGCAGTGGATGCA-3'

(SEQ ID NO: 34)
5'-AAAGGCGGTAGCACGTAC KHT CTG KHT CTG KHT KHT KHT KHT KHT KHT KHT

KHT KHT KHT ACC KHT ACCGAAGCAGTGGATGCA-3'

(SEQ ID NO: 35)
5'-GATGCGACGAAAACCTTC KHT GTT KHT KHT KHT GGCGGTTCTGACAAAACT-3'
```

These oligonucleotides include the variable regions where each variant amino acid position is encoded by a KHT codon. SEQ ID NOs: 32-34 include mutations of +0, 1 or 2 additional variant amino acids, respectively, at the position equivalent to position 9 of the scaffold. SEQ ID NO: 35 includes an insertion mutation of +2 variant amino acids at the position equivalent to position 55 of the scaffold.
Library 6

```
                                                      (SEQ ID NO: 36)
5'-GATGATAAAGGCGGTAGC KHT KHT TAC KHT CTG KHT CTG KHT

GGCAAAACCCTGAAAGGT-3'

(SEQ ID NO: 37)
5'-GATAATGGCGTGGATGGT KHT TGG KHT TAC KHT KHT KHT KHT KHT KHT TTC

KHT GTT KHT GAAGGCGGTTCTGACAAA-3'

(SEQ ID NO: 38)
5'-GATAATGGCGTGGATGGT KHT TGG KHT TAC KHT KHT KHT KHT KHT KHT KHT

TTC KHT GTT KHT GAAGGCGGTTCTGACAAA-3'

(SEQ ID NO: 39)
5'-GATAATGGCGTGGATGGT KHT TGG KHT TAC KHT KHT KHT KHT KHT KHT KHT

KHT TTC KHT GTT KHT GAAGGCGGTTCTGACAAA-3'
```

These oligonucleotides include the variable regions where each variant amino acid position is encoded by a KHT codon. SEQ ID NO: 36 includes an insertion mutation of +1 variant amino acids at the position equivalent to position 1 of the scaffold. SEQ ID NOs: 37-38 include mutations of +0, 1 or 2 additional variant amino acids, respectively, at the position equivalent to position 47 of the scaffold.

The libraries were prepared using the same method described above for the GB1 template with Fab dimerization sequence (Fellouse & Sidhu, 2007). Oligonucleotides with 0/1/2 insertions have the same homology regions and compete for binding the template. Therefore they were pooled together (equimolar ratio) and treated as a single oligonucleotide for mutagenesis. The constructed libraries were pooled together for total diversity of $3.5 \times 10^{10}$ transformants.

Methods of Screening of Phage Display Libraries

Library Selections Against D-Target Protein and Negative Selection with BSA

The selection procedure is essentially the same as described in previous protocols (Fellouse & Sidhu, 2007) with some minor changes. The method below can be adapted to screen for binding to any target. The media and buffer recipes are the same as in the described protocol. Phage display libraries 1 to 6 prepared as described above are selected for binding to D-target protein according to the following method.

1. Coat NUNC Maxisorb plate wells with 100 µl of D-target protein (5 µg/ml in PBS) for 2 h at room temperature. Coat 5 wells for selection and 1 well for phage pool ELISA.

2. Remove the coating solution and block for 1 h with 200 µl of PBS, 0.2% BSA. At the same time, block an uncoated well as a negative control for pool ELISA. Also block 7 wells for pre-incubation of library on a separate plate.

3. Remove the block solution from the pre-incubation plate and wash four times with PT buffer.

4. Add 100 µl of library phage solution (precipitated and resuspended in PBT buffer) to each blocked wells. Incubate at room temperature for 1 h with gentle shaking.

5. Remove the block solution from selection plate and wash four times with PT buffer.

6. Transfer library phage solution from pre-incubation plate to selection plate (5 selection wells+2 controls for pool ELISA)

7. Remove the phage solution and wash 8-10 times with PT buffer (increased based pool ELISA signal from previous round).

8. To elute bound phage from selection wells, add 100 µl of 100 mM HCl. Incubate 5 min at room temperature. Transfer the HCl solution to a 1.5-ml microfuge tube. Adjust to neutral pH with 11 µl of 1.0 M Tris-HCl, pH 11.0.

9. In the meantime add 100 μl of anti-M13 HRP conjugate (1:5000 dilution in PBT buffer) to the control wells and incubate for 30 min.
10. Wash control wells four times with PT buffer. Add 100 μl of freshly prepared TMB substrate. Allow color to develop for 5-10 min.
11. Stop the reaction with 100 μl of 1.0 M $H_3PO_4$ and read absorbance at 450 nm in a microtiter plate reader. The enrichment ratio can be calculated as the ratio of signal from coated vs uncoated well.
12. Add 250 μl eluted phage solution to 2.5 ml of actively growing E. coli XL1-Blue ($OD_{600}$<0.8) in 2YT/tet medium. Incubate for 20 min at 37° C. with shaking at 200 rpm.
13. Add M13KO7 helper phage to a final concentration of $10^{10}$ phage/ml. Incubate for 45 min at 37° C. with shaking at 200 rpm.
14. Transfer the culture from the antigen-coated wells to 25 volumes of 2YT/carb/kan medium and incubate overnight at 37° C. with shaking at 200 rpm.
15. Isolate phage by precipitation with PEG/NaCl solution, resuspend in 1.0 ml of PBT buffer
16. Repeat the selection cycle for 4 rounds.

Negative Selection with GST Tagged Protein

A more stringent negative selection procedure is as follows. The selection process is essentially the same as described above except that:
i) For Rounds 1 and 2 the libraries are pre-incubated on GST coated (10 μg/ml in PBS) and blocked wells.
ii) For Rounds 3 and 4, the libraries are pre-incubated with 0.2 mg/ml GST in solution for 1 hr before transfer to selection wells
iii) The control wells for pool ELISA are coated with GST (5 μg/ml in PBS)

Analysis of Single-Clones by Direct Binding ELISA

The following protocol is an adapted version of previous protocols (Fellouse & Sidhu 2007; Tonikian et al., "Identifying specificity profiles for peptide recognition modules from phage-displayed peptide libraries," Nat. Protoc., 2007, 2, 1368-86), and is used to analyse clones identified by selection of Libraries 1 to 6 against D-target protein as described above:
1. Inoculate 450 μl aliquots of 2YT/carb/KO7 medium in 96-well microtubes with single colonies harboring phagemids and grow for 21 hrs at 37° C. with shaking at 200 rpm.
2. Centrifuge at 4,000 rpm for 10 min and transfer phage supernatants to fresh tubes.
3. Coat 3 wells of a 384 well NUNC maxisorb plate per clone, with 2 μg/ml of D-target protein, Neutravidn, Erbin-GST respectively and leave one well uncoated. Incubate for 2 hrs at room temperature and block the plates (all 4 well).
4. Wash the plate four times with PT buffer.
5. Transfer 30 μl of phage supernatant to each well and incubate for 2 hrs at room temperature with gentle shaking. 10 nM or 100 nM D-target protein may be added to binding solutions for a competition binding assay.
6. Wash four times with PT buffer.
7. Add 30 μl of anti-M13-HRP conjugate (diluted 1:5000 in PBT buffer). Incubate 30 min with gentle shaking.
8. Wash four times with PT buffer
9. Add 30 μl of freshly prepared TMB substrate. Allow color to develop for 5-10 min.
10. Stop the reaction with 100 μl of 1.0 M $H_3PO_4$ and read absorbance at 450 nm in a microtiter plate reader.

Binding Affinity by SPR

Binding affinities are measured using the Biacore SPR system. SPR analysis is performed on a ProteOn XPR36 Protein Interaction Array System (BioRad). Chemically synthesized target protein is immobilized in 50 mM Sodium Acetate (pH 5.5) to a non-dilute EDAC/sulfo-NHS activated GLC surface on separate channels using a flow rate of 30 ml/min for 5 minutes in the vertical direction. Immobilization levels are monitored to ensure immobilization of approximately 500 response units of each protein. The domains are then stabilized with PBS for 30 seconds and 0.85% $H_3PO_4$ for 18 seconds each at 100 ml/min.

Target-binding compounds are diluted in PBS plus 0.05% Tween 20 at a starting concentration of 200 nM. The binders are further diluted with PBST 2-fold in series to produce 5 concentrations of compounds. A PBST blank is also included. The injection parameters are: 100 ml/min, 60 seconds contact time, and 600 seconds dissociation time, in the horizontal direction. Target proteins are regenerated with an injection of 0.85% $H_3PO_4$ at a flow rate of 100 ml/min followed by a PBST wash of 30 seconds at 100 ml/min flow rate.

Although the particular embodiments have been described in some detail by way of illustration and example for purposes of clarity of understanding, it is readily apparent in light of the teachings of this invention that certain changes and modifications may be made thereto without departing from the spirit or scope of the appended claims.

Accordingly, the preceding merely illustrates the principles of the invention. Various arrangements may be devised which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method comprising:
   a) contacting a D-peptidic hemagglutinin target protein with a library of L-peptidic compounds;
   wherein the D-peptidic hemagglutinin target protein is described by one of formulas (X) and (XI):

$$\begin{array}{c} T^1-Z^1 \\ | \\ L \\ | \\ T^2-Z^2 \end{array} \quad (X)$$

$$\begin{array}{c} Z^1-T^1 \\ | \\ L \\ | \\ Z^2-T^2 \end{array} \quad (XI)$$

wherein:
   $Z^1$ and $Z^2$ each comprise the D-enantiomer of a peptidic hemagglutinin epitope independently selected from one of SEQ ID NOs:87-102 and displayed on a coiled coil scaffold;
   $T^1$ and $T^2$ are optional tethers; and
   L is a linker;
   b) identifying a L-peptidic compound of the library that specifically binds to the D-peptidic hemagglutinin target protein; and
   c) producing the enantiomer of the identified L-peptidic compound.

2. The method according to claim 1,
   wherein $Z^1$ and $Z^2$ each comprise the D-enantiomer of a peptidic hemagglutinin epitope selected from:
   H1: QKSaQNdIDGaTSdVNSaIEd (SEQ ID NO:87);
   H2: KESaQKdIDGaTNdVNSaIEd (SEQ ID NO:88);
   H5: KESaQKdIDGaTNdVNSaIDd (SEQ ID NO:91);
   H6: RESaQKdVDGaTNdVNSaIDd (SEQ ID NO:92);
   H8: QKSaQEdIDKaTNdVNNaVDd (SEQ ID NO:94);
   H9: KGSaQKdIDKaTSdVNNaIDd (SEQ ID NO:95); and
   wherein "a" and "d" are each independently selected from Leu, Ile, Ala, Phe and Val.

3. The method according to claim 2, wherein $Z^1$ and $Z^2$ each comprise SEQ ID NO:87.

4. The method according to claim 3, wherein the D-peptidic hemagglutinin target protein is:
   biotin-nle--iaalqksiqnlidGitslvnsiielmntcrr-amide (SEQ ID NO:78)
   Ac-iaalqksiqnlidGitslvnsiielmntcrr-amide (SEQ ID NO:79).

5. The method according to claim 1, wherein the library is a phage display library.

6. The method according to claim 5, wherein each compound of the library is a GB1 peptidic compound.

7. The method according to claim 1, further comprising screening the enantiomer of the identified L-peptidic compound for specific binding to a L-peptidic hemagglutinin protein.

8. The method according to claim 3, wherein "a" and "d" are independently Ile or Leu.

9. The method according to claim 2, wherein $Z^1$ and $Z^2$ each comprise SEQ ID NO:88.

10. The method according to claim 9, wherein "a" and "d" are independently Ile or Leu.

11. The method according to claim 2, wherein $Z^1$ and $Z^2$ each comprise SEQ ID NO:91.

12. The method according to claim 11, wherein "a" and "d" are independently Ile or Leu.

13. The method according to claim 2, wherein $Z^1$ and $Z^2$ each comprise SEQ ID NO:92.

14. The method according to claim 13, wherein "a" and "d" are independently Ile or Leu.

15. The method according to claim 2, wherein $Z^1$ and $Z^2$ each comprise SEQ ID NO:94.

16. The method according to claim 15, wherein "a" and "d" are independently Ile or Leu.

17. The method according to claim 2, wherein $Z^1$ and $Z^2$ each comprise SEQ ID NO:95.

18. The method according to claim 17, wherein "a" and "d" are independently Ile or Leu.

19. The method according to claim 1, wherein $Z^1$ or $Z^2$ comprises a biotin group.

* * * * *

SEQUENCE LISTING

<160> NUMBER OF SEQ ID NOS: 178

<210> SEQ ID NO 1
<211> LENGTH: 55
<212> TYPE: PRT
<213> ORGANISM: Artificial Sequence
<220> FEATURE:
<223> OTHER INFORMATION: Synthetic polypeptide

<400> SEQUENCE: 1

Thr Tyr Lys Leu Ile Leu Asn Gly Lys Thr Leu Lys Gly Glu Thr Thr
1               5                   10                  15

Thr Glu Ala Val Asp Ala Ala Thr Ala Glu Lys Val Phe Lys Gln Tyr
            20                  25                  30

Ala Asn Asp Asn Gly Val Asp Gly Glu Trp Thr Tyr Asp Asp Ala Thr
        35                  40                  45

Lys Thr Phe Thr Val Thr Glu
    50                  55

<210> SEQ ID NO 2
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 2

Thr Tyr Lys Leu Ile Leu Asn Gly Lys Thr Leu Lys Gly Glu Thr Thr
1               5                   10                  15

Thr Glu Ala

<210> SEQ ID NO 3
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 3

Thr Tyr Asp Asp Ala Thr Lys Thr Phe Thr Val Thr Glu
1               5                   10

<210> SEQ ID NO 4
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 4

Val Asp Ala Ala Thr Ala Glu Lys Val Phe Lys Gln Tyr Ala Asn Asp
1               5                   10                  15

Asn Gly Val Asp Gly Glu Trp
            20

<210> SEQ ID NO 5
<211> LENGTH: 79
<212> TYPE: PRT
<213> ORGANISM: Artificial Sequence
<220> FEATURE:
<223> OTHER INFORMATION: Synthetic polypeptide

<400> SEQUENCE: 5

Asp Tyr Lys Asp Asp Asp Lys Gly Gly Ser Thr Tyr Lys Leu Ile
1               5                   10                  15

Leu Asn Gly Lys Thr Leu Lys Gly Glu Thr Thr Thr Glu Ala Val Asp
            20                  25                  30

Ala Ala Thr Ala Glu Lys Val Phe Lys Gln Tyr Ala Asn Asp Asn Gly
        35                  40                  45

Val Asp Gly Glu Trp Thr Tyr Asp Asp Ala Thr Lys Thr Phe Thr Val

```
                    50                  55                  60
Thr Glu Gly Gly Ser His His His His His His His His
 65                  70                  75

<210> SEQ ID NO 6
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 6

Met Lys Lys Asn Ile Ala Phe Leu Leu Ala Ser Met Phe Val Phe Ser
 1               5                  10                  15

Ile Ala Thr Asn Ala Tyr Ala
            20

<210> SEQ ID NO 7
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 7

Asp Lys Thr His Thr Cys Gly Arg Pro
 1               5

<210> SEQ ID NO 8
<211> LENGTH: 36
<212> TYPE: PRT
<213> ORGANISM: Artificial Sequence
<220> FEATURE:
<223> OTHER INFORMATION: Synthetic polypeptide

<400> SEQUENCE: 8

Gly Thr Thr Ala Cys Cys Gly Ala Ala Gly Gly Cys Gly Gly Thr Thr
 1               5                  10                  15

Cys Thr Thr Cys Thr Ala Gly Ala Ala Gly Thr Gly Gly Thr Thr Cys
            20                  25                  30

Cys Gly Gly Thr
        35

<210> SEQ ID NO 9
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 9

Val Thr Glu Gly Gly Ser Ser Arg Ser Gly Ser Gly
 1               5                  10

<210> SEQ ID NO 10
<211> LENGTH: 60
<212> TYPE: PRT
<213> ORGANISM: Artificial Sequence
<220> FEATURE:
<223> OTHER INFORMATION: Synthetic polypeptide

<400> SEQUENCE: 10

Thr Thr Ala Cys Cys Gly Ala Ala Gly Gly Cys Gly Gly Thr Thr Cys
 1               5                  10                  15
```

```
Thr Gly Ala Cys Ala Ala Ala Ala Cys Thr Cys Ala Cys Ala
         20                  25                  30

Thr Gly Cys Gly Gly Cys Gly Gly Cys Cys Ala Gly Thr Gly
         35                  40                  45

Gly Thr Thr Cys Cys Gly Gly Thr Gly Ala Thr Thr
         50                  55                  60

<210> SEQ ID NO 11
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 11

Val Thr Glu Gly Gly Ser Asp Lys Thr His Thr Cys Gly Arg Pro Ser
1               5                   10                  15

Gly Ser Gly Asp Phe
            20

<210> SEQ ID NO 12
<211> LENGTH: 93
<212> TYPE: DNA
<213> ORGANISM: Artificial Sequence
<220> FEATURE:
<223> OTHER INFORMATION: Synthetic polynucleotide

<400> SEQUENCE: 12
acgaccgaag cagtgkhtkh tkhtkhtgca khtkhtgttt tckhtkhtta cgcckhtkht      60
aatkhtkhtk htkhtkhttg gacctacgat gat                                  93

<210> SEQ ID NO 13
<211> LENGTH: 96
<212> TYPE: DNA
<213> ORGANISM: Artificial Sequence
<220> FEATURE:
<223> OTHER INFORMATION: Synthetic polynucleotide

<400> SEQUENCE: 13
acgaccgaag cagtgkhtkh tkhtkhtgca khtkhtgttt tckhtkhtta cgcckhtkht      60
aatkhtkhtk htkhtkhtkh ttggacctac gatgat                               96

<210> SEQ ID NO 14
<211> LENGTH: 99
<212> TYPE: DNA
<213> ORGANISM: Artificial Sequence
<220> FEATURE:
<223> OTHER INFORMATION: Synthetic polynucleotide

<400> SEQUENCE: 14
acgaccgaag cagtgkhtkh tkhtkhtgca khtkhtgttt tckhtkhtta cgcckhtkht      60
aatkhtkhtk htkhtkhtkh tkhttggacc tacgatgat                            99

<210> SEQ ID NO 15
<211> LENGTH: 84
<212> TYPE: DNA
<213> ORGANISM: Artificial Sequence
<220> FEATURE:
<223> OTHER INFORMATION: Synthetic polynucleotide

<400> SEQUENCE: 15
ggtgaaacca cgacckhtkh tkhtkhtkht khtkhtgcak htkhtkhttt ckhtkhtkht      60
```

```
gcckhtkhta atggcgtgga tggt                                    84

<210> SEQ ID NO 16
<211> LENGTH: 87
<212> TYPE: DNA
<213> ORGANISM: Artificial Sequence
<220> FEATURE:
<223> OTHER INFORMATION: Synthetic polynucleotide

<400> SEQUENCE: 16
ggtgaaacca cgacckhtkh tkhtkhtkht khtkhtkhtg cakhtkhtkh tttckhtkht    60
khtgcckhtk htaatggcgt ggatggt                                 87

<210> SEQ ID NO 17
<211> LENGTH: 90
<212> TYPE: DNA
<213> ORGANISM: Artificial Sequence
<220> FEATURE:
<223> OTHER INFORMATION: Synthetic polynucleotide

<400> SEQUENCE: 17
ggtgaaacca cgacckhtkh tkhtkhtkht khtkhtkhtk htgcakhtkh tkhtttckht    60
khtkhtgcck htkhtaatgg cgtggatggt                              90

<210> SEQ ID NO 18
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 18
gatgataaag gcggtagckh tkhtkhttac aaactgattc tgaac            45

<210> SEQ ID NO 19
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 19
aaaggtgaaa ccacgacckh tkhtkhtkht khtkhtkhtg cagaaaaagt tttcaaa      57

<210> SEQ ID NO 20
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 20
aaaggtgaaa ccacgacckh tkhtkhtkht khtkhtkhtk htgcagaaaa agttttcaaa   60

<210> SEQ ID NO 21
<211> LENGTH: 63
<212> TYPE: DNA
<213> ORGANISM: Artificial Sequence
<220> FEATURE:
<223> OTHER INFORMATION: Synthetic polynucleotide

<400> SEQUENCE: 21
aaaggtgaaa ccacgaccka tkhtkhtkht khtkhtkhtk htkhtgcaga aaaagttttc   60
aaa                                                           63
```

<210> SEQ ID NO 22
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 22
gatggtgaat ggacctackh tkhtkhtkht khtaccttca cggttaccga a       51

<210> SEQ ID NO 23
<211> LENGTH: 54
<212> TYPE: DNA
<213> ORGANISM: Artificial Sequence
<220> FEATURE:
<223> OTHER INFORMATION: Synthetic polynucleotide

<400> SEQUENCE: 23
gatggtgaat ggacctackh tkhtkhtkht khtkhtacct tcacggttac cgaa    54

<210> SEQ ID NO 24
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 24
gatggtgaat ggacctackh tkhtkhtkht khtkhtkhta ccttcacggt taccgaa   57

<210> SEQ ID NO 25
<211> LENGTH: 54
<212> TYPE: DNA
<213> ORGANISM: Artificial Sequence
<220> FEATURE:
<223> OTHER INFORMATION: Synthetic polynucleotide

<400> SEQUENCE: 25
acgtacaaac tgattctgkh tkhtkhtkht khtkhtggtg aaaccacgac cgaa    54

<210> SEQ ID NO 26
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 26
acgtacaaac tgattctgkh tkhtkhtkht khtkhtkhtg gtgaaaccac gaccgaa   57

<210> SEQ ID NO 27
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 27
acgtacaaac tgattctgkh tkhtkhtkht khtkhtkhtk htggtgaaac cacgaccgaa   60

<210> SEQ ID NO 28
<211> LENGTH: 54
<212> TYPE: DNA
<213> ORGANISM: Artificial Sequence
<220> FEATURE:

<223> OTHER INFORMATION: Synthetic polynucleotide

<400> SEQUENCE: 28
aaacagtacg ccaacgatkh tkhtkhtkht khtkhttgga cctacgatga tgcg    54

<210> SEQ ID NO 29
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 29
aaacagtacg ccaacgatkh tkhtkhtkht khtkhtkhtt ggacctacga tgatgcg    57

<210> SEQ ID NO 30
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 30
aaacagtacg ccaacgatkh tkhtkhtkht khtkhtkhtk httggaccta cgatgatgcg    60

<210> SEQ ID NO 31
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 31
acgaaaacct tcacggttkh tkhtkhtggc ggttctgaca aaact    45

<210> SEQ ID NO 32
<211> LENGTH: 78
<212> TYPE: DNA
<213> ORGANISM: Artificial Sequence
<220> FEATURE:
<223> OTHER INFORMATION: Synthetic polynucleotide

<400> SEQUENCE: 32
aaaggcggta gcacgtackh tctgkhtctg khtkhtkhtk htkhtkhtkh tkhtacckht    60
accgaagcag tggatgca    78

<210> SEQ ID NO 33
<211> LENGTH: 81
<212> TYPE: DNA
<213> ORGANISM: Artificial Sequence
<220> FEATURE:
<223> OTHER INFORMATION: Synthetic polynucleotide

<400> SEQUENCE: 33
aaaggcggta gcacgtackh tctgkhtctg khtkhtkhtk htkhtkhtkh tkhtkhtacc    60
khtaccgaag cagtggatgc a    81

<210> SEQ ID NO 34
<211> LENGTH: 84
<212> TYPE: DNA
<213> ORGANISM: Artificial Sequence
<220> FEATURE:
<223> OTHER INFORMATION: Synthetic polynucleotide

<400> SEQUENCE: 34

```
aaaggcggta gcacgtackh tctgkhtctg khtkhtkhtk htkhtkhtkh tkhtkhtkht    60
accKhtaccg aagcagtgga tgca                                          84
```

<210> SEQ ID NO 35
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 35

```
gatgcgacga aaaccttcKh tgttkhtkht khtggcggtt ctgacaaaac t            51
```

<210> SEQ ID NO 36
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 36

```
gatgataaag gcggtagcKh tkhttackht ctgKhtctgk htggcaaaac cctgaaaggt   60
```

<210> SEQ ID NO 37
<211> LENGTH: 78
<212> TYPE: DNA
<213> ORGANISM: Artificial Sequence
<220> FEATURE:
<223> OTHER INFORMATION: Synthetic polynucleotide

<400> SEQUENCE: 37

```
gataatggcg tggatggtKh ttggKhttac khtkhtkhtk htkhtkhttt cKhtgttkht   60
gaaggcggtt ctgacaaa                                                 78
```

<210> SEQ ID NO 38
<211> LENGTH: 81
<212> TYPE: DNA
<213> ORGANISM: Artificial Sequence
<220> FEATURE:
<223> OTHER INFORMATION: Synthetic polynucleotide

<400> SEQUENCE: 38

```
gataatggcg tggatggtKh ttggKhttac khtkhtkhtk htkhtkhtKh tttcKhtgtt   60
khtgaaggcg gttctgacaa a                                             81
```

<210> SEQ ID NO 39
<211> LENGTH: 84
<212> TYPE: DNA
<213> ORGANISM: Artificial Sequence
<220> FEATURE:
<223> OTHER INFORMATION: Synthetic polynucleotide

<400> SEQUENCE: 39

```
gataatggcg tggatggtKh ttggKhttac khtkhtkhtk htkhtkhtKh tkhtttcKht   60
gttKhtgaag gcggttctga caaa                                          84
```

<210> SEQ ID NO 40
<211> LENGTH: 55
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 1, 3, 7, 9, 11, 12, 16, 18, 19, 20
<223> OTHER INFORMATION: X1 = T or S, X3 = K or R, X7 = N or K, X9 = K,
      N V or A, X11 = L or F, X12 = K or S, X16 = T or
      A or S, X18 = K or E, X19 = A or T, X20 = V or I
<221> NAME/KEY: VARIANT
<222> LOCATION: 22, 23, 24, 27, 28, 30, 31
<223> OTHER INFORMATION: X22 = A, T or V; X23 = A or E; X24 = T or V;
      X27 = K or Q; X28 = A, E, T or V; X30 = K or R; X31 = Q or D
<221> NAME/KEY: VARIANT
<222> LOCATION: 34, 35, 37, 39, 41, 43, 46
<223> OTHER INFORMATION: X34 = N or T; X35 = A, D, E or K; X37 =
      G or N; X39 = D or T; X41 = E or V; X43 = A, T or
      S; X46 = D, A, Y or T
<221> NAME/KEY: VARIANT
<222> LOCATION: 5, 6, 51, 53
<223> OTHER INFORMATION: X = hydrophobic
<221> NAME/KEY: VARIANT
<222> LOCATION: 38
<223> OTHER INFORMATION: X = non aromatic hydrophobic

<400> SEQUENCE: 40

Xaa Tyr Xaa Leu Xaa Xaa Xaa Gly Xaa Thr Xaa Xaa Gly Glu Thr Xaa
 1               5                  10                  15

Thr Xaa Xaa Xaa Asp Xaa Xaa Xaa Ala Glu Xaa Xaa Phe Xaa Xaa Tyr
            20                  25                  30

Ala Xaa Xaa Asn Xaa Xaa Xaa Gly Xaa Trp Xaa Tyr Asp Xaa Ala Thr
        35                  40                  45

Lys Thr Xaa Thr Xaa Thr Glu
    50                  55

<210> SEQ ID NO 41
<211> LENGTH: 55
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 1, 3, 5, 6, 7, 9, 11, 12, 16, 18, 19
<223> OTHER INFORMATION: X1 = T or S, X3 = K or R, X5 = I or V, X6 = L,
      I or V, X7 = N or K, X9 = K, N, V or A, X11 = L or
      F, X12 = K or S, X16 = T, A or S, X18 = K or E,
      X19 = A or T
<221> NAME/KEY: VARIANT
<222> LOCATION: 20, 22, 23, 24, 27, 28, 30, 31
<223> OTHER INFORMATION: X20 = V or I; X22 = A, T or V; X23 = A or E;
      X24 = T or V; X27 = K or Q; X28 = A, E, T or V; X30 = K
      or R; X31 = Q or D
<221> NAME/KEY: VARIANT
<222> LOCATION: 34, 35, 37, 38, 39, 41, 43, 46
<223> OTHER INFORMATION: X34 = N or T; X35 = A, D, E or K; X37 = G or
      N; X38 = V or I; X39 = D or T; X41 = E or V; X43 =
      A, T or S; X46 = D, A, Y or T

<400> SEQUENCE: 41

Xaa Tyr Xaa Leu Xaa Xaa Xaa Gly Xaa Thr Xaa Xaa Gly Glu Thr Xaa
 1               5                  10                  15

Thr Xaa Xaa Xaa Asp Xaa Xaa Xaa Ala Glu Xaa Xaa Phe Xaa Xaa Tyr
            20                  25                  30

Ala Xaa Xaa Asn Xaa Xaa Xaa Gly Xaa Trp Xaa Tyr Asp Xaa Ala Thr
        35                  40                  45

Lys Thr Phe Thr Val Thr Glu
    50                  55

<210> SEQ ID NO 42
<211> LENGTH: 55
<212> TYPE: PRT
<213> ORGANISM: Artificial Sequence
<220> FEATURE:
<223> OTHER INFORMATION: Synthetic polypeptide

```
<221> NAME/KEY: VARIANT
<222> LOCATION: 5, 6, 7, 9, 11, 12, 16, 18, 22
<223> OTHER INFORMATION: X5 = I or V; X6 = L, I or V; X7 = N or K;
      X9 = N or K; X11 = L or F; X12 = K or S; X16 = T or A; X18 = K or
      E; X22 = A, T or V
<221> NAME/KEY: VARIANT
<222> LOCATION: 23, 27, 28, 30, 34, 35, 37, 41, 43, 46
<223> OTHER INFORMATION: X23 = A or E; X27 = K or Q; X28 = A, E, T or V;
      X30 = K or R; X34 = N or T; X35 = A, D, E or K;
      X37 = G or N; X41 = E or V; X43 = A, T or S; X46 =
      D or A

<400> SEQUENCE: 42

Thr Tyr Lys Leu Xaa Xaa Xaa Gly Xaa Thr Xaa Xaa Gly Glu Thr Xaa
 1               5                  10                  15

Thr Xaa Ala Val Asp Xaa Xaa Thr Ala Glu Xaa Xaa Phe Xaa Gln Tyr
            20                  25                  30

Ala Xaa Xaa Asn Xaa Val Asp Gly Xaa Trp Xaa Tyr Asp Xaa Ala Thr
        35                  40                  45

Lys Thr Phe Thr Val Thr Glu
    50                  55

<210> SEQ ID NO 43
<211> LENGTH: 55
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 7, 8, 9, 10, 11, 12, 13
<223> OTHER INFORMATION: X7 = N or V, X8 = G, L or I, X9 K or G,
      X10 = Q, T or D, X11 = L, A or R, X12 = K or V, X13 = G, E or V
<221> NAME/KEY: VARIANT
<222> LOCATION: 14, 15, 16, 17, 19, 23, 24
<223> OTHER INFORMATION: X14 = E or V, X15 = A, T, R, I, P or V, X16 =
      T or I, X17 = R, W, L, K, V, T or I, X19 = A, L or
      I, X23 = A or G, X24 = T or E
<221> NAME/KEY: VARIANT
<222> LOCATION: 25, 28, 29, 31, 35, 36
<223> OTHER INFORMATION: X25 = A, V or F, X28 = V, I or Y, X29 = F, L,
      W, I or A, X31 = L or Q, X35 = A or D, X36 = K or N
<221> NAME/KEY: VARIANT
<222> LOCATION: 37, 38, 39, 41, 42, 45, 47, 48
<223> OTHER INFORMATION: X37 = T or G, X38 = V or I, X39 = E or D,
      X41 = V or E, X42 = W or F, X45 = D or K, X47 = E or A,
      X48 = T or I
<221> NAME/KEY: VARIANT
<222> LOCATION: 2
<223> OTHER INFORMATION: Xaa = aromatic hydrophobic
<221> NAME/KEY: VARIANT
<222> LOCATION: 4, 5, 6, 32, 51, 53
<223> OTHER INFORMATION: Xaa = hydrophobic
<221> NAME/KEY: VARIANT
<222> LOCATION: 33
<223> OTHER INFORMATION: Xaa = non aromatic hydrophobic

<400> SEQUENCE: 43

Thr Xaa Lys Xaa Xaa Xaa Xaa Xaa Xaa Xaa Xaa Xaa Xaa Xaa Xaa Xaa
 1               5                  10                  15

Xaa Glu Xaa Val Asp Ala Xaa Xaa Xaa Glu Lys Xaa Xaa Lys Xaa Xaa
            20                  25                  30

Xaa Asn Xaa Xaa Xaa Xaa Xaa Gly Xaa Xaa Thr Tyr Xaa Asp Xaa Xaa
        35                  40                  45

Lys Thr Xaa Thr Xaa Thr Glu
    50                  55

<210> SEQ ID NO 44
<211> LENGTH: 55
<212> TYPE: PRT
```

```
<213> ORGANISM: Artificial Sequence
<220> FEATURE:
<223> OTHER INFORMATION: Synthetic polypeptide
<221> NAME/KEY: VARIANT
<222> LOCATION: 2, 4, 5, 6, 7, 8, 9
<223> OTHER INFORMATION: X2 = Y,F,W or A, X4 = L,V,I,M,F,Y or A,
      X5 = L,V,I,F or M, X6 = L, V, I, F, M, A, Y or S,
      X7 = N or V, X8 = G, L or I, X9 = K or G
<221> NAME/KEY: VARIANT
<222> LOCATION: 10, 11, 12, 13, 14, 15, 16
<223> OTHER INFORMATION: X10 = Q, T or D, X11 = L, A or R, X12 = K or V,
      X13 = G, E or V , X14 = E or V, X15 = A, T, R, I,
      P or V, X16 = T or I
<221> NAME/KEY: VARIANT
<222> LOCATION: 17, 19, 23, 24
<223> OTHER INFORMATION: X17 = R, W, L, K, V, T or I, X19 = A, L or I,
      X23 = A or G, X24 = T or E
<221> NAME/KEY: VARIANT
<222> LOCATION: 25, 28, 29, 31, 32, 33, 35, 36
<223> OTHER INFORMATION: X25 = A, V or F, X28 = V, I or Y, X29 = F, L,
      W, I or A, X31 = L or Q, X32 = W, F, L, M, Y or I, X33 = L, V,
      I or A, X35 = A or D, X36 = K or N
<221> NAME/KEY: VARIANT
<222> LOCATION: 37, 38, 39, 41, 42, 45, 47, 48, 51, 53
<223> OTHER INFORMATION: X37 = T or G, X38 = V or I, X39 = E or D,
      X41 = V or E, X42 = W or F, X45 = D or K, X47 = E or A, X48 = T or
      I, X51 = L, V, I, F, M or W, X53 = L, V, I, F or M

<400> SEQUENCE: 44

Thr Xaa Lys Xaa Xaa Xaa Xaa Xaa Xaa Xaa Xaa Xaa Xaa Xaa Xaa
 1               5                  10                  15

Xaa Glu Xaa Val Asp Ala Xaa Xaa Xaa Glu Lys Xaa Xaa Lys Xaa Xaa
            20                  25                  30

Xaa Asn Xaa Xaa Xaa Xaa Xaa Gly Xaa Xaa Thr Tyr Xaa Asp Xaa Xaa
        35                  40                  45

Lys Thr Xaa Thr Xaa Thr Glu
        50                  55

<210> SEQ ID NO 45
<211> LENGTH: 201
<212> TYPE: DNA
<213> ORGANISM: Artificial Sequence
<220> FEATURE:
<223> OTHER INFORMATION: Synthetic polynucleotide

<400> SEQUENCE: 45
gatgataaag gcggtagcac gtacaaactg attctgaacg gcaaaaccct gaaaggtgaa      60
accacgaccg aagcagtgga tgcagcaacg gcagaaaaag ttttcaaaca gtacgccaac     120
gataatggcg tggatggtga atggacctac gatgatgcga cgaaaacctt cacggttacc     180
gaaggcggtt ctgacaaaac t                                               201

<210> SEQ ID NO 46
<211> LENGTH: 67
<212> TYPE: PRT
<213> ORGANISM: Artificial Sequence
<220> FEATURE:
<223> OTHER INFORMATION: Synthetic polypeptide

<400> SEQUENCE: 46

Asp Asp Lys Gly Gly Ser Thr Tyr Lys Leu Ile Leu Asn Gly Lys Thr
 1               5                  10                  15

Leu Lys Gly Glu Thr Thr Thr Glu Ala Val Asp Ala Ala Thr Ala Glu
            20                  25                  30

Lys Val Phe Lys Gln Tyr Ala Asn Asp Asn Gly Val Asp Gly Glu Trp
        35                  40                  45
```

```
Thr Tyr Asp Asp Ala Thr Lys Thr Phe Thr Val Thr Glu Gly Gly Ser
        50                  55                  60

Asp Lys Thr
65

<210> SEQ ID NO 47
<211> LENGTH: 24
<212> TYPE: PRT
<213> ORGANISM: Artificial Sequence
<220> FEATURE:
<223> OTHER INFORMATION: Synthetic polypeptide

<400> SEQUENCE: 47

Gln Lys Ser Thr Gln Asn Ala Ile Asp Gly Ile Thr Ser Lys Val Asn
1               5                   10                  15

Ser Val Ile Glu Lys Met Asn Thr
            20

<210> SEQ ID NO 48
<211> LENGTH: 24
<212> TYPE: PRT
<213> ORGANISM: Artificial Sequence
<220> FEATURE:
<223> OTHER INFORMATION: Synthetic polypeptide

<400> SEQUENCE: 48

Lys Glu Ser Thr Gln Lys Ala Ile Asp Gly Ile Thr Asn Arg Val Asn
1               5                   10                  15

Ser Val Ile Glu Lys Met Asn Thr
            20

<210> SEQ ID NO 49
<211> LENGTH: 24
<212> TYPE: PRT
<213> ORGANISM: Artificial Sequence
<220> FEATURE:
<223> OTHER INFORMATION: Synthetic polypeptide

<400> SEQUENCE: 49

Leu Lys Ser Thr Gln Ala Ala Ile Asp Gln Ile Asn Gly Lys Leu Asn
1               5                   10                  15

Arg Val Ile Glu Lys Thr Asn Glu
            20

<210> SEQ ID NO 50
<211> LENGTH: 24
<212> TYPE: PRT
<213> ORGANISM: Artificial Sequence
<220> FEATURE:
<223> OTHER INFORMATION: Synthetic polypeptide

<400> SEQUENCE: 50

Leu Lys Ser Thr Gln Ala Ala Ile Asp Gln Ile Asn Gly Lys Leu Asn
1               5                   10                  15

Arg Leu Ile Glu Lys Thr Asn Asp
            20

<210> SEQ ID NO 51
<211> LENGTH: 24
<212> TYPE: PRT
<213> ORGANISM: Artificial Sequence
<220> FEATURE:
<223> OTHER INFORMATION: Synthetic polypeptide

<400> SEQUENCE: 51
```

-continued

```
Lys Glu Ser Thr Gln Lys Ala Ile Asp Gly Ile Thr Asn Lys Val Asn
1               5                   10                  15

Ser Ile Ile Asp Lys Met Asn Thr
            20

<210> SEQ ID NO 52
<211> LENGTH: 24
<212> TYPE: PRT
<213> ORGANISM: Artificial Sequence
<220> FEATURE:
<223> OTHER INFORMATION: Synthetic polypeptide

<400> SEQUENCE: 52

Arg Glu Ser Thr Gln Lys Ala Val Asp Gly Ile Thr Asn Lys Val Asn
1               5                   10                  15

Ser Ile Ile Asp Lys Met Asn Thr
            20

<210> SEQ ID NO 53
<211> LENGTH: 24
<212> TYPE: PRT
<213> ORGANISM: Artificial Sequence
<220> FEATURE:
<223> OTHER INFORMATION: Synthetic polypeptide

<400> SEQUENCE: 53

Tyr Lys Ser Thr Gln Ser Ala Ile Asp Gln Ile Thr Gly Lys Leu Asn
1               5                   10                  15

Arg Leu Ile Glu Lys Thr Asn Gln
            20

<210> SEQ ID NO 54
<211> LENGTH: 24
<212> TYPE: PRT
<213> ORGANISM: Artificial Sequence
<220> FEATURE:
<223> OTHER INFORMATION: Synthetic polypeptide

<400> SEQUENCE: 54

Gln Lys Ser Thr Gln Glu Ala Ile Asp Lys Ile Thr Asn Lys Val Asn
1               5                   10                  15

Asn Ile Val Asp Lys Met Asn Arg
            20

<210> SEQ ID NO 55
<211> LENGTH: 24
<212> TYPE: PRT
<213> ORGANISM: Artificial Sequence
<220> FEATURE:
<223> OTHER INFORMATION: Synthetic polypeptide

<400> SEQUENCE: 55

Lys Gly Ser Thr Gln Lys Ala Ile Asp Lys Ile Thr Ser Lys Val Asn
1               5                   10                  15

Asn Ile Ile Asp Lys Met Asn Lys
            20

<210> SEQ ID NO 56
<211> LENGTH: 24
<212> TYPE: PRT
<213> ORGANISM: Artificial Sequence
<220> FEATURE:
<223> OTHER INFORMATION: Synthetic polypeptide
```

```
<400> SEQUENCE: 56

Tyr Lys Ser Thr Gln Ala Ala Ile Asp Gln Ile Thr Gly Lys Leu Asn
1               5                   10                  15

Arg Leu Ile Glu Lys Thr Asn Thr
            20

<210> SEQ ID NO 57
<211> LENGTH: 24
<212> TYPE: PRT
<213> ORGANISM: Artificial Sequence
<220> FEATURE:
<223> OTHER INFORMATION: Synthetic polypeptide

<400> SEQUENCE: 57

Lys Glu Ser Thr Gln Lys Ala Ile Asp Gln Ile Thr Ser Lys Val Asn
1               5                   10                  15

Asn Ile Val Asp Arg Met Asn Thr
            20

<210> SEQ ID NO 58
<211> LENGTH: 24
<212> TYPE: PRT
<213> ORGANISM: Artificial Sequence
<220> FEATURE:
<223> OTHER INFORMATION: Synthetic polypeptide

<400> SEQUENCE: 58

Arg Asp Ser Thr Gln Arg Ala Ile Asp Asn Met Gln Asn Lys Leu Asn
1               5                   10                  15

Asn Val Ile Asp Lys Met Asn Lys
            20

<210> SEQ ID NO 59
<211> LENGTH: 24
<212> TYPE: PRT
<213> ORGANISM: Artificial Sequence
<220> FEATURE:
<223> OTHER INFORMATION: Synthetic polypeptide

<400> SEQUENCE: 59

Lys Glu Ser Thr Gln Lys Ala Ile Asp Gln Ile Thr Thr Lys Ile Asn
1               5                   10                  15

Asn Ile Ile Asp Lys Met Asn Gly
            20

<210> SEQ ID NO 60
<211> LENGTH: 24
<212> TYPE: PRT
<213> ORGANISM: Artificial Sequence
<220> FEATURE:
<223> OTHER INFORMATION: Synthetic polypeptide

<400> SEQUENCE: 60

Leu Lys Ser Thr Gln Ala Ala Ile Asp Gln Ile Asn Gly Lys Leu Asn
1               5                   10                  15

Arg Leu Ile Glu Lys Thr Asn Glu
            20

<210> SEQ ID NO 61
<211> LENGTH: 24
<212> TYPE: PRT
<213> ORGANISM: Artificial Sequence
<220> FEATURE:
<223> OTHER INFORMATION: Synthetic polypeptide
```

<400> SEQUENCE: 61

Tyr Lys Ser Thr Gln Ala Ala Ile Asp Gln Ile Thr Gly Lys Leu Asn
 1               5                   10                  15

Arg Leu Ile Glu Lys Thr Asn Lys
            20

<210> SEQ ID NO 62
<211> LENGTH: 24
<212> TYPE: PRT
<213> ORGANISM: Artificial Sequence
<220> FEATURE:
<223> OTHER INFORMATION: Synthetic polypeptide

<400> SEQUENCE: 62

Lys Ala Ser Thr Gln Lys Ala Ile Asp Glu Ile Thr Thr Lys Ile Asn
 1               5                   10                  15

Asn Ile Ile Glu Lys Met Asn Gly
            20

<210> SEQ ID NO 63
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 63

Thr Gln Asn Ala Ile Asp Gly Ile Thr Ser Lys Val Asn Ser Val Ile
 1               5                   10                  15

Glu

<210> SEQ ID NO 64
<211> LENGTH: 17
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 3, 4, 7, 10, 11, 14
<223> OTHER INFORMATION: Xaa = Any Amino Acid

<400> SEQUENCE: 64

Thr Gln Xaa Xaa Ile Asp Xaa Ile Thr Xaa Xaa Val Asn Xaa Val Ile
 1               5                   10                  15

Glu

<210> SEQ ID NO 65
<211> LENGTH: 17
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 3, 5, 7, 9, 10
<223> OTHER INFORMATION: X3 = A, E, K, N, R or S, X5 = I or V, X7 =  E,
      G, K, N or Q, X9 = T or N, X10 = G, N, S or T
<221> NAME/KEY: VARIANT
<222> LOCATION: 11, 12, 14, 15, 16, 17
<223> OTHER INFORMATION: X11 = K or R, X12 = I, L or V, X14 = N, R or S,
      X15 = I, L or V, X16 = I or V, X17 = D or E

<400> SEQUENCE: 65

Thr Gln Xaa Ala Xaa Asp Xaa Ile Xaa Xaa Xaa Xaa Asn Xaa Xaa Xaa
 1               5                   10                  15

Xaa

```
<210> SEQ ID NO 66
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 66
```

Leu Gln Lys Ser Ile Gln Asn Leu Ile Asp Gly Ile Thr Ser Leu Val
1               5                   10                  15

Asn Ser Ile

```
<210> SEQ ID NO 67
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 67
```

Leu Lys Glu Ser Ile Gln Lys Leu Ile Asp Gly Ile Thr Asn Leu Val
1               5                   10                  15

Asn Ser Ile

```
<210> SEQ ID NO 68
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 68
```

Leu Leu Lys Ser Ile Gln Ala Leu Ile Asp Gln Ile Asn Gly Leu Leu
1               5                   10                  15

Asn Arg Ile

```
<210> SEQ ID NO 69
<211> LENGTH: 28
<212> TYPE: PRT
<213> ORGANISM: Artificial Sequence
<220> FEATURE:
<223> OTHER INFORMATION: Synthetic polypeptide

<400> SEQUENCE: 69
```

Ile Ala Ala Leu Gln Lys Ser Ile Gln Asn Leu Ile Asp Gly Ile Thr
1               5                   10                  15

Ser Leu Val Asn Ser Ile Ile Glu Leu Met Asn Thr
            20                  25

```
<210> SEQ ID NO 70
<211> LENGTH: 28
<212> TYPE: PRT
<213> ORGANISM: Artificial Sequence
<220> FEATURE:
<223> OTHER INFORMATION: Synthetic polypeptide

<400> SEQUENCE: 70
```

Ile Ala Ala Leu Lys Glu Ser Ile Gln Lys Leu Ile Asp Gly Ile Thr
1               5                   10                  15

Asn Leu Val Asn Ser Ile Ile Glu Leu Met Asn Thr
            20                  25

<210> SEQ ID NO 71
<211> LENGTH: 28
<212> TYPE: PRT
<213> ORGANISM: Artificial Sequence
<220> FEATURE:
<223> OTHER INFORMATION: Synthetic polypeptide

<400> SEQUENCE: 71

Ile Ala Ala Leu Leu Lys Ser Ile Gln Ala Leu Ile Asp Gln Ile Asn
1               5                   10                  15

Gly Leu Leu Asn Arg Ile Ile Glu Leu Thr Asn Glu
            20                  25

<210> SEQ ID NO 72
<211> LENGTH: 22
<212> TYPE: PRT
<213> ORGANISM: Artificial Sequence
<220> FEATURE:
<223> OTHER INFORMATION: Synthetic polypeptide

<400> SEQUENCE: 72

Cys Ala Ala Leu Gln Lys Ser Ile Gln Asn Leu Ile Asp Gly Ile Thr
1               5                   10                  15

Ser Leu Val Asn Ser Ile
            20

<210> SEQ ID NO 73
<211> LENGTH: 22
<212> TYPE: PRT
<213> ORGANISM: Artificial Sequence
<220> FEATURE:
<223> OTHER INFORMATION: Synthetic polypeptide

<400> SEQUENCE: 73

Cys Ala Ala Leu Gln Lys Ser Ile Gln Asn Leu Ile Asp Gly Ile Thr
1               5                   10                  15

Ser Leu Val Asn Ser Ile
            20

<210> SEQ ID NO 74
<211> LENGTH: 22
<212> TYPE: PRT
<213> ORGANISM: Artificial Sequence
<220> FEATURE:
<223> OTHER INFORMATION: Synthetic polypeptide

<400> SEQUENCE: 74

Cys Ala Ala Leu Lys Glu Ser Ile Gln Lys Leu Ile Asp Gly Ile Thr
1               5                   10                  15

Asn Leu Val Asn Ser Ile
            20

<210> SEQ ID NO 75
<211> LENGTH: 22
<212> TYPE: PRT
<213> ORGANISM: Artificial Sequence
<220> FEATURE:
<223> OTHER INFORMATION: Synthetic polypeptide

<400> SEQUENCE: 75

Cys Ala Ala Leu Lys Glu Ser Ile Gln Lys Leu Ile Asp Gly Ile Thr
1               5                   10                  15

Asn Leu Val Asn Ser Ile
            20

```
<210> SEQ ID NO 76
<211> LENGTH: 22
<212> TYPE: PRT
<213> ORGANISM: Artificial Sequence
<220> FEATURE:
<223> OTHER INFORMATION: Synthetic polypeptide

<400> SEQUENCE: 76

Cys Ala Ala Leu Leu Lys Ser Ile Gln Ala Leu Ile Asp Gln Ile Asn
1               5                   10                  15

Gly Leu Leu Asn Arg Ile
            20

<210> SEQ ID NO 77
<211> LENGTH: 22
<212> TYPE: PRT
<213> ORGANISM: Artificial Sequence
<220> FEATURE:
<223> OTHER INFORMATION: Synthetic polypeptide

<400> SEQUENCE: 77

Cys Ala Ala Leu Leu Lys Ser Ile Gln Ala Leu Ile Asp Gln Ile Asn
1               5                   10                  15

Gly Leu Leu Asn Arg Ile
            20

<210> SEQ ID NO 78
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 78

Ile Ala Ala Leu Gln Lys Ser Ile Gln Asn Leu Ile Asp Gly Ile Thr
1               5                   10                  15

Ser Leu Val Asn Ser Ile Ile Glu Leu Met Asn Thr Cys Arg Arg
            20                  25                  30

<210> SEQ ID NO 79
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 79

Ile Ala Ala Leu Gln Lys Ser Ile Gln Asn Leu Ile Asp Gly Ile Thr
1               5                   10                  15

Ser Leu Val Asn Ser Ile Ile Glu Leu Met Asn Thr Cys Arg Arg
            20                  25                  30

<210> SEQ ID NO 80
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 80

Ile Ala Ala Leu Lys Glu Ser Ile Gln Lys Leu Ile Asp Gly Ile Thr
1               5                   10                  15

Asn Leu Val Asn Ser Ile Ile Glu Leu Met Asn Thr Cys Arg Arg
```

-continued

```
                    20                  25                  30

<210> SEQ ID NO 81
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 81

Ile Ala Ala Leu Lys Glu Ser Ile Gln Lys Leu Ile Asp Gly Ile Thr
1               5                   10                  15

Asn Leu Val Asn Ser Ile Ile Glu Leu Met Asn Thr Cys Arg Arg
            20                  25                  30

<210> SEQ ID NO 82
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 82

Ile Ala Ala Leu Leu Lys Ser Ile Gln Ala Leu Ile Asp Gln Ile Asn
1               5                   10                  15

Gly Leu Leu Asn Arg Ile Ile Glu Leu Thr Asn Glu Cys Arg Arg
            20                  25                  30

<210> SEQ ID NO 83
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 83

Ile Ala Ala Leu Leu Lys Ser Ile Gln Ala Leu Ile Asp Gln Ile Asn
1               5                   10                  15

Gly Leu Leu Asn Arg Ile Ile Glu Leu Thr Asn Glu Cys Arg Arg
            20                  25                  30

<210> SEQ ID NO 84
<211> LENGTH: 15
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 2, 4, 5, 7,
<223> OTHER INFORMATION: X2 = E or Q, X4 = V, I or M, X5 = D or N,
      X7 = E or Q
<221> NAME/KEY: VARIANT
<222> LOCATION: 8, 10, 13, 14, 15
<223> OTHER INFORMATION: X8 = T, E, I or R, X10 = Q or T, X13 = L or Y,
      X14 = N or D, X15 = G, E or A

<400> SEQUENCE: 84

Glu Xaa Gly Xaa Xaa Arg Xaa Xaa Gly Xaa Ala Ala Xaa Xaa Xaa
1               5                   10                  15

<210> SEQ ID NO 85
<211> LENGTH: 15
<212> TYPE: PRT
<213> ORGANISM: Artificial Sequence
<220> FEATURE:
<223> OTHER INFORMATION: Synthetic polypeptide
<221> NAME/KEY: VARIANT
```

```
<222> LOCATION: 4, 15
<223> OTHER INFORMATION: X4 = I or V, X15 = G or E

<400> SEQUENCE: 85

Glu Glu Gly Xaa Asp Arg Glu Thr Gly Gln Ala Ala Leu Asn Xaa
1               5                   10                  15

<210> SEQ ID NO 86
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 86

Glu Glu Gly Val Asp Arg Glu Thr Gly Gln Ala Ala Leu Asn Gly
1               5                   10                  15

<210> SEQ ID NO 87
<211> LENGTH: 21
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 4, 7, 11, 14, 18, 21
<223> OTHER INFORMATION: Xaa = Any Hydrophobic Amino Acid

<400> SEQUENCE: 87

Gln Lys Ser Xaa Gln Asn Xaa Ile Asp Gly Xaa Thr Ser Xaa Val Asn
1               5                   10                  15

Ser Xaa Ile Glu Xaa
            20

<210> SEQ ID NO 88
<211> LENGTH: 21
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 4, 7, 11, 14, 18, 21
<223> OTHER INFORMATION: Xaa = Any Hydrophobic Amino Acid

<400> SEQUENCE: 88

Lys Glu Ser Xaa Gln Lys Xaa Ile Asp Gly Xaa Thr Asn Xaa Val Asn
1               5                   10                  15

Ser Xaa Ile Glu Xaa
            20

<210> SEQ ID NO 89
<211> LENGTH: 21
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 4, 7, 11, 14, 18, 21
<223> OTHER INFORMATION: Xaa = Any Hydrophobic Amino Acid

<400> SEQUENCE: 89

Leu Lys Ser Xaa Gln Ala Xaa Ile Asp Gln Xaa Asn Gly Xaa Leu Asn
1               5                   10                  15

Arg Xaa Ile Glu Xaa
            20
```

```
<210> SEQ ID NO 90
<211> LENGTH: 21
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 4, 7, 11, 14, 18, 21
<223> OTHER INFORMATION: Xaa = Any Hydrophobic Amino Acid

<400> SEQUENCE: 90

Leu Lys Ser Xaa Gln Ala Xaa Ile Asp Gln Xaa Asn Gly Xaa Leu Asn
 1               5                  10                  15

Arg Xaa Ile Glu Xaa
            20

<210> SEQ ID NO 91
<211> LENGTH: 21
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 4, 7, 11, 14, 18, 21
<223> OTHER INFORMATION: Xaa = Any Hydrophobic Amino Acid

<400> SEQUENCE: 91

Lys Glu Ser Xaa Gln Lys Xaa Ile Asp Gly Xaa Thr Asn Xaa Val Asn
 1               5                  10                  15

Ser Xaa Ile Asp Xaa
            20

<210> SEQ ID NO 92
<211> LENGTH: 21
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 4, 7, 11, 14, 18, 21
<223> OTHER INFORMATION: Xaa = Any Hydrophobic Amino Acid

<400> SEQUENCE: 92

Arg Glu Ser Xaa Gln Lys Xaa Val Asp Gly Xaa Thr Asn Xaa Val Asn
 1               5                  10                  15

Ser Xaa Ile Asp Xaa
            20

<210> SEQ ID NO 93
<211> LENGTH: 21
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 4, 7, 11, 14, 18, 21
<223> OTHER INFORMATION: Xaa = Any Hydrophobic Amino Acid

<400> SEQUENCE: 93

Tyr Lys Ser Xaa Gln Ser Xaa Ile Asp Gln Xaa Thr Gly Xaa Leu Asn
 1               5                  10                  15

Arg Xaa Ile Glu Xaa
            20

<210> SEQ ID NO 94
<211> LENGTH: 21
<212> TYPE: PRT
```

```
<213> ORGANISM: Artificial Sequence
<220> FEATURE:
<223> OTHER INFORMATION: Synthetic polypeptide
<221> NAME/KEY: VARIANT
<222> LOCATION: 4, 7, 11, 14, 18, 21
<223> OTHER INFORMATION: Xaa = Any Hydrophobic Amino Acid

<400> SEQUENCE: 94

Gln Lys Ser Xaa Gln Glu Xaa Ile Asp Lys Xaa Thr Asn Xaa Val Asn
1               5                   10                  15

Asn Xaa Val Asp Xaa
            20

<210> SEQ ID NO 95
<211> LENGTH: 21
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 4, 7, 11, 14, 18, 21
<223> OTHER INFORMATION: Xaa = AnyHydrophobic  Amino Acid

<400> SEQUENCE: 95

Lys Gly Ser Xaa Gln Lys Xaa Ile Asp Lys Xaa Thr Ser Xaa Val Asn
1               5                   10                  15

Asn Xaa Ile Asp Xaa
            20

<210> SEQ ID NO 96
<211> LENGTH: 21
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 4, 7, 11, 14, 18, 21
<223> OTHER INFORMATION: Xaa = Any Hydrophobic Amino Acid

<400> SEQUENCE: 96

Tyr Lys Ser Xaa Gln Ala Xaa Ile Asp Gln Xaa Thr Gly Xaa Leu Asn
1               5                   10                  15

Arg Xaa Ile Glu Xaa
            20

<210> SEQ ID NO 97
<211> LENGTH: 21
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 4, 7, 11, 14, 18, 21
<223> OTHER INFORMATION: Xaa = Any Hydrophobic Amino Acid

<400> SEQUENCE: 97

Lys Glu Ser Xaa Gln Lys Xaa Ile Asp Gln Xaa Thr Ser Xaa Val Asn
1               5                   10                  15

Asn Xaa Val Asp Xaa
            20

<210> SEQ ID NO 98
<211> LENGTH: 21
<212> TYPE: PRT
<213> ORGANISM: Artificial Sequence
<220> FEATURE:
<223> OTHER INFORMATION: Synthetic polypeptide
```

```
<221> NAME/KEY: VARIANT
<222> LOCATION: 4, 7, 11, 14, 18, 21
<223> OTHER INFORMATION: Xaa = Any Hydrophobic Amino Acid

<400> SEQUENCE: 98

Arg Asp Ser Xaa Gln Arg Xaa Ile Asp Asn Xaa Gln Asn Xaa Leu Asn
1               5                   10                  15

Asn Xaa Ile Asp Xaa
            20

<210> SEQ ID NO 99
<211> LENGTH: 21
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 4, 7, 11, 14, 18, 21
<223> OTHER INFORMATION: Xaa = Any Hydrophobic Amino Acid

<400> SEQUENCE: 99

Lys Glu Ser Xaa Gln Lys Xaa Ile Asp Gln Xaa Thr Thr Xaa Ile Asn
1               5                   10                  15

Asn Xaa Ile Asp Xaa
            20

<210> SEQ ID NO 100
<211> LENGTH: 21
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 4, 7, 11, 14, 18, 21
<223> OTHER INFORMATION: Xaa = Any Hydrophobic Amino Acid

<400> SEQUENCE: 100

Leu Lys Ser Xaa Gln Ala Xaa Ile Asp Gln Xaa Asn Gly Xaa Leu Asn
1               5                   10                  15

Arg Xaa Ile Glu Xaa
            20

<210> SEQ ID NO 101
<211> LENGTH: 21
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 4, 7, 11, 14, 18, 21
<223> OTHER INFORMATION: Xaa = Any Hydrophobic Amino Acid

<400> SEQUENCE: 101

Tyr Lys Ser Xaa Gln Ala Xaa Ile Asp Gln Xaa Thr Gly Xaa Leu Asn
1               5                   10                  15

Arg Xaa Ile Glu Xaa
            20

<210> SEQ ID NO 102
<211> LENGTH: 21
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 4, 7, 11, 14, 18, 21
<223> OTHER INFORMATION: Xaa = Any Hydrophobic Amino Acid
```

<400> SEQUENCE: 102

Lys Ala Ser Xaa Gln Lys Xaa Ile Asp Glu Xaa Thr Thr Xaa Ile Asn
1               5                   10                  15

Asn Xaa Ile Glu Xaa
            20

<210> SEQ ID NO 103
<211> LENGTH: 271
<212> TYPE: PRT
<213> ORGANISM: Artificial Sequence
<220> FEATURE:
<223> OTHER INFORMATION: Synthetic polypeptide

<400> SEQUENCE: 103

Gly Leu Phe Gly Ala Ile Ala Gly Phe Ile Glu Asn Gly Trp Glu Gly
1               5                   10                  15

Met Ile Asp Gly Trp Tyr Gly Phe Arg His Gln Asn Ser Glu Gly Thr
            20                  25                  30

Gly Gln Ala Ala Asp Leu Lys Ser Thr Gln Ala Ala Ile Asp Gln Ile
        35                  40                  45

Asn Gly Lys Leu Asn Arg Val Ile Glu Lys Thr Asn Glu Lys Phe His
    50                  55                  60

Gln Ile Glu Lys Glu Phe Ser Glu Val Glu Gly Arg Ile Gln Asp Leu
65                  70                  75                  80

Glu Lys Tyr Val Glu Asp Thr Lys Ile Asp Leu Trp Ser Tyr Asn Ala
                85                  90                  95

Glu Leu Leu Val Ala Leu Glu Asn Gln His Thr Ile Asp Leu Thr Asp
            100                 105                 110

Ser Glu Met Asn Lys Leu Phe Glu Lys Thr Arg Arg Gln Leu Arg Glu
        115                 120                 125

Asn Ala Glu Asp Met Gly Asn Gly Cys Phe Lys Ile Tyr His Lys Cys
130                 135                 140

Asp Asn Ala Cys Ile Glu Ser Ile Arg Asn Gly Thr Tyr Asp His Asp
145                 150                 155                 160

Val Tyr Arg Asp Glu Ala Leu Asn Asn Arg Phe Gln Ser Ala Gly Ser
                165                 170                 175

Ala Gly Asp Asn Ser Thr Ala Thr Leu Cys Leu Gly His His Ala Val
            180                 185                 190

Pro Asn Gly Thr Leu Val Lys Thr Ile Thr Asp Asp Gln Ile Glu Val
        195                 200                 205

Thr Asn Ala Thr Glu Leu Val Gln Ser Ser Gly Ser Ala Gly Ser Ala
    210                 215                 220

Asn Asp Lys Pro Phe Gln Asn Val Asn Lys Ile Thr Tyr Gly Ala Cys
225                 230                 235                 240

Pro Lys Tyr Val Lys Lys Gln Asn Thr Leu Lys Leu Ala Thr Gly Met
                245                 250                 255

Arg Lys Leu Ala Ala Ala Leu Glu His His His His His His
            260                 265                 270

<210> SEQ ID NO 104
<211> LENGTH: 258
<212> TYPE: PRT
<213> ORGANISM: Artificial Sequence
<220> FEATURE:
<223> OTHER INFORMATION: Synthetic polypeptide

<400> SEQUENCE: 104

Gly Leu Cys Gly Ala Ile Ala Gly Phe Ile Glu Asn Gly Trp Glu Gly
1               5                   10                  15

Met Ile Asp Gly Trp Tyr Gly Phe Arg His Gln Asn Ser Glu Gly Thr
            20                  25                  30

Gly Gln Ala Ala Asp Leu Lys Cys Thr Gln Ala Ala Ile Asp Gln Ile
        35                  40                  45

Asn Gly Lys Leu Asn Arg Val Ile Glu Lys Thr Asn Glu Lys Asp His
    50                  55                  60

Gln Ile Glu Lys Glu Phe Ser Glu Asp Glu Gly Arg Ile Gln Asp Leu
65              70                  75                  80

Glu Lys Tyr Val Glu Asp Thr Lys Ile Asp Leu Trp Ser Tyr Asn Ala
                85                  90                  95

Glu Leu Leu Val Ala Leu Glu Asn Gln His Thr Ile Asp Leu Thr Asp
                100                 105                 110

Ser Glu Met Cys Lys Cys Phe Glu Lys Thr Arg Arg Gln Leu Arg Glu
            115                 120                 125

Asn Ala Glu Asp Met Gly Asn Gly Cys Phe Lys Ile Tyr His Lys Cys
    130                 135                 140

Asp Asn Ala Cys Ile Glu Ser Ile Arg Asn Gly Thr Tyr Asp His Asp
145                 150                 155                 160

Val Tyr Arg Asp Glu Ala Leu Asn Asn Arg Phe Gln Gly Ser Ala Gly
                165                 170                 175

Ser Ala Gly Asp Asn Ser Thr Ala Thr Leu Cys Leu Gly His His Ala
                180                 185                 190

Val Pro Asn Gly Thr Leu Val Lys Thr Ile Thr Asp Asp Gln Ile Glu
                195                 200                 205

Val Thr Asn Ala Thr Glu Leu Val Gln Ser Ser Gly Ser Ala Gly Ser
210                 215                 220

Ala Asn Asp Lys Pro Phe Gln Asn Thr Asn Lys Glu Thr Thr Gly Ala
225                 230                 235                 240

Cys Pro Lys Tyr Val Lys Lys Gln Asn Thr Leu Lys Leu Ala Thr Gly
                245                 250                 255

Met Arg

<210> SEQ ID NO 105
<211> LENGTH: 25
<212> TYPE: PRT
<213> ORGANISM: Artificial Sequence
<220> FEATURE:
<223> OTHER INFORMATION: Synthetic polypeptide

<400> SEQUENCE: 105

Leu Gln Gly Ser Ile Tyr Ala Leu Asp Lys Glu Ile Thr Gln Leu Ala
1               5                   10                  15

Ile Asp Val Thr Leu Lys Val Asn Ile
            20                  25

<210> SEQ ID NO 106
<211> LENGTH: 26
<212> TYPE: PRT
<213> ORGANISM: Artificial Sequence
<220> FEATURE:
<223> OTHER INFORMATION: Synthetic polypeptide

<400> SEQUENCE: 106

Leu Gly Ser Gly Ile Ala Ala Leu Lys Glu Ser Ile Gln Lys Leu Ile
1               5                   10                  15

```
Asp Gly Ile Thr Asn Leu Val Asn Ser Ile
            20                  25

<210> SEQ ID NO 107
<211> LENGTH: 26
<212> TYPE: PRT
<213> ORGANISM: Artificial Sequence
<220> FEATURE:
<223> OTHER INFORMATION: Synthetic polypeptide

<400> SEQUENCE: 107

Leu Ser Gly Tyr Ile Ala Asp Leu Glu Ser Thr Ile Lys Ala Leu Asp
 1               5                  10                  15

Gly Val Ile Asn Lys Leu Asn Ser Ile Ile
            20                  25

<210> SEQ ID NO 108
<211> LENGTH: 26
<212> TYPE: PRT
<213> ORGANISM: Artificial Sequence
<220> FEATURE:
<223> OTHER INFORMATION: Synthetic polypeptide

<400> SEQUENCE: 108

Leu Gly Tyr Ala Ile Asp Lys Leu Ser Thr Gln Ile Ala Ile Leu Gly
 1               5                  10                  15

Val Thr Ile Lys Val Leu Ser Ile Ile Ile
            20                  25

<210> SEQ ID NO 109
<211> LENGTH: 26
<212> TYPE: PRT
<213> ORGANISM: Artificial Sequence
<220> FEATURE:
<223> OTHER INFORMATION: Synthetic polypeptide

<400> SEQUENCE: 109

Leu Tyr Ala Ala Ile Lys Glu Leu Thr Gln Lys Ile Ile Asp Leu Val
 1               5                  10                  15

Thr Asn Ile Val Asn Leu Ile Ile Asp Ile
            20                  25

<210> SEQ ID NO 110
<211> LENGTH: 26
<212> TYPE: PRT
<213> ORGANISM: Artificial Sequence
<220> FEATURE:
<223> OTHER INFORMATION: Synthetic polypeptide

<400> SEQUENCE: 110

Leu Ala Ala Asp Ile Glu Ser Leu Gln Lys Ala Ile Asp Gly Leu Thr
 1               5                  10                  15

Asn Lys Ile Asn Ser Leu Ile Asp Lys Ile
            20                  25

<210> SEQ ID NO 111
<211> LENGTH: 26
<212> TYPE: PRT
<213> ORGANISM: Artificial Sequence
<220> FEATURE:
<223> OTHER INFORMATION: Synthetic polypeptide

<400> SEQUENCE: 111

Leu Ala Asp Lys Ile Ser Thr Leu Lys Ala Ile Ile Gly Val Leu Asn
```

```
                1               5                   10                  15
Lys Val Ile Ser Ile Leu Asp Lys Met Ile
            20                  25

<210> SEQ ID NO 112
<211> LENGTH: 26
<212> TYPE: PRT
<213> ORGANISM: Artificial Sequence
<220> FEATURE:
<223> OTHER INFORMATION: Synthetic polypeptide

<400> SEQUENCE: 112

Leu Asp Lys Glu Ile Thr Gln Leu Ala Ile Asp Ile Val Thr Leu Lys
1               5                   10                  15

Val Asn Ile Ile Ile Leu Lys Met Asn Ile
            20                  25

<210> SEQ ID NO 113
<211> LENGTH: 26
<212> TYPE: PRT
<213> ORGANISM: Artificial Sequence
<220> FEATURE:
<223> OTHER INFORMATION: Synthetic polypeptide

<400> SEQUENCE: 113

Leu Lys Glu Ser Ile Gln Lys Leu Ile Asp Gly Ile Thr Asn Leu Val
1               5                   10                  15

Asn Ser Ile Ile Asp Leu Met Asn Thr Ile
            20                  25

<210> SEQ ID NO 114
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 114

Lys Glu Ser Thr Gln Lys Ala Ile Asp Gly Val Thr Asn Lys Val Asn
1               5                   10                  15

Ser

<210> SEQ ID NO 115
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 115

Gln Lys Ser Thr Gln Asn Ala Ile Asp Gly Ile Thr Ser Lys Val Asn
1               5                   10                  15

Ser Val Ile Glu
            20

<210> SEQ ID NO 116
<211> LENGTH: 25
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 1, 4, 8, 11, 15, 18, 22, 25
<223> OTHER INFORMATION: Xaa = Any Hydrophobic Amino Acid
<221> NAME/KEY: VARIANT
```

```
<222> LOCATION: 2, 3
<223> OTHER INFORMATION: Xaa = Any Amino Acid

<400> SEQUENCE: 116

Xaa Xaa Xaa Xaa Gln Lys Ser Xaa Gln Asn Xaa Ile Asp Gly Xaa Thr
1               5                   10                  15

Ser Xaa Val Asn Ser Xaa Ile Glu Xaa
            20                  25

<210> SEQ ID NO 117
<211> LENGTH: 25
<212> TYPE: PRT
<213> ORGANISM: Artificial Sequence
<220> FEATURE:
<223> OTHER INFORMATION: Synthetic polypeptide

<400> SEQUENCE: 117

Ile Ala Ala Leu Gln Lys Ser Ile Gln Asn Leu Ile Asp Gly Ile Thr
1               5                   10                  15

Ser Leu Val Asn Ser Ile Ile Glu Leu
            20                  25

<210> SEQ ID NO 118
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 118

Gln Lys Ser Thr Ile Asn Ala Leu Asp Gly Ile Ile Ser Lys Leu Asn
1               5                   10                  15

Ser Val Ile Glu
            20

<210> SEQ ID NO 119
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 119

Gln Leu Ser Thr Gln Ile Ala Ile Leu Gly Thr Ile Lys Val Leu
1               5                   10                  15

Ser Val Ile Ile
            20

<210> SEQ ID NO 120
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 120

Gln Lys Leu Thr Gln Asn Ile Ile Asp Leu Ile Thr Ser Ile Val Asn
1               5                   10                  15

Leu Val Ile Glu
            20

<210> SEQ ID NO 121
<211> LENGTH: 20
<212> TYPE: PRT
```

<213> ORGANISM: Artificial Sequence
<220> FEATURE:
<223> OTHER INFORMATION: Synthetic polypeptide

<400> SEQUENCE: 121

Ile Lys Ser Leu Gln Asn Ala Ile Asp Gly Leu Thr Ser Lys Ile Asn
1               5                   10                  15

Ser Leu Ile Glu
            20

<210> SEQ ID NO 122
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 122

Gln Ile Ser Thr Leu Asn Ala Ile Ile Gly Ile Leu Ser Lys Val Ile
1               5                   10                  15

Ser Val Leu Glu
            20

<210> SEQ ID NO 123
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 123

Gln Lys Ile Thr Gln Leu Ala Ile Asp Ile Ile Thr Leu Lys Val Asn
1               5                   10                  15

Ile Val Ile Leu
            20

<210> SEQ ID NO 124
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 124

Ile Ala Ala Leu Gln Lys Ser Ile Gln Asn Leu Ile Asp Gly Ile Thr
1               5                   10                  15

Ser Leu Val Asn Ser Ile Ile Glu Leu Met Asn Thr Cys Arg Arg
            20                  25                  30

<210> SEQ ID NO 125
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 125

Ile Ala Ala Leu Lys Glu Ser Ile Gln Lys Leu Ile Asp Gly Ile Thr
1               5                   10                  15

Asn Leu Val Asn Ser Ile Ile Glu Leu Met Asn Thr Cys Arg Arg
            20                  25                  30

<210> SEQ ID NO 126
<211> LENGTH: 31

```
<212> TYPE: PRT
<213> ORGANISM: Artificial Sequence
<220> FEATURE:
<223> OTHER INFORMATION: Synthetic polypeptide

<400> SEQUENCE: 126

Ile Ala Ala Leu Leu Lys Ser Ile Gln Ala Leu Ile Asp Gln Ile Asn
 1               5                  10                  15
Gly Leu Leu Asn Arg Ile Ile Glu Leu Thr Asn Glu Cys Arg Arg
            20                  25                  30

<210> SEQ ID NO 127
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 127

Ile Ala Ala Leu Leu Lys Ser Ile Gln Ala Leu Ile Asp Gln Ile Asn
 1               5                  10                  15
Gly Leu Leu Asn Arg Ile Ile Glu Leu Thr Asn Asp Cys Arg Arg
            20                  25                  30

<210> SEQ ID NO 128
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 128

Ile Ala Ala Leu Lys Glu Ser Ile Gln Lys Leu Ile Asp Gly Ile Thr
 1               5                  10                  15
Asn Leu Val Asn Ser Ile Ile Asp Leu Met Asn Thr Cys Arg Arg
            20                  25                  30

<210> SEQ ID NO 129
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 129

Ile Ala Ala Leu Arg Glu Ser Ile Gln Lys Leu Val Asp Gly Ile Thr
 1               5                  10                  15
Asn Leu Val Asn Ser Ile Ile Asp Leu Met Asn Thr Cys Arg Arg
            20                  25                  30

<210> SEQ ID NO 130
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 130

Ile Ala Ala Leu Tyr Lys Ser Ile Gln Ser Leu Ile Asp Gln Ile Thr
 1               5                  10                  15
Gly Leu Leu Asn Arg Ile Ile Glu Leu Thr Asn Gln Cys Arg Arg
            20                  25                  30

<210> SEQ ID NO 131
```

```
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 131

Ile Ala Ala Leu Gln Lys Ser Ile Gln Glu Leu Ile Asp Lys Ile Thr
1               5                   10                  15

Asn Leu Val Asn Asn Ile Val Asp Leu Met Asn Arg Cys Arg Arg
            20                  25                  30

<210> SEQ ID NO 132
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 132

Ile Ala Ala Leu Lys Gly Ser Ile Gln Lys Leu Ile Asp Lys Ile Thr
1               5                   10                  15

Ser Leu Val Asn Asn Ile Ile Asp Leu Met Asn Lys Cys Arg Arg
            20                  25                  30

<210> SEQ ID NO 133
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 133

Ile Ala Ala Leu Tyr Lys Ser Ile Gln Ala Leu Ile Asp Gln Ile Thr
1               5                   10                  15

Gly Leu Leu Asn Arg Ile Ile Glu Leu Thr Asn Thr Cys Arg Arg
            20                  25                  30

<210> SEQ ID NO 134
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 134

Ile Ala Ala Leu Lys Glu Ser Ile Gln Lys Leu Ile Asp Gln Ile Thr
1               5                   10                  15

Ser Leu Val Asn Asn Ile Val Asp Leu Met Asn Thr Cys Arg Arg
            20                  25                  30

<210> SEQ ID NO 135
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 135

Ile Ala Ala Leu Arg Asp Ser Ile Gln Arg Leu Ile Asp Asn Ile Gln
1               5                   10                  15

Asn Leu Leu Asn Asn Ile Ile Asp Leu Met Asn Lys Cys Arg Arg
            20                  25                  30
```

```
<210> SEQ ID NO 136
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 136

Ile Ala Ala Leu Lys Glu Ser Ile Gln Lys Leu Ile Asp Gln Ile Thr
1               5                   10                  15

Thr Leu Ile Asn Asn Ile Ile Asp Leu Met Asn Gly Cys Arg Arg
            20                  25                  30

<210> SEQ ID NO 137
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 137

Ile Ala Ala Leu Leu Lys Ser Ile Gln Ala Leu Ile Asp Gln Ile Asn
1               5                   10                  15

Gly Leu Leu Asn Arg Ile Ile Glu Leu Thr Asn Glu Cys Arg Arg
            20                  25                  30

<210> SEQ ID NO 138
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 138

Ile Ala Ala Leu Tyr Lys Ser Ile Gln Ala Leu Ile Asp Gln Ile Thr
1               5                   10                  15

Gly Leu Leu Asn Arg Ile Ile Glu Leu Thr Asn Lys Cys Arg Arg
            20                  25                  30

<210> SEQ ID NO 139
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 139

Ile Ala Ala Leu Lys Ala Ser Ile Gln Lys Leu Ile Asp Glu Ile Thr
1               5                   10                  15

Thr Leu Ile Asn Asn Ile Ile Glu Leu Met Asn Gly Cys Arg Arg
            20                  25                  30

<210> SEQ ID NO 140
<211> LENGTH: 23
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 2, 3, 4, 5, 7, 8, 11, 12, 15, 16, 18, 19, 20, 21, 22
<223> OTHER INFORMATION: Xaa = Any Amino Acid

<400> SEQUENCE: 140

Val Xaa Xaa Xaa Xaa Ala Xaa Xaa Val Phe Xaa Xaa Tyr Ala Xaa Xaa
1               5                   10                  15
```

```
Asn Xaa Xaa Xaa Xaa Xaa Trp
            20

<210> SEQ ID NO 141
<211> LENGTH: 23
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 2, 3, 4, 5, 7, 8, 11, 12, 15, 16, 18, 19, 20, 21, 22
<223> OTHER INFORMATION: Xaa = A, D, F, S, V or Y

<400> SEQUENCE: 141

Val Xaa Xaa Xaa Xaa Ala Xaa Xaa Val Phe Xaa Xaa Tyr Ala Xaa Xaa
 1               5                  10                  15

Asn Xaa Xaa Xaa Xaa Xaa Trp
            20

<210> SEQ ID NO 142
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 142

Thr Tyr Lys Leu Ile Leu Asn Gly Lys Thr Leu Lys Gly Glu Thr Thr
 1               5                  10                  15

<210> SEQ ID NO 143
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 143

Gly Val Asp Gly Glu Trp Thr Tyr Asp Asp Ala Thr Lys Thr Phe Thr
 1               5                  10                  15

Val Thr Glu

<210> SEQ ID NO 144
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 144

Thr Glu Ala Val Asp Ala Ala Thr Ala Glu Lys Val Phe Lys Gln Tyr
 1               5                  10                  15

Ala Asn Asp Asn
            20

<210> SEQ ID NO 145
<211> LENGTH: 20
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 2, 3, 4, 5, 6, 7, 8, 10, 11, 12, 14, 15, 16, 18, 19
<223> OTHER INFORMATION: Xaa = Any Amino Acid

<400> SEQUENCE: 145
```

```
Thr Xaa Xaa Xaa Xaa Xaa Xaa Xaa Ala Xaa Xaa Xaa Phe Xaa Xaa Xaa
 1               5                  10                  15

Ala Xaa Xaa Asn
         20

<210> SEQ ID NO 146
<211> LENGTH: 20
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 2, 3, 4, 5, 6, 7, 8, 10, 11, 12, 14, 15, 16, 18, 19
<223> OTHER INFORMATION: Xaa = A, D, F, S, V or Y

<400> SEQUENCE: 146

Thr Xaa Xaa Xaa Xaa Xaa Xaa Xaa Ala Xaa Xaa Xaa Phe Xaa Xaa Xaa
 1               5                  10                  15

Ala Xaa Xaa Asn
         20

<210> SEQ ID NO 147
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 147

Lys Leu Ile Leu Asn Gly Lys Thr Leu Lys Gly Glu Thr Thr
 1               5                  10

<210> SEQ ID NO 148
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 148

Glu Lys Val Phe Lys Gln Tyr Ala Asn Asp Asn Gly Val Asp Gly Glu
 1               5                  10                  15

Trp Thr

<210> SEQ ID NO 149
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 149

Phe Thr Val Thr Glu
 1               5

<210> SEQ ID NO 150
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 150

Thr Glu Ala Val Asp Ala Ala Thr Ala
 1               5
```

<210> SEQ ID NO 151
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 151

Tyr Asp Asp Ala Thr Lys Thr
1               5

<210> SEQ ID NO 152
<211> LENGTH: 9
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 2, 3, 4, 5, 6, 7, 8
<223> OTHER INFORMATION: Xaa = Any Amino Acid

<400> SEQUENCE: 152

Thr Xaa Xaa Xaa Xaa Xaa Xaa Xaa Ala
1               5

<210> SEQ ID NO 153
<211> LENGTH: 7
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 2, 3, 4, 5, 6
<223> OTHER INFORMATION: Xaa = Any Amino Acid

<400> SEQUENCE: 153

Tyr Xaa Xaa Xaa Xaa Xaa Thr
1               5

<210> SEQ ID NO 154
<211> LENGTH: 9
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 2, 3, 4, 5, 6, 7, 8
<223> OTHER INFORMATION: Xaa = A, D, F, S, V or Y

<400> SEQUENCE: 154

Thr Xaa Xaa Xaa Xaa Xaa Xaa Xaa Ala
1               5

<210> SEQ ID NO 155
<211> LENGTH: 7
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 2, 3, 4, 5, 6
<223> OTHER INFORMATION: Xaa = A, D, F, S, V or Y

<400> SEQUENCE: 155

Tyr Xaa Xaa Xaa Xaa Xaa Thr
1               5

<210> SEQ ID NO 156

```
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 156

Thr Tyr Lys Leu Ile
1               5

<210> SEQ ID NO 157
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 157

Glu Thr Thr Thr Glu Ala Val Asp Ala Ala Thr Ala Glu Lys Val Phe
1               5                   10                  15

Lys Gln Tyr Ala Asn
            20

<210> SEQ ID NO 158
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 158

Thr Tyr Asp Asp Ala Thr Lys Thr Phe Thr
1               5                   10

<210> SEQ ID NO 159
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 159

Leu Asn Gly Lys Thr Leu Lys Gly
1               5

<210> SEQ ID NO 160
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 160

Asp Asn Gly Val Asp Gly Glu Trp
1               5

<210> SEQ ID NO 161
<211> LENGTH: 8
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 2, 3, 4, 5, 6, 7
<223> OTHER INFORMATION: Xaa = Any Amino Acid

<400> SEQUENCE: 161
```

```
Leu Xaa Xaa Xaa Xaa Xaa Xaa Gly
 1               5

<210> SEQ ID NO 162
<211> LENGTH: 8
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 2, 3, 4, 5, 6, 7
<223> OTHER INFORMATION: Xaa = Any Amino Acid

<400> SEQUENCE: 162

Asp Xaa Xaa Xaa Xaa Xaa Xaa Trp
 1               5

<210> SEQ ID NO 163
<211> LENGTH: 8
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 2, 3, 4, 5, 6, 7
<223> OTHER INFORMATION: Xaa = A, D, F, S, V or Y

<400> SEQUENCE: 163

Leu Xaa Xaa Xaa Xaa Xaa Xaa Gly
 1               5

<210> SEQ ID NO 164
<211> LENGTH: 8
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 2, 3, 4, 5, 6, 7
<223> OTHER INFORMATION: Xaa =  A, D, F, S, V or Y

<400> SEQUENCE: 164

Asp Xaa Xaa Xaa Xaa Xaa Xaa Trp
 1               5

<210> SEQ ID NO 165
<211> LENGTH: 33
<212> TYPE: PRT
<213> ORGANISM: Artificial Sequence
<220> FEATURE:
<223> OTHER INFORMATION: Synthetic polypeptide

<400> SEQUENCE: 165

Glu Ala Val Asp Ala Ala Thr Ala Glu Lys Val Phe Lys Gln Tyr Ala
 1               5                  10                  15

Asn Asp Asn Gly Val Asp Gly Glu Trp Thr Tyr Asp Asp Ala Thr Lys
            20                  25                  30

Thr

<210> SEQ ID NO 166
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 166
```

```
Thr Tyr Lys Leu Ile Leu Asn Gly Lys Thr Leu Lys Gly Glu Thr Thr
1               5                   10                  15

Thr

<210> SEQ ID NO 167
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 167

Phe Thr Val Thr Glu
1               5

<210> SEQ ID NO 168
<211> LENGTH: 17
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 3, 5, 7, 8, 9, 10, 11, 12, 13, 14, 16
<223> OTHER INFORMATION: Xaa = Any Amino Acid

<400> SEQUENCE: 168

Thr Tyr Xaa Leu Xaa Leu Xaa Xaa Xaa Xaa Xaa Xaa Xaa Xaa Thr Xaa
1               5                   10                  15

Thr

<210> SEQ ID NO 169
<211> LENGTH: 5
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 2, 4, 5
<223> OTHER INFORMATION: Xaa = Any Amino Acid

<400> SEQUENCE: 169

Phe Xaa Val Xaa Xaa
1               5

<210> SEQ ID NO 170
<211> LENGTH: 17
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 3, 5, 7, 8, 9, 10, 11, 12, 13, 14, 16
<223> OTHER INFORMATION: Xaa = A, D, F, S, V or Y

<400> SEQUENCE: 170

Thr Tyr Xaa Leu Xaa Leu Xaa Xaa Xaa Xaa Xaa Xaa Xaa Xaa Thr Xaa
1               5                   10                  15

Thr

<210> SEQ ID NO 171
<211> LENGTH: 5
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 2, 4, 5
```

<223> OTHER INFORMATION: Xaa = A, D, F, S, V or Y

<400> SEQUENCE: 171

Phe Xaa Val Xaa Xaa
1               5

<210> SEQ ID NO 172
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 172

Lys Thr Leu Lys Gly Glu Thr Thr Thr Glu Ala Val Asp Ala Ala Thr
1               5                   10                  15

Ala Glu Lys Val Phe Lys Gln Tyr Ala Asn Asp Asn Gly Val Asp
            20                  25                  30

<210> SEQ ID NO 173
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 173

Thr Tyr Lys Leu Ile Leu Asn Gly
1               5

<210> SEQ ID NO 174
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 174

Gly Glu Trp Thr Tyr Asp Asp Ala Thr Lys Thr Phe Thr Val Thr Glu
1               5                   10                  15

<210> SEQ ID NO 175
<211> LENGTH: 8
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 1, 3, 5, 7
<223> OTHER INFORMATION: Xaa = Any Amino Acid

<400> SEQUENCE: 175

Xaa Tyr Xaa Leu Xaa Leu Xaa Gly
1               5

<210> SEQ ID NO 176
<211> LENGTH: 16
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 2, 4, 6, 7, 8, 9, 10, 11, 13, 15
<223> OTHER INFORMATION: Xaa = Any Amino Acid

<400> SEQUENCE: 176

Gly Xaa Trp Xaa Tyr Xaa Xaa Xaa Xaa Xaa Xaa Phe Xaa Val Xaa Glu

```
<210> SEQ ID NO 177
<211> LENGTH: 8
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 1, 3, 5, 7
<223> OTHER INFORMATION: Xaa = A, D, F, S, V or Y

<400> SEQUENCE: 177

Xaa Tyr Xaa Leu Xaa Leu Xaa Gly
 1               5

<210> SEQ ID NO 178
<211> LENGTH: 16
<212> TYPE: PRT
<213> ORGANISM: Artificial Sequence
<220> FEATURE:
<223> OTHER INFORMATION: Synthetic polypeptide
<221> NAME/KEY: VARIANT
<222> LOCATION: 2, 4, 6, 7, 8, 9, 10, 11, 13, 15
<223> OTHER INFORMATION: Xaa = A, D, F, S, V or Y

<400> SEQUENCE: 178

Gly Xaa Trp Xaa Tyr Xaa Xaa Xaa Xaa Xaa Xaa Phe Xaa Val Xaa Glu
 1               5                  10                  15
```